US009790256B2

(12) United States Patent
Bunnik et al.

(10) Patent No.: US 9,790,256 B2
(45) Date of Patent: Oct. 17, 2017

(54) THERAPEUTIC HPV18 VACCINES

(71) Applicant: Janssen Vaccines & Prevention B.V., Leiden (NL)

(72) Inventors: Evelien Margaretha Bunnik, Mico, TX (US); Jerome Hubertina Henricus Victor Custers, Alphen aan den Rijn (NL); Gerrit Christiaan Scheper, Amstelveen (NL); Koen Oosterhuis, Haarlem (NL); Taco Gilles Uil, Amsterdam (NL); Selina Khan, Leiden (NL)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 0 days.

(21) Appl. No.: 15/242,383

(22) Filed: Aug. 19, 2016

(65) Prior Publication Data
US 2017/0051019 A1    Feb. 23, 2017

(30) Foreign Application Priority Data

Aug. 20, 2015  (EP) .................................... 15181791
Feb. 18, 2016  (EP) .................................... 16156334

(51) Int. Cl.
| C07K 14/005 | (2006.01) |
| A61K 39/00 | (2006.01) |
| A61K 39/12 | (2006.01) |
| C07K 14/025 | (2006.01) |
| C12N 7/00 | (2006.01) |
| C12N 15/86 | (2006.01) |

(52) U.S. Cl.
CPC ............ *C07K 14/005* (2013.01); *A61K 39/00* (2013.01); *A61K 39/12* (2013.01); *C07K 14/025* (2013.01); *C12N 7/00* (2013.01); *C12N 15/86* (2013.01); *A61K 2039/525* (2013.01); *A61K 2039/53* (2013.01); *A61K 2039/54* (2013.01); *A61K 2039/585* (2013.01); *A61K 2039/6031* (2013.01); *C12N 2710/10043* (2013.01); *C12N 2710/20034* (2013.01)

(58) Field of Classification Search
None
See application file for complete search history.

(56) References Cited

U.S. PATENT DOCUMENTS

| 5,057,540 A | 10/1991 | Kensil et al. |
| 5,122,458 A | 6/1992 | Post et al. |
| 5,385,839 A | 1/1995 | Stinski |
| 5,559,099 A | 9/1996 | Wickham et al. |
| 5,837,511 A | 11/1998 | Falck et al. |
| 5,846,782 A | 12/1998 | Wickham et al. |
| 5,851,806 A | 12/1998 | Kovesdi et al. |
| 5,891,690 A | 4/1999 | Massie |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |
| 6,733,994 B2 | 5/2004 | Weiner et al. |
| 7,270,811 B2 | 9/2007 | Bout et al. |
| 8,932,607 B2 | 1/2015 | Custers et al. |
| 9,119,813 B2 | 9/2015 | Radosevic et al. |
| 9,125,870 B2 | 9/2015 | Radosevic et al. |
| 2007/0014810 A1 | 1/2007 | Baker et al. |
| 2013/0122038 A1 | 5/2013 | Radosevic et al. |
| 2015/0196632 A1 | 7/2015 | Radosevic et al. |
| 2015/0320854 A1 | 11/2015 | Radosevic et al. |
| 2016/0122396 A1 | 5/2016 | Bunnik et al. |

FOREIGN PATENT DOCUMENTS

| EP | 1183368 A2 | 3/2002 |
| EP | 1230354 A1 | 1/2004 |
| EP | 990041 B1 | 6/2006 |
| EP | 1385946 B1 | 12/2009 |
| WO | 9003184 A1 | 4/1990 |
| WO | 9014837 A1 | 12/1990 |
| WO | 9609378 A1 | 3/1996 |
| WO | 9611711 A1 | 4/1996 |
| WO | 9839411 A1 | 9/1998 |
| WO | 0070071 A1 | 11/2000 |
| WO | 03104467 A1 | 12/2003 |
| WO | 2004004762 A1 | 1/2004 |
| WO | 2005002620 A1 | 1/2005 |
| WO | 2005080556 A2 | 9/2005 |
| WO | 2006048459 A2 | 5/2006 |
| WO | 2007073513 | 6/2007 |
| WO | 2007100908 A2 | 9/2007 |
| WO | 2007104792 A2 | 9/2007 |
| WO | 2009106362 A1 | 9/2009 |
| WO | 2010060719 A1 | 6/2010 |

(Continued)

OTHER PUBLICATIONS

Oosterhuis et al., Rational design of DNA vaccines for the induction of HPV16 E6 and E7 specific cytotoxic T cell responses, Human Gene Therapy, 2012, pp. 1-42, Mary Ann Liebert, Inc.
Prakash et al., Amino acids necessary for DNA contact and dimerization imply novel motifs in the papillomavirus E2 trans-activator, Genes & Development, 1992, pp. 105-116, vol. 6, Cold Spring Harbor Laboratory Press.
Lundegaard et al., NetMHC-3.0: accurate web accessible predictions of human, mouse and monkey MHC class I affinities for peptides of length 8-11, Nucleic Acids Research, May 7, 2008, pp. W509-W512, vol. 36, web server issue.
Kim et al., Clearance of persistent HPV infection and cervical lesion by therapeutic DNA vaccine in CIN 3 patients, Nature Communications, Oct. 30, 2014, pp. 1-14, Macmillan Publishers Limited.
Zhang et al., Immune epitope database analysis resource (IEBD-AR), Nucleic Acids Research, 2008, W513-518, vol. 36.

(Continued)

*Primary Examiner* — Nianxiang (Nick) Zou
(74) *Attorney, Agent, or Firm* — Panitch Schwarze Belisario & Nadel LLP

(57) ABSTRACT

Provided is designer nucleic acid constructs and polypeptides that can be used as therapeutic vaccines against HPV18 and/or HPV16.

28 Claims, 26 Drawing Sheets

(56) References Cited

FOREIGN PATENT DOCUMENTS

| WO | 2010073043 A1 | 7/2010 |
|---|---|---|
| WO | 2011098592 A1 | 8/2011 |
| WO | 2013083287 A1 | 6/2013 |

OTHER PUBLICATIONS

Moscicki, Anna-Barbara M.D., HPV Vaccines: Today and in the Future, Journal of Adolescent Health, 2008, pp. S26-S40, vol. 43.
Van Der Burg et al., Therapeutic vaccination against human papilloma virus induced malignancies, Current Opinion in Immunology, 2011, pp. 252-57, vol. 23.
Wieking et al., A non-oncogenic HPV 16 E6/E7 vaccine enhances treatment of HPV expressing tumors, Cancer Gene Therapy, 2012, pp. 667-674, vol. 19.
Yan et al., Induction of antitumor immunity in vivo following delivery of a novel HPV-16 DNA vaccine encoding an E6/E7 fusion antigen, Vaccine, 2009, pp. 431-40, vol. 27.
Yao et al., A Novel Tetracycline-Inducible Viral Replication Switch, Human Gene Therapy, Feb. 10, 1999, pp. 419-427, vol. 10, Mary Ann Liebert, Inc.
Yoshida et al., Adenovirus-Mediated Inducible Gene Expression through Tetracycline-Controllable Transactivator with Nuclear Localization Signal, Biochemical and Biophysical Research Communications, 1997, pp. 426-430, vol. 230.
Yugawa et al., Molecular mechanisms of cervical carcinogenesis by high-risk human papillomaviruses: novel functions of E6 and E7 oncoproteins, Rev. Med. Viral., 2009, pp. 97-113, vol. 19.
Zwaveling et al., Established Human Papillomavirus Type 16-Expressing Tumors Are Effectively Eradicated Following Vaccination with Long Peptides, The Journal of Immunology, 2002, pp. 350-358, vol. 169.
Abbink et al., Comparative Seroprevalence and Immunogenicity of Six Rare Serotype Recombinant Adenovirus Vaccine Vectors from Subgroups B and D, Journal of Virology, May 2007, pp. 4654-4663, vol. 81, No. 9.
Brokaw et al., Amino Acids Critical for the Functions of the Bovine Papillomavirus Type 1 E2 Transactivator, Journal of Virology, Jan. 1996, pp. 23-29, vol. 70, No. 1.
Cottingham et al., Preventing Spontaneous Genetic Rearrangements in the Transgene Cassettes of Adenovirus Vectors, Biotechnology and Bioengineering, 2012, pp. 719-728, vol. 109.
Daayana et al., Phase II trial of imiquimod and HPV therapeutic vaccination in patients with vulval intraepithelial neoplasia, British Journal of Cancer, 2010, pp. 1129-1136, vol. 102.
De Groot et al., HIV vaccine development by computer assisted design: the GAIA vaccine, Vaccine, 2005, pp. 2136-2148, vol. 23.
De Jong et al., Frequent Detection of Human Papillomavirus 16 E2-specific T-helper Immunity in Healthy Subjects, Cancer Research, Jan. 15, 2002, pp. 472-479, vol. 62.
Edholm et al., Adenovirus Vector Designed for Expression of Toxic Proteins, Journal of Virology, Oct. 2001, pp. 3579-3584, vol. 75, No. 2.
Evans et al., Development of Stable Liquid Formulations for Adenovirus-Based Vaccines, Journal of Pharmaceutical Sciences, Oct. 2004, pp. 2458-2475, vol. 93, No. 10.
Fallaux et al., New Helper Cells and Matched Early Region 1-Deleted Adenovirus Vectors Prevent Generation of Replication-Competent Adenoviruses, Human Gene Therapy, Sep. 1, 1998, pp. 1909-1917, vol. 9.
Gao et al., A Cell Line for High-Yield Production of E1-Deleted Adenovirus Vectors without the Emergence of Replication-Competent Virus, Human Gene Therapy, Jan. 1, 2000, pp. 213-219, vol. 11.
Gilbert et al., Establishment and validation of new complementing cells for production of E1-deleted adenovirus vectors in serum-free suspension culture, Journal of Virological Methods, 2014, pp. 177-188, vol. 208.
Hamid et al., Anti-programmed death-1 and anti-programmed death-ligand 1 antibodies in cancer therapy, Expert Opinion on Biological Therapy, 2013, pp. 847-861, vol. 13, No. 6.

Havenga et al., Novel replication-incompetent adenoviral B-group vectors: high vector stability and yield in PER.C6 cells, Journal of General Virology, 2006, pp. 2135-2143, vol. 87.
Hildesheim et al., Effect of Human Papillomavirus 16/18 L1 Virus-like Particle Vaccine Among Young Women With Preexisting Infection: A Randomized Trial, Journal of American Medical Association, Aug. 15, 2007, pp. 743-753, vol. 298, No. 7.
Lin et al., Treatment of Established Tumors with a Novel Vaccine That Enhances Major Histocompatibility Class II Presentation of Tumor Antigen, Cancer Research, Jan. 1, 1996, pp. 21-26, vol. 56.
Massimi et al., Transformation Assays for HPV Oncoproteins, Methods in Molecular Medicine, 2005, pp. 381-395, vol. 119, Humana Press Inc., Totowa, NJ, USA.
Matthews et al., Development and use of a 293 cell line expressing lac repressor for the rescue of recombinant adenoviruses expressing high levels of rabies virus glycoprotein, Journal of General Virology, 1999, pp. 345-353, vol. 80.
Mellman et al., Cancer immunotherapy comes of age, Nature, Mar. 27, 2014, pp. 480-489, vol. 480, No. 7378.
Mullick et al., The cumate gene-switch: a system for regulated expression in mammalian cells, BMC Biotechnology, 2006, pp. 43, vol. 6, 18 pages.
Munger et al., The E6 and E7 Genes of the Human Papillomavirus Type 16 Together Are Necessary and Sufficient for Transformation of Primary Human Keratinocytes, Journal of Virology, Oct. 1989, pp. 4417-4421, vol. 63, No. 10.
Ogun et al., The Oligomerization Domain of C4-Binding Protein (C4bp) Acts as an Adjuvant, and the Fusion Protein comprised of the 19-Kilodalton Merozoite Surface Protein 1 Fused with the Murine C4bp Domain Protects Mice against Malaria, Infection and Immunity, Aug. 2008, pp. 3817-3823, vol. 76, No. 8.
Oosterhuis et al., DNA Vaccines and Intradermal Vaccination by DNA Tattooing, Current Topics Microbiology, 2012, 30 pages, Springer-Verlag Berlin Heidelberg 2010.
Oosterhuis et al., Preclinical development of highly effective and safe DNA vaccines directed against HPV 16 E6 and E7, International Journal of Cancer, 2011, pp. 397-406, vol. 129.
PCT International Search Report, PCT/EP2016/069618 dated Oct. 27, 2016.
Hoganson et al., Development of a Stable Adenoviral Vector Formulation, BioProcessing Journal, Mar. 2002, pp. 43-48.
Hoof et al., NetMHCpan, a method for MHC class I binding prediction beyond humans, Immunogenetics, Jan. 2009, pp. 1-13, vol. 61, No. 1.
Horwitz, Marshall S., Adenoviruses, Fields Virology, 1996, Third Edition, Chapter 68, pp. 2149-2171.
Kenter et al., Vaccination against HPV-16 Oncoproteins for Vulvar Intraepithelial Neoplasia, The New England Journal of Medicine, 2009, pp. 1838-1847, vol. 361.
Kovesdi et al., Adenoviral Producer Cells, Viruses, 2010, pp. 1681-1703, vol. 2.
Peters et al., Examining the independent binding assumption for binding of peptide epitopes to MHC-I molecules, Bioinformatics, 2003, pp. 1765-1772, vol. 19, No. 14.
Rubinchik et al., Adenoviral vector which delivers FasL-GFP fusion protein regulated by the tet-inducible expression system, Gene Therapy, 2000, pp. 875-885, vol. 7.
Sakai et al., Targeted Mutagenesis of the Human Papillomavirus Type 16 E2 Transactivation Domain Reveals Separable Transcriptional Activation and DNA Replication Functions, Journal of Virology, Mar. 1996, pp. 1602-1611, vol. 70, No. 3.
Sambrook et al., Molecular Cloning, A Laboratory Manual, Second Edition, 1989, includes table of contents, 32 pages.
Sedman et al., The Full-Length E6 Protein of Human Papillomavirus Type 16 Has Transforming and trans-Activating Activities and Cooperates with E7 to Immortalize Keratinocytes in Culture, Journal of Virology, Sep. 1991, pp. 1860-1866, vol. 63, No. 9.
Smahel et al., Modified HPV16 E7 Genes as DNA Vaccine against E7-Containing Oncogenic Cells, Virology, 2001, pp. 231-238, vol. 281.
GenBank: ACI43214.1. HPV-16 E6/E7 fusion protein [synthetic construct]. Dated Jan. 14, 2009.

(56) References Cited

OTHER PUBLICATIONS

Mishra et al., Dendritic Cell-Mediated, DNA-Based Vaccination against Hepatitis C Induces the Multi-Epitope-Specific Response of Humanized, HLA Transgenic Mice, PLOS, Aug. 2014, E104606, vol. 9, No. 8.

Moise et al., VennVax, a DNA-prime, peptide-boost multi-T-cell epitope poxvirus vaccine, induces protective immunity against vaccinia infection by T cell response alone, Vaccine, 2011, pp. 501-511, vol. 29.

Moss et al., HelicoVax: Epitope-based therapeutic Helicobacter pylori vaccination in a mouse model, Vaccine, 2011, pp. 2085-2091, vol. 29.

Ohlshlager, et al., An improved rearranged Human Papillomavirus Type 16 E7 DNA vaccine candidate (HPV-16 E7SH) induces an E7 wildtype-specific T cell response, Vaccine, 2006, pp. 2880-2893, vol. 24.

Brandsma et al., Therapeutic vaccination of rabbits with a ubiquitin-fused papillomavirus E1, E2, E6 and E7 DNA vaccine, Vaccine, 2007, pp. 6158-6163, vol. 25.

Almajhdi et al., Design of a Highly Effective Therapeutic HPV16 E6/E7-Specific DNA Vaccine: Optimization by Different Ways of Sequence Rearrangements (Shuffling), PLOS ONE, Nov. 25, 1014, pp. e113461, vol. 9, No. 11, 15 pages.

F.E. Henken et al., Preclinical safety evaluation of DNA vaccines encoding modified HPV16 E6 and E7, Vaccine, 2012, pp. 4259-4266, vol. 30, Elsevier LTD.

Int'l Search Report and Written Opinion dated Feb. 23, 2016 in Int'l Application No. PCT/EP2015/075516.

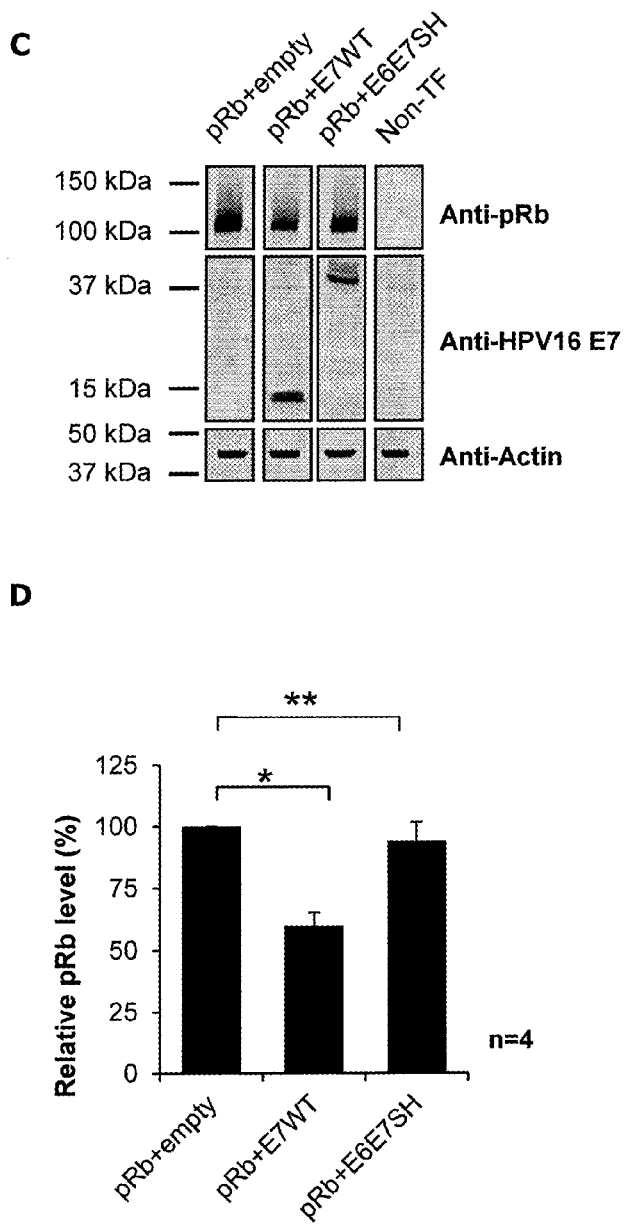
Fig. 3 - continued

A

B

A

B

F
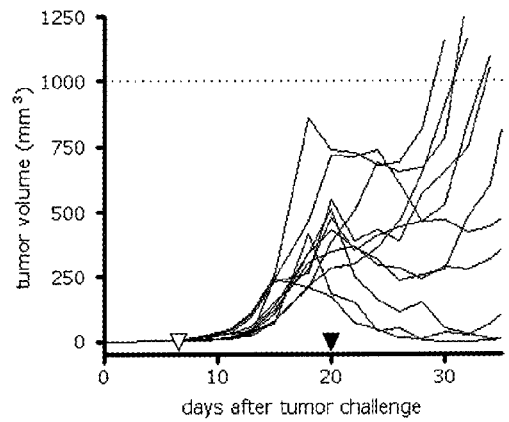
G
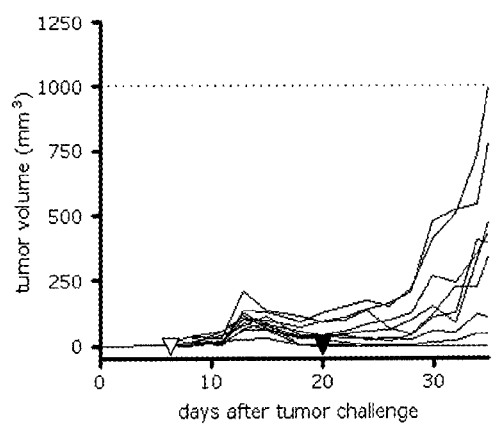
H
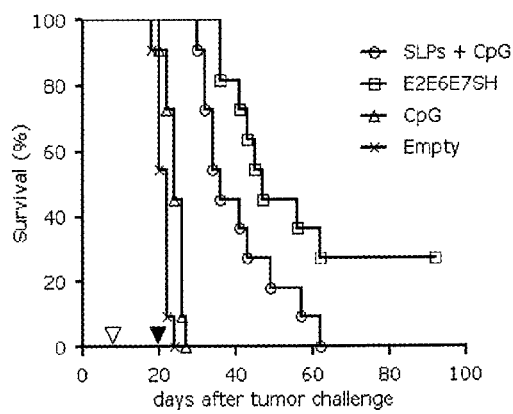
Fig. 12 - continued

A

B

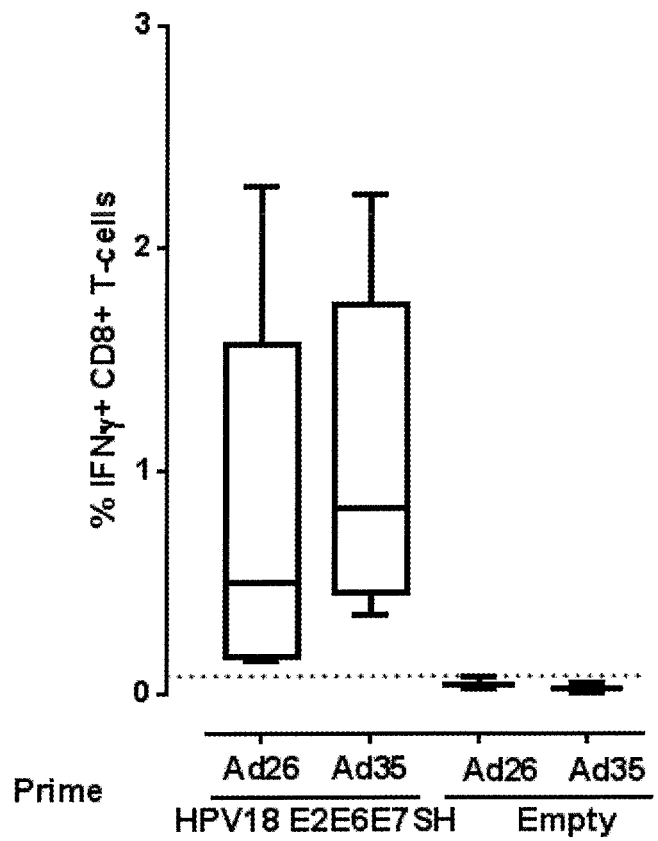
Fig. 19 - continued

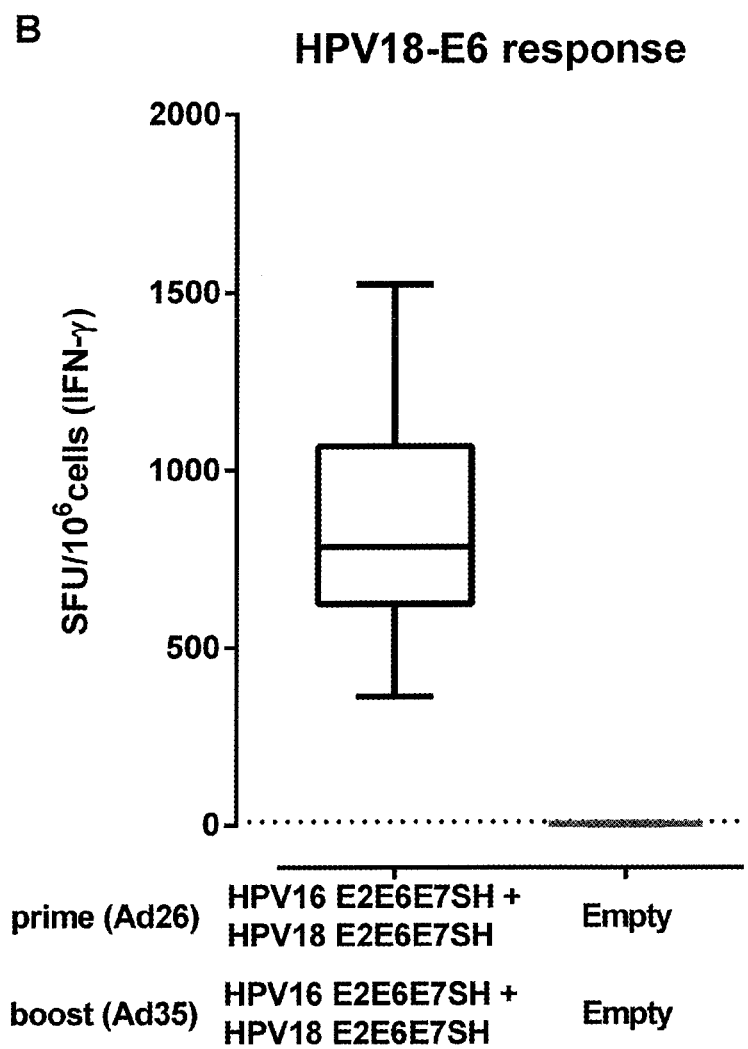
Fig. 20 – continued

THERAPEUTIC HPV18 VACCINES

TECHNICAL FIELD

The application relates to the field of medicine and more in particular to nucleic acid constructs and polypeptides that can be used in therapeutic vaccines against human papillomavirus type 18, and/or type 16.

STATEMENT ACCORDING TO 37 C.F.R. §1.821(c) OR (e)—SEQUENCE LISTING SUBMITTED AS A TXT FILE

Pursuant to 37 C.F.R. §1.821(c) or (e), a file containing a TXT version of the Sequence Listing has been submitted concomitant with this application, the contents of which are hereby incorporated by reference.

BACKGROUND

The family of human papillomaviruses (HPVs) consist of more than 100 types (also referred to as subtypes) that are capable of infecting keratinocytes of the skin or mucosal membranes. Over 40 types of HPV are typically transmitted through sexual contact and HPV infections of the anogenital region are very common in both men and women. Some sexually transmitted HPV types may cause genital warts. Persistent infections with "high-risk" HPV types (e.g. types 16, 18, 31, 45)—different from the ones that cause skin warts—may progress to precancerous lesions and invasive cancer, e.g. of the cervix, vulva, vagina, penis, oropharynx and anus. The majority of HPV infections are spontaneously cleared within one to two years after infection. In healthy individuals circulating Th1- and Th2-type CD4+ T-cells specific for the viral early proteins E2, E6 and E7 of HPV-16 as well as E6-specific CD8+ T-cells, migrate into the skin upon antigenic challenge, indicating that successful defense against HPV-16 infection is commonly associated with a systemic effector T-cell response against these viral early antigens. In a minority (~1%) of infected individuals, HPV infection persists, ultimately resulting in genital neoplastic lesions. Among the high-risk HPVs, HPV16 and HPV18 are the main cause of cervical cancer, together causing about 70% of the cases, and these two types also play a major role in other HPV-induced cancers such as anal and oropharyngeal cancer. Worldwide, HPV is one of the most important infectious agents causing cancer.

Vaccination against HPV is deemed a feasible strategy to reduce the incidence or effects of infection by HPV (van der Burg and Melief, 2011, *Curr Opinion Immunol* 23: 252-257).

Prophylactic HPV vaccines based on virus like particles (VLPs) formed by the (envelope) protein L1 of the HPV types 16 and 18, are very efficient in the prevention of persistent infection and the associated disease by HPV16 and HPV18. These vaccines are believed to provide sterile immunity via the induction of neutralizing antibodies against the L1 proteins. Addition of L1-based VLPs from additional high-risk HPV types may further increase the breadth of protection conferred by such vaccines.

However, while such vaccines can prevent initial infection (i.e., they result in prophylaxis), there is no evidence of a beneficial effect on established genital lesions caused by HPV16 and HPV18, so they are not considered therapeutic vaccines against HPV (Hildesheim et al., 2007, *JAMA* 298: 743-53).

Despite the introduction of these prophylactic vaccines, large numbers of people have already obtained or are still at risk of obtaining persistent high-risk HPV infections and, therefore, are at risk of getting cancer. Therapeutic vaccines for the eradication of established HPV infections and associated diseases are an urgent unmet medical need.

Some attempts to address this need have been described. For example, clinical trials have been carried out with a variety of different vaccination strategies, such as a fusion protein consisting of a heat shock protein (Hsp) from *Mycobacterium bovis* and HPV-16 E7 or consisting of a fusion protein of E6, E7 and L2 from HPV-16 and HPV-18, chimeric L1-E7 VLPs, recombinant vaccinia viruses expressing either E6 and E7 of HPV-16 and HPV-18 or bovine papilloma virus E2, DNA vaccines expressing CTL epitopes of E6 and E7 of HPV-16 and HPV-18, a live-attenuated *Listeria monocytogenes* (Lm) that secretes the HPV-16 E7 antigen, and synthetic long-peptides (SLPs) comprising HPV-16 E6 and E7 peptides. While some of these approaches show some, but limited, clinical efficacy, most have failed, demonstrating that improvement of the current strategies is needed.

Integration of the genes encoding the early HPV proteins E6 and E7 is a necessary step in the process from infection to cancer and continuous expression of E6 and E7 is required for the maintenance of the neoplastic phenotype of cervical cancer cells. E6 and E7 are therefore considered good targets for therapeutic vaccination. As mentioned some studies have shown that therapeutic vaccination of women infected with high-risk HPV can induce regression of existing lesions. Kenter et al showed a durable and complete regression in 47% of patients having Vulvar Intraepithelial Neoplasia (VIN) using SLPs derived from the HPV16 E6 and E7 proteins and an adjuvant as a therapeutic vaccine (Kenter et al., 2009, *N Engl J Med* 361: 1838-47). Similarly, a study in which a protein-based vaccine (TA-CIN, consisting of a fusion protein of HPV16 E6, E7 and L2) was combined with local immune modulation in VIN 2/3 patients, showed complete regression in 63% of patients (Daayana et al., 2010, *Br J Cancer* 102: 1129-36). Possible drawbacks of the synthetic long peptides as a vaccine include manufacturability at large scale and costs associated therewith, the need for potentially reactogenic adjuvant and the associated adverse effects associated with immunization (especially pain and swelling). Due to the high level of discomfort it is not likely that SLPs will be used in early stage disease when the spontaneous clearance rate is still high. Similarly, due to the need for local imiquimod treatment in the case of TA-CIN treatment, tolerability is a significant issue as the majority of women experience local and systemic side effects lasting for the duration of imiquimod treatment, which may affect daily activities.

A possible alternative is to use nucleic acid based vaccination such as DNA vaccines or viral vectored vaccines encoding the HPV E6 and/or E7 protein for vaccination.

However, the HPV E6 and E7 proteins have oncogenic potential and thus vaccination with vaccines that comprise nucleic acids encoding these proteins poses a risk of inducing cellular transformation due to the possibility of prolonged expression of the antigens.

Therefore, in case of genetic vaccination, non-oncogenic/ detoxified versions of E6 and/or E7 can be used in order to exclude any risk of cellular transformation due to the vaccination. Loss of oncogenic potential of wild-type E6 and E7 is commonly achieved by deletion and/or substitution of residues known to be important for the function of these proteins (e.g., Smahel et al., 2001, *Virology* 281:231-

38; Yan et al., 2009, *Vaccine* 27: 431-40; Wieking et al., 2012, *Cancer Gene Ther* 19: 667-74). However, a disadvantage of these approaches is that they carry the risk of removing important T-cell epitopes from and/or introducing new undesired T-cell epitopes into the proteins, and may thus not lead to the desired immune response.

In an alternative strategy to remove the oncogenic potential of HPV16 E6 and E7, shuffled versions (i.e., polypeptides wherein fragments of the wild-type protein are re-ordered) of the E6 and E7 proteins have been constructed (e.g. Öhlschläger et al., 2006, *Vaccine* 24: 2880-93; Oosterhuis et al., 2011, *Int J Cancer* 129: 397-406; Oosterhuis et al., 2012, *Hum Gen Ther* 23: 1301-12). However, these approaches would still require manufacturing, formulation and administration of multiple molecules to ensure inclusion of all possible epitopes of both the E6 and E7 proteins, resulting in sub-optimal logistics and relatively high costs, and moreover the strategies described introduce potentially strong non-natural epitopes that are not present in E6 and E7 and since immune responses could be diverted from relevant E6/E7 epitopes towards such non-natural epitopes, the described constructs may not have the optimal immunological characteristics. A therapeutic DNA vaccine expressing an intracellularly targeted fusion protein with built-in genetic adjuvant and shuffled fragments of E6 and E7 of both HPV16 and HPV18 has also been described, and electroporation-enhanced immunization therewith elicited a significant E6/E7-specific T-cell response in CIN3 patients (Kim et al., 2014).

Another approach that has been described to make immunogenic constructs is making so-called multi-epitope constructs or minigenes (e.g. US 2007/014810, the disclosure of which is incorporated herein by this reference; Mishra et al, 2014; Moise et al, 2011; Moss et al, 2010). This has the objective of generating the smallest peptide that encompasses the epitopes of interest. However, in such approaches potential disadvantages are that only a subset of the epitopes of a natural protein are present and further that typically spacer sequences are introduced that are not naturally present in the protein of interest.

BRIEF SUMMARY

Provided are nucleic acid molecules that encode polypeptides that comprise essentially all possible T-cell epitopes of HPV16 or HPV18 oncoproteins E6 and E7, but nevertheless have a strongly reduced (as compared to wt E6 and E7), up to non-detectable, transforming activity, by comprising fragments of the E6 and E7 proteins that have been re-ordered, while at the same time containing a minimized number of undesired strong neo-epitopes. This is in contrast to molecules previously reported by others. Provided is molecules that can be used in therapeutic vaccines against either HPV16 or HPV18. Such molecules can also be combined in therapeutic vaccines against both HPV16 and HPV18.

For HPV16, provided is a nucleic acid molecule encoding a polypeptide comprising a sequence as set forth in SEQ ID NO: 1 of the incorporated Sequence Listing. For HPV18, provided is a nucleic acid molecule encoding a polypeptide comprising an amino acid sequence as set forth in SEQ ID NO: 20.

The encoded polypeptide may further comprise a leader sequence.

In certain embodiments, the encoded polypeptide further comprises at least one epitope of a human papillomavirus (HPV) E2 protein, for example an HPV16 E2 protein or an HPV18 E2 protein. The E2 protein may be inactivated in for instance its transactivation and/or DNA binding domain, e.g. by deletion, mutation or by structural rearrangement of different parts of the protein. In certain embodiments for HPV16, the encoded polypeptide comprises a sequence as set forth in SEQ ID NO: 3 or SEQ ID NO: 5. In certain embodiments for HPV18, the encoded polypeptide comprises a sequence as set forth in SEQ ID NO: 22.

In certain embodiments, the nucleic acid sequence is codon-optimized, e.g. for expression in human cells.

In certain embodiments for HPV16, the nucleic acid sequence comprises a sequence as set forth in SEQ ID NO: 2, SEQ ID NO: 4, or SEQ ID NO: 6. In certain embodiments for HPV18, the nucleic acid sequence comprises a sequence as set forth in SEQ ID NO: 21 or SEQ ID NO: 23.

Also provided is a vector comprising a nucleic acid molecule of the disclosure, wherein the sequence encoding the polypeptide is operably linked to a promoter.

In certain embodiments, the vector is a DNA vector such as a plasmid. In other embodiments the vector is a viral vector, such as an MVA vector or a recombinant adenoviral vector. In certain preferred embodiments, the vector is a recombinant adenovirus.

In certain embodiments, the promoter in the vector is operably coupled to a repressor operator sequence, to which a repressor protein can bind in order to repress expression of the promoter in the presence of the repressor protein. In certain embodiments, the repressor operator sequence is a TetO sequence or a CuO sequence.

Also provided is a vaccine composition comprising a vector of the disclosure, and a pharmaceutically acceptable excipient.

Also provided is a method of inducing an immune response against HPV, in particular HPV16 or HPV18, or HPV16 and HPV18 in a subject, the method comprising administering to the subject a vaccine composition of the disclosure. Also provided is a vaccine of the disclosure for use in inducing an immune response against HPV, in particular HPV16 or HPV18, or both HPV16 and HPV18.

In certain embodiments, the vaccine is administered to the subject more than once.

Also provided is a method for treating any of: persistent HPV infection (in particular persistent HPV16 or HPV18 infection), vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC), oropharyngeal cancer, penile cancer, vaginal cancer or anal cancer in a subject, the method comprising administering to the subject a vaccine of the disclosure. Also provided is a vaccine of the disclosure for use in treatment of any of: persistent HPV infection (in particular persistent HPV16 or HPV18 infection), vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC), oropharyngeal cancer, penile cancer, vaginal cancer or anal cancer in a subject.

For HPV16, also provided is a polypeptide comprising a sequence as set forth in SEQ ID NO: 1, SEQ ID NO: 3 or SEQ ID NO: 5. The invention for HPV18 also provides a polypeptide comprising an amino acid sequence set forth in SEQ ID NO: 20 or SEQ ID NO: 22.

Also provided are combinations of molecules as described above for HPV16 and HPV18. Such molecules can be combined as separate molecules in a single composition (e.g. one nucleic acid for HPV16, i.e. encoding a polypeptide comprising an amino acid sequence as set forth in SEQ ID NO: 1, and one nucleic acid for HPV18, i.e. encoding a polypeptide comprising an amino acid comprising a sequence as set forth in SEQ ID NO: 20, for instance each on a separate vector). Alternatively, such molecules could be used in combination via administration to a single subject of at least two separate compositions (one for HPV16 and one for HPV18). Alternatively, such molecules could also be combined by having the HPV16 and HPV18 molecules present in a single nucleic acid molecule, e.g. a single vector. In certain embodiments therefore, provided is a vector of the disclosure, comprising both a nucleic acid molecule encoding a polypeptide that comprises the amino acid sequence set forth in SEQ ID NO: 1 and a nucleic acid molecule encoding a polypeptide that comprises the amino acid sequence set forth in SEQ ID NO: 20. In other embodiments, provided is a composition comprising a vector comprising a nucleic acid molecule encoding a polypeptide that comprises the amino acid sequence ("peptide") set forth in SEQ ID NO: 1 and a further vector comprising a nucleic acid molecule encoding a polypeptide that comprises the amino acid sequence set forth in SEQ ID NO: 20. In certain embodiments, provided is a method for inducing an immune response against HPV, in particular HPV16 and HPV18, in a subject, the method comprising administering to the subject a nucleic acid molecule encoding a polypeptide that comprises the amino acid sequence set forth in SEQ ID NO: 1 and a nucleic acid molecule encoding a polypeptide that comprises the amino acid sequence set forth in SEQ ID NO: 20. In certain embodiments, provided is a method for treating any of: persistent HPV infection (in particular persistent HPV16 or HPV18 infection), vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC), oropharyngeal cancer, penile cancer, vaginal cancer or anal cancer in a subject, the method comprising administering to the subject a nucleic acid molecule encoding a polypeptide that comprises the amino acid sequence set forth in SEQ ID NO: 1 and a nucleic acid molecule encoding a polypeptide that comprises the amino acid sequence set forth in SEQ ID NO: 20. In certain aspects of any of these HPV16/18 combination embodiments, the polypeptide that comprises the amino acid sequence set forth in SEQ ID NO: 1, may comprise a sequence as set forth in SEQ ID NO:3 or SEQ ID NO: 5, and optionally the nucleic acid sequence may comprise a sequence as set forth in SEQ ID NO: 2, SEQ ID NO: 4 or SEQ ID NO: 6, while the polypeptide that comprises the amino acid sequence set forth in SEQ ID NO: 20, may comprise a sequence as set forth in SEQ ID NO:22, and optionally the nucleic acid sequence may comprise a sequence as set forth in SEQ ID NO: 21 or SEQ ID NO: 23. Any of the features in embodiments described for the individual HPV16 or HPV18 nucleic acids, vectors, polypeptides, vaccine compositions, uses or methods above, can of course also be applied to the combinations of HPV16 and 18 as disclosed herein.

DETAILED DESCRIPTION

Figure 1:
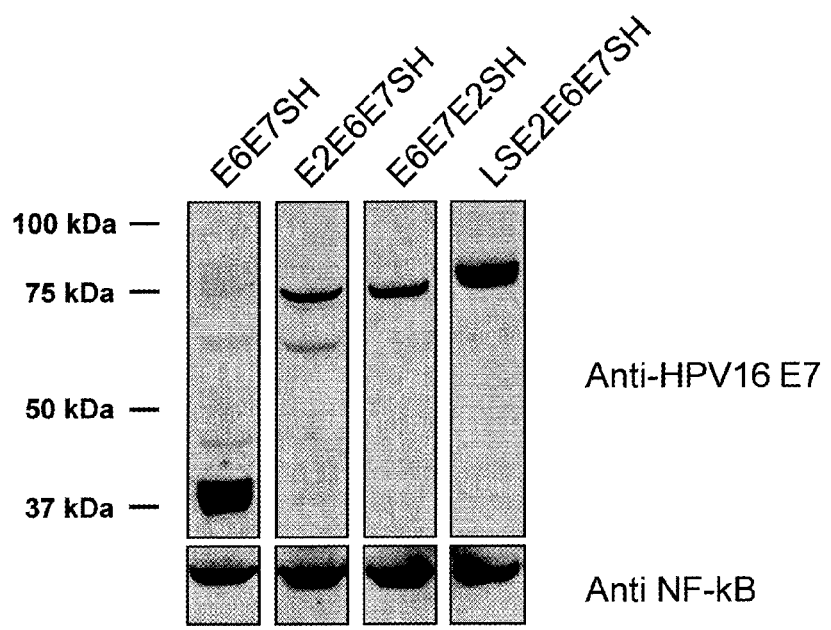
FIG. 1. Expression of fusion proteins of HPV16 E6 and E7. HEK-293T cells were transiently transfected with DNA vectors expressing the transgenes indicated above the figure. 24 hr after transfection the cells were harvested and cell extracts were analyzed by SDS-PAGE and western blotting with an antibody against HPV16 E7 (upper panel). A loading control showing NF-kB (lower panel) confirms similar loading of cell lysates in all lanes. A molecular weight marker is indicated on the left. Expected sizes of the fusion proteins: E6E7SH approx. 38 kDa; E2E6E7SH and E6E7E2SH approx. 75 kDa, LSE2E6E7SH approx. 78 kDa.

Provided is a nucleic acid molecule encoding a polypeptide comprising SEQ ID NO: 1. The polypeptide is a fusion polypeptide, and is sometimes referred to herein as the polypeptide of the disclosure, or the fusion polypeptide of the disclosure. This polypeptide is useful to generate an immune response against the E6 and E7 proteins of HPV16, and thus the nucleic acid molecule can be used as a therapeutic vaccine to prevent persistent HPV16 infection, and diseases associated therewith.

The polypeptide of the disclosure is a carefully designed molecule that contains virtually the complete E6 and E7 amino acid sequences of HPV16 (it lacks only one amino acid from the C-terminus of the native HPV16 E6 protein) in the form of fragments that are re-ordered and partly overlapping such that (essentially) all T-cell epitopes of the HPV16 E6 and E7 protein are present. Earlier molecules with some potential as HPV vaccines have been described by others (e.g. Kenter et al., 2009, *N Engl J Med* 361: 1838-47; Daayana et al., 2010, *Br J Cancer* 102: 1129-36; Smahel et al., 2001, *Virology* 281: 231-38; Yan et al., 2009, *Vaccine* 27: 431-40; Öhlschläger et al., 2006, *Vaccine* 24: 2880-93; Oosterhuis et al., 2011, *Int J Cancer* 129: 397-406; EP1183368, WO 2013/083287, the disclosure of each of which is incorporated herein by this reference), but each of these molecules has one or more drawbacks. The designer polypeptide molecules of the disclosure are advantageous in at least one and typically several aspects with respect to the approaches described earlier. In particular, advantages of the molecules and/or vectors of the disclosure include: (i) they have a desired safety profile, as the nucleic acid has a strongly reduced (as compared to native E6 and E7 proteins), down to non-detectable, transforming activity; (ii) they are single nucleic acid molecules, which are easy to manufacture at industrial scale in an economically feasible manner, and do not pose logistic challenges unlike multiple molecule approaches; (iii) the encoded polypeptides comprise essentially all T-cell epitopes of the native HPV16 E6 and E7 proteins; (iv) the design of the encoded polypeptides has minimized the introduction of undesired potential strong neo-epitopes (i.e. epitopes not present in the native E6 and E7 proteins); and (v) in certain embodiments, they are not dependent on highly reactogenic adjuvants to raise a desired immune response. Thus, the molecules of the disclosure represent a major step forward by combining various advantageous characteristics in a single design, and are excellent candidates primarily for therapeutic vaccination against HPV16. These molecules could also possibly work as prophylactic vaccines against HPV16, meaning that they are likely to prevent persistent infection with HPV16 of vaccinated subjects.

The benefits described in the previous two paragraphs for the nucleic acid molecule encoding HPV16 designer molecules (comprising an amino acid sequence set forth in SEQ ID NO: 1), also apply mutatis mutandis to nucleic acid molecules encoding novel designer molecules for HPV18 (comprising an amino acid sequence set forth in SEQ ID NO: 20).

IEDB-AR was used to determine the possible formation of non-natural strong epitopes that could be introduced at the newly created junctions between the different A6 and E7 fragments. In certain embodiments for the HPV16 designer molecule, by careful design the number of neo-epitopes with a length of nine amino acids with a predicted binding affinity <50 nM for the 20 most common HLA-A, 20 most common HLA-B and 20 most common HLA-C alleles in the re-ordered HPV16 E6 and E7 sequences was minimized to only 1. This is a significant improvement over constructs described by others, which for a single shuffled HPV16 E6 protein already contained more than 30 of such neo-epitopes, and which constructs will highly likely comprise even several more neo-epitopes in sequences that were appended to these constructs to prevent loss of epitopes (Öhlschläger et al., 2006, *Vaccine* 24: 2880-93). Hence the constructs of the invention have a significantly improved immunologic profile since chances of an altered immune response as compared to native E6 and E7 have been minimized in the molecules of the disclosure, as compared to approaches described by others.

Skilled persons may, using routine techniques, make nucleotide substitutions that do not affect the polypeptide sequence encoded by the polynucleotides described to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

In a preferred embodiment, the nucleic acid encoding the polypeptide of the disclosure is codon optimized for expression in mammalian cells, preferably human cells. Methods of codon-optimization are known and have been described previously (e.g. WO 96/09378, the disclosure of which is incorporated herein by this reference). A sequence is considered codon optimized if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in http://www.kazusa.or.jp/codon. Preferably more than one non-preferred codon, e.g. more than 10%, 40%, 60%, 80% of non-preferred codons, preferably most (e.g. at least 90%) or all non-preferred codons, are replaced by codons that are more preferred. Preferably the most frequently used codons in an organism are used in a codon-optimized sequence. Replacement by preferred codons generally leads to higher expression.

Nucleic acid sequences can be cloned using routine molecular biology techniques, or generated de novo by DNA synthesis, which can be performed using routine procedures by service companies having business in the field of DNA synthesis and/or molecular cloning (e.g. GeneArt, GenScripts, Invitrogen, Eurofins).

It will be appreciated by a skilled person that changes can be made to a protein, e.g. by amino acid substitutions, deletions, additions, etc., e.g. using routine molecular biology procedures. Generally, conservative amino acid substitutions may be applied without loss of function or immunogenicity of a polypeptide. This can be checked according to routine procedures well known to the skilled person.

In certain embodiments, the encoded polypeptide of the disclosure further comprises a leader sequence, also referred to as signal sequence or signal peptide. This is a short (typically 5-30 amino acids long) peptide present at the N-terminus of the majority of newly synthesized proteins that are destined towards the secretory pathway. The presence of such a sequence may lead to increased expression and immunogenicity. Non-limiting examples that can be used are an IgE leader peptide (see e.g. U.S. Pat. No. 6,733,994, the disclosure of which is incorporated herein by this reference; e.g. having sequence MDWTWIL-FLVAAATRVHS (SEQ ID NO: 7)) or a HAVT20 leader peptide (e.g. having sequence MACPGFLWALVIST- CLEFSMA (SEQ ID NO: 9)). One of these can optionally be added to the N-terminus of a polypeptide of the disclosure. In other embodiments, a polypeptide of the disclosure does not comprise a leader sequence.

Diverse types of HPV exist (over 120 types have been identified and are referred to by number), and generally for each type that needs to be covered by a vaccine, type-specific antigens may need to be incorporated in the vaccine, although for certain antigens some cross-reactivity might exist. Types 16, 18, 31, 33, 35, 39, 45, 51, 52, 56, 58, 59, 68, 73, and 82 are carcinogenic "high-risk" sexually transmitted HPVs and may lead to the development of cervical intraepithelial neoplasia (CIN), vulvar intraepithelial neoplasia (VIN), vaginal intraepithelial neoplasia (VaIN), penile intraepithelial neoplasia (PIN), and/or anal intraepithelial neoplasia (AIN). The HPV of the disclosure (i.e. the HPV from which the E6 and E7 fragments in the encoded polypeptide are derived) is HPV16 (for SEQ ID NOs: 1-6), or HPV18 (for SEQ ID NOs: 20-23). It can be used for subjects that are infected with HPV16 or HPV18, respectively. It may in certain embodiments also suitably be combined with vaccines against other HPV types. In certain embodiments, this combination is with a vaccine against HPV of a high risk type as identified above, e.g. a vaccine against HPV16 with a vaccine against HPV18. In other embodiments, the vaccine of the invention is combined with a vaccine against one or more of HPV-16, -18, -31, -33, -35, -39, -45, -51, -52, -56, -58, -59, -68, -73, or -82. Such combinations could for instance be used if the exact type of HPV infection is not yet certain, or if an immune response with a prophylactic effect is desired against more than one HPV type. Also combinations of the vaccines of the invention with vaccines against HPV types that cause genital warts, such as HPV6 and/or HPV11, are envisaged. Sequences of these HPV types and the proteins encoded thereby (e.g. E6, E7, E2) are available to the skilled person in public databases, such as the GenBank sequence database provided by the National Center for of technology Information (NCBI).

The polypeptide of the disclosure for HPV16 comprises SEQ ID NO: 1, and in one embodiment the nucleic acid molecule of the disclosure comprises SEQ ID NO: 2. The polypeptide of the disclosure for HPV18 comprises SEQ ID NO: 20, and in one embodiment the nucleic acid molecule of the disclosure comprises SEQ ID NO: 21.

Sequences herein are provided from 5' to 3' direction or from N- to C-terminus, as custom in the art.

The polypeptide of the disclosure comprises the epitopes of HPV16 E6 and E7 proteins, or alternatively the epitopes of HPV18 E6 and E7 proteins. In certain embodiments, the polypeptide of the disclosure further comprises (and hence the nucleic acid encoding the polypeptide further encodes) at least one further antigen or epitope(s) of such further antigen. Such a further antigen preferably is an HPV antigen, preferably of the same HPV type as the E6 and E7 proteins in the polypeptide, i.e. HPV16 or HPV18 respectively. Such a further antigen can thus be an HPV protein or an immunogenic fragment thereof, and in certain embodiments comprises an E2 protein or a fragment thereof comprising at least one epitope of E2 of HPV, preferably from HPV16 or HPV18. Such further antigens or epitopes could be placed internally between two fragments of E6 and/or E7 in the polypeptide comprising SEQ ID NO: 1 or SEQ ID NO: 20, but preferably are fused N-terminally or C-terminally to the E6/E7 polypeptide comprising SEQ ID NO: 1 or SEQ ID NO: 20. Alternatively or in addition, amino acid sequences can be present that stimulate the immune response. Thus, in certain embodiments provided is nucleic acid molecules of the disclosure, encoding a polypeptide comprising SEQ ID NO: 1 or SEQ ID NO: 20, and wherein the polypeptide further comprises at least one other antigen, e.g. HPV E2 protein or at least one epitope, but preferably more epitopes, thereof. One advantage of the addition of E2 antigen for the instant invention is that E2 is known to be expressed early during infection/in low grade lesions where E6 and E7 expression is still very low. During the development towards cervical cancer E2 expression is lost and as a result E6 and E7 levels are increased (Yugawa and Kiyono, 2009, *Rev Med Virol* 19: 97-113). Combining epitopes from E2, E6 and E7 in one vaccine allows for treatment in a broad target group of patients, ranging from having persistent infection to invasive cervical cancer (or other HPV16-caused cancers). In certain embodiments, the E2 protein is a wild-type E2 protein. In certain other embodiments, the E2 protein has a deletion or one or more mutations in its DNA binding domain (as compared to a wild type E2 protein). The sequence of the HPV16 and HPV18 E2 proteins can be found in the NCBI protein database (www.ncbi.nlm.nih.gov/protein) under numbers NP 041328.1 and AAP20597.1, respectively. Several single amino acid changes in HPV16 E2 such as G293V, K299M, or C300R in the C-terminal part of this protein are known to abrogate DNA binding. For HPV18 E2, the corresponding amino acid changes are G294V, K300M, C301R. An advantage of using a variant or fragment of E2 that lacks DNA binding capacity is that it could prevent unpredictable transcriptional changes via direct binding to host cell DNA in the cells where it is expressed. In addition to or as an alternative to mutations in the DNA binding domain described above, further approaches to prevent E2 activity are to introduce mutations that abrogate activity of the more N-terminally located E2 transactivation domain, and/or that are reported to affect the structure of the E2 polypeptide. For HPV16 E2, non-limiting examples of amino acid changes at positions that have previously been described (e.g. Brokaw et al, 1996; Sakai et al, 1996) are R37A, I73A, W92A, E39A, W33A, P106A and G156A, and HPV16 E2 of the disclosure could optionally comprise one or more of these mutations in the transactivation domain. For HPV 18 E2, the corresponding amino acid changes are R41A, I77A, W96A, E43A, W37A, P110A and G161A, and HPV18 E2 of the disclosure could thus optionally comprise one or more of these mutations in the transactivation domain. In certain embodiments, E2 has mutations in the transactivation domain, in other embodiments E2 has mutations in the DNA binding domain, and in further embodiments E2 has mutations in both the transactivation domain and in the DNA binding domain. In yet another alternative embodiment, the E2 polypeptide of the disclosure is divided in fragments which are reordered (shuffled), to abrogate E2 activity while maintaining the E2 epitopes for immunogenicity. Such embodiment could optionally be combined with one or more of the mutations described above, e.g. in the DNA binding domain and/or in the transactivation domain. Besides wild-type HPV E2 polypeptides, all such E2 mutants can be used as the E2 protein or part or variant thereof of the disclosure.

The E2 protein or part or variant thereof can be added internally, but preferably is fused to the N-terminus or to the C-terminus of the polypeptide of the disclosure having SEQ ID NO: 1 or SEQ ID NO: 20. In one embodiment for HPV16, the nucleic acid molecule of the invention encodes a polypeptide comprising SEQ ID NO: 3. In one embodiment thereof, the nucleic acid molecule of the invention comprises SEQ ID NO: 4. In another embodiment for HPV16, the nucleic acid molecule of the invention encodes a polypeptide comprising SEQ ID NO: 5. In one embodiment thereof, the nucleic acid molecule of the invention comprises SEQ ID NO: 6. In one embodiment for HPV18, the nucleic acid molecule of the invention encodes a polypeptide comprising SEQ ID NO: 22. In one embodiment thereof, the nucleic acid molecule of the invention comprises SEQ ID NO: 23.

It is also possible to make further fusions of the designer polypeptides of the invention with further proteins, e.g. so called carrier proteins, such as Calreticulin, *Mycobacterium Tuberculosis* heat shock protein-70, IP10, or Tetanus toxin fragment C (see Oosterhuis et al., *Human Gene Ther*, 2012, supra, for more examples), which could further enhance the immune response to the HPV E6 and E7 (and optionally E2) epitopes. The invention thus also provides such further fusion proteins, and nucleic acids encoding such.

In certain embodiments, a nucleic acid molecule of the disclosure is incorporated into a vector. A "vector" as used herein, is typically a vehicle to artificially carry foreign genetic material into another cell, where it can be replicated and/or expressed, and of the disclosure can be any nucleic acid molecule that incorporates a nucleic acid molecule of the disclosure. These can be prepared according to routine molecular biology techniques such as cloning. Typically such vectors can be propagated in at least one type of suitable hosts such as bacteria, yeast, insect cells, mammalian cells, and the like. Four major types of vectors are plasmids, viral vectors, cosmids, and artificial chromosomes. The vector itself is generally a DNA sequence that consists of an insert (transgene; in the disclosure the nucleic acid encoding the fusion polypeptide of the disclosure) and a sequence that serves as the "backbone" of the vector. The purpose of a vector which transfers genetic information to another cell is typically to isolate, multiply, or express the insert in the target cell. Preferably, the sequence encoding the polypeptide is operably linked to a promoter in the vector. The term "operably linked" is intended to mean that the nucleotide sequence of interest is linked to the promoter in a manner that allows for expression of the nucleotide sequence (e.g., in a host cell when the vector is introduced into the host cell). Expression regulatory sequences can be operably linked to a transgene. In certain embodiments, vectors are designed for the expression of the transgene in the target cell, and generally have a promoter sequence that drives expression of the transgene. In certain embodiments, one or more of routinely used vector elements such as transcription terminator sequences, polyadenylation tail sequences, Kozak sequences, UTRs, origin of replication, multiple cloning sites, genetic markers, antibiotic resistance, and further sequences may be present, and the skilled person can design a vector such that it has the desired properties, e.g. for replication in certain cells for propagation and multiplication of the vector, and for expression of the transgene of the vector in target cells into which the vector is introduced. Vectors comprising the nucleic acid encoding the fusion polypeptide of the disclosure, preferably designed for expression in mammalian cells, are suitable as vaccines of the disclosure. In certain embodiments, a vector of the disclosure is a plasmid, a cosmid, a yeast artificial chromosome, a bacterial artificial chromosome, a viral vector, or the like. The person skilled in the art is aware that various promoters can be used to obtain expression of a gene in host cells. Some well-known and much used promoters for expression in eukaryotic cells comprise promoters derived from viruses, such as adenovirus, e.g. the E1A promoter, promoters derived from cytomegalovirus (CMV), such as the CMV immediate early (IE) promoter (referred to herein as the CMV promoter) (obtainable for instance from pcDNA, Invitrogen), promoters derived from Simian Virus 40 (SV40) (e.g. obtainable from pIRES, cat. no. 631605, BD Sciences), and the like. Suitable promoters can also be derived from eukaryotic cells, such as methallothionein (MT) promoters, elongation factor 1α (EF-1α) promoter, ubiquitin C or UB6 promoter, actin promoter, an immunoglobulin promoter, heat shock promoters, and the like (see e.g. WO 2006/048459, the disclosure of which is incorporated herein by this reference). A non-limiting example of a suitable promoter for obtaining expression in eukaryotic cells is a CMV-promoter (U.S. Pat. No. 5,385,839, the disclosure of which is incorporated herein by this reference), e.g. the CMV immediate early promoter, for instance comprising nt. −735 to +95 from the CMV immediate early gene enhancer/promoter, e.g. a CMV promoter as provided herein with a sequence as set forth in SEQ ID NO: 13. A polyadenylation signal, for example the bovine growth hormone polyA signal (U.S. Pat. No. 5,122,458, the disclosure of which is incorporated herein by this reference), may be present behind the transgene(s).

Further regulatory sequences may also be added. The term "regulatory sequence" is used interchangeably with "regulatory element" herein and refers to a segment of nucleic acid, typically but not limited to DNA, that modulate the transcription of the nucleic acid sequence to which it is operatively linked, and thus acts as a transcriptional modulator. A regulatory sequence often comprises nucleic acid sequences that are transcription binding domains that are recognized by the nucleic acid-binding domains of transcriptional proteins and/or transcription factors, enhancers or repressors etc. For example, it is possible to operably couple a repressor sequence to the promoter, which repressor sequence can be bound by a repressor protein that can decrease or prevent the expression of the transgene in a production cell line that expresses this repressor protein. This may improve genetic stability and/or expression levels of the nucleic acid molecule upon passaging and/or when this is produced at high quantities in the production cell line. Such systems have been described in the art. For example, a regulatory sequence could include one or more tetracycline operon operator sequences (tetO), such that expression is inhibited in the presence of the tetracycline operon repressor protein (tetR). In the absence of tetracycline, the tetR protein is able to bind to the tetO sites and repress transcription of a gene operably linked to the tetO sites. In the presence of tetracycline, however, a conformational change in the tetR protein prevents it from binding to the operator sequences, allowing transcription of operably linked genes to occur. In certain embodiments, a nucleic acid molecule, e.g. when present in a recombinant adenovirus vector, of the disclosure can optionally include tetO operatively linked to a promoter, such that expression of one or more transgenes is inhibited in recombinant adenoviruses that are produced in the producer cell line in which tetR protein is expressed. Subsequently, expression would not be inhibited if the recombinant adenovirus is introduced into a subject or into cells that do not express the tetR protein (e.g., international patent application WO 07/073513). In certain other embodiments, a nucleic acid molecule of the disclosure, e.g. when present in a recombinant adenovirus, can optionally include a cumate gene-switch system, in which regulation of expression is mediated by the binding of the repressor (CymR) to the operator site (CuO), placed downstream of the promoter (e.g., Mullick et al. *BMC Biotechnol.* 2006 6:43). As used herein, the term "repressor," refers to entities (e.g., proteins or other molecules) having the capacity to inhibit, interfere, retard and/or repress the production of heterologous protein product of a recombinant expression vector. For example, by interfering with a binding site at an appropriate location along the expression vector, such as in an expression cassette. Examples of repressors include tetR, CymR, the lac repressor, the trp repressor, the gal repressor, the lambda repressor, and other appropriate repressors known in the art. Examples of the use of the tetO/tetR operator/repressor system and of the CuO/CymR operator/repressor system are provided herein. Repression of vector transgene expression during vector propagation can prevent transgene instability, and may increase yields of vectors having a transgene of the invention during production. Hence, in some embodiments, the vectors of the invention have a promoter that can be repressed by binding of a repressor protein, e.g. by having a promoter that is operably coupled to a repressor operator sequence (e.g. in non-limiting embodiments, a TetO-containing sequence, e.g. the one set forth in SEQ ID NO: 11, or a CuO-containing sequence, e.g. the one set forth in SEQ ID NO: 12), to which a repressor protein (e.g. the TetR protein, e.g. having an amino acid sequence as set forth in SEQ ID NO: 15, or the CymR protein, e.g. having an amino acid sequence as set forth in SEQ ID NO: 17) can bind.

In certain embodiments, the vector is a plasmid DNA molecule, or a fragment thereof. These can be used for DNA vaccination. Other platforms are also possible for use as vectors, for instance live-attenuated double-deleted *Listeria monocytogenes* strains.

In other embodiments, the vector is a recombinant viral vector, which may be replication competent or replication deficient. In certain embodiments, a viral vector comprises a recombinant DNA genome. In certain embodiments, a vector of the disclosure is for instance a recombinant adenovirus, a recombinant retrovirus, a recombinant pox virus such as a vaccinia virus (e.g. Modified Vaccinia Ankara (MVA)), a recombinant alphavirus such as Semliki forest virus, a recombinant paramyxovirus, such as a recombinant measles virus, or another recombinant virus. In certain embodiments, a vector of the disclosure is an MVA vector.

In preferred embodiments, a vector of the disclosure is a recombinant adenovirus. Advantages of adenoviruses for use as vaccines include ease of manipulation, good manufacturability at large scale, and an excellent safety record based on many years of experience in research, development, manufacturing and clinical trials with numerous adenoviral vectors that have been reported. Adenoviral vectors that are used as vaccines generally provide a good immune response to the transgene-encoded protein, including a cellular immune response. An adenoviral vector of the disclosure can be based on any type of adenovirus, and in certain embodiments is a human adenovirus, which can be of any serotype. In other embodiments, it is a simian adenovirus, such as chimpanzee or gorilla adenovirus, which can be of any serotype. In certain embodiments, a vector of the disclosure is of a human adenovirus serotype 5, 26 or 35. The preparation of recombinant adenoviral vectors is well known in the art. In certain embodiments, an adenoviral vector of the disclosure is deficient in at least one essential gene function of the E1 region, e.g. the E1a region and/or the E1b region, of the adenoviral genome that is required for viral replication. In certain embodiments, an adenoviral vector of the disclosure is deficient in at least part of the non-essential E3 region. In certain embodiments, the vector is deficient in at least one essential gene function of the E1 region and at least part of the non-essential E3 region.

Adenoviral vectors, methods for construction thereof and methods for propagating thereof, are well known in the art and are described in, for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication", M. S. Horwitz, "Adenoviruses", Chapters 67 and 68, respectively, in *Virology*, B. N. Fields et al., eds., 3d ed., Raven Press, Ltd., New York (1996), and other references mentioned herein. Typically, construction of adenoviral vectors involves the use of standard molecular biological techniques, such as those described in, for example, Sambrook et al., *Molecular Cloning, a Laboratory Manual*, 2d ed., Cold Spring Harbor Press, Cold Spring Harbor, N.Y. (1989), Watson et al., Recombinant DNA, 2d ed., Scientific American Books (1992), and Ausubel et al., *Current Protocols in Molecular Biology*, Wiley Interscience Publishers, NY (1995), and other references mentioned herein.

Figure 6:
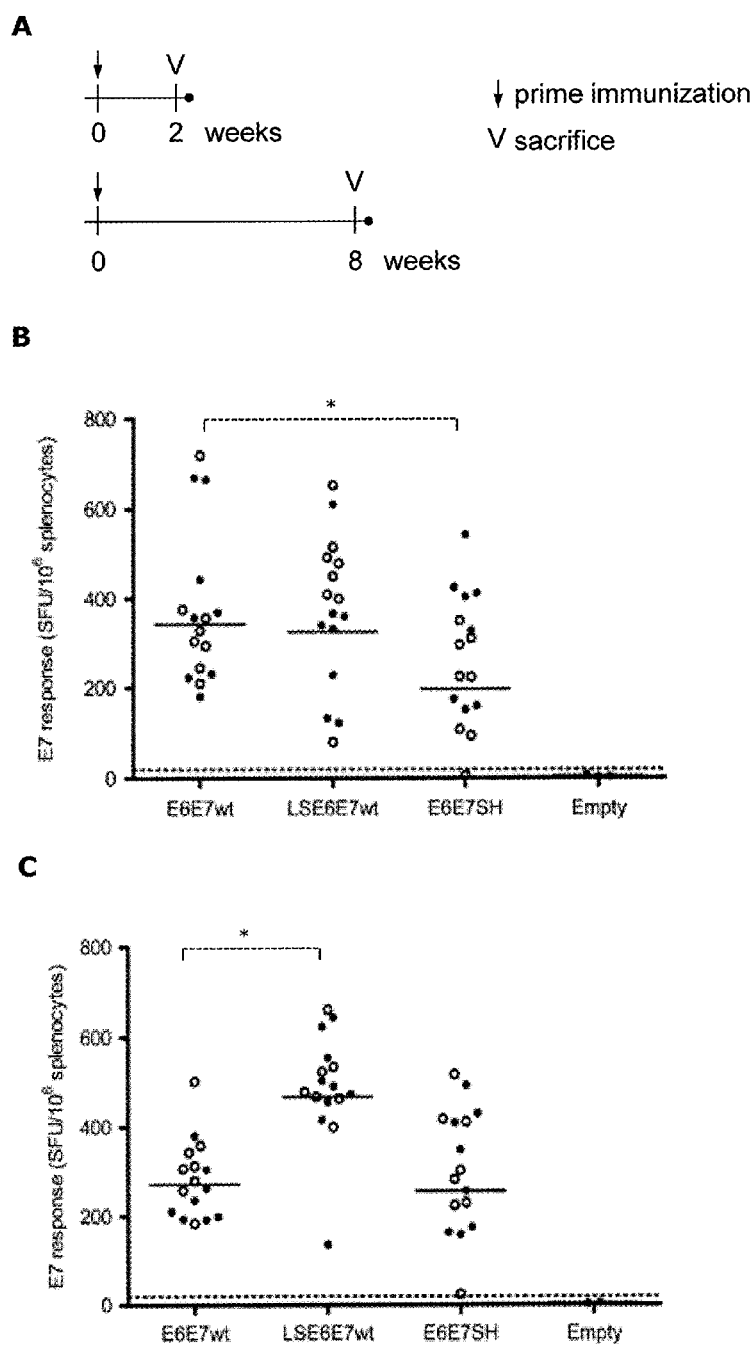
FIG. 6. Immunogenicity of HPV16 E6E7SH—IFNγ ELISPOT analysis. (A). Immunization scheme. Mice were immunized with adenovectors with inserts as indicated. E7-specific responses at two weeks (B) and at eight weeks (C) were analyzed by IFNγ ELISPOT (represented as spot-forming units (SFU) per $10^6$ splenocytes). The closed circles represent mice immunized with a dosage of $1*10^{10}$ vp, and open circles represent mice immunized with $5*10^9$ vp. The black bar represents the geometric mean of the responses. The dotted line indicates the lower detection limit in the ELISPOT assay. ANOVA Post-hoc Bonferroni statistical analysis was performed on log transformed data. *: p<0.05. For details see example 3.

Particularly preferred serotypes for the recombinant adenovirus are human serotype 35 or human serotype 26. Preparation of rAd26 vectors is described, for example, in WO 2007/104792 and in Abbink et al., 2007 *Virology* 81: 4654-63. Exemplary genome sequences of Ad26 are found in GenBank Accession EF 153474 and in SEQ ID NO:1 of WO 2007/104792. Preparation of rAd35 vectors is described, for example, in U.S. Pat. No. 7,270,811, in WO 00/70071, and in Vogels et al., 2003, *J Virol* 77: 8263-71, the disclosure of each of which is incorporated herein by this reference. Exemplary genome sequences of Ad35 are found in GenBank Accession AC 000019 and in FIG. 6 of WO 00/70071.

In certain embodiments, the adenovirus is replication deficient, e.g. because it contains a deletion in the E1 region of the genome. As known to the skilled person, in case of deletions of essential regions from the adenovirus genome, the functions encoded by these regions have to be provided in trans, preferably by the producer cell, i.e. when parts or whole of E1, E2 and/or E4 regions are deleted from the adenovirus, these have to be present in the producer cell, for instance integrated in the genome thereof, or in the form of so-called helper adenovirus or helper plasmids. The adenovirus may also have a deletion in the E3 region, which is dispensable for replication, and hence such a deletion does not have to be complemented.

A producer cell (sometimes also referred to in the art and herein as 'packaging cell' or 'complementing cell') that can be used can be any producer cell wherein a desired adenovirus can be propagated. For example, the propagation of recombinant adenovirus vectors is done in producer cells that complement deficiencies in the adenovirus. Such producer cells preferably have in their genome at least an adenovirus E1 sequence, and thereby are capable of complementing recombinant adenoviruses with a deletion in the E1 region. Any E1-complementing producer cell can be used, such as human retina cells immortalized by E1, e.g. 911 or PER.C6 cells (see U.S. Pat. No. 5,994,128, the disclosure of which is incorporated herein by this reference), E1-transformed amniocytes (See EP patent 1230354), E1-transformed A549 cells (see e.g. WO 98/39411 and U.S. Pat. No. 5,891,690, the disclosure of each of which is incorporated herein by this reference), GH329:HeLa (Gao et al., 2000, *Hum Gene Ther* 11: 213-19), 293, and the like. In certain embodiments, the producer cells are for instance HEK293 cells, or PER.C6 cells, or 911 cells, or IT293SF cells, and the like. Production of adenoviral vectors in producer cells is reviewed in (Kovesdi et al., 2010, *Viruses* 2: 1681-703).

In certain embodiments, an E1-deficient adenovirus comprises the E4-orf6 coding sequence of an adenovirus of subgroup C such as Ad5. This allows propagation of such adenoviruses in well-known complementing cell lines that express the E1 genes of Ad5, such as for example 293 cells or PER.C6 cells (see, e.g. Havenga et al., 2006, *J Gen Virol* 87: 2135-43; WO 03/104467, incorporated in its entirety by reference herein).

"Heterologous nucleic acid" (also referred to herein as 'transgene') in vectors of the invention is nucleic acid that is not naturally present in the vector, and according to the disclosure the nucleic acid encoding the fusion polypeptide of the disclosure is considered heterologous nucleic acid when present in a vector. It is introduced into the vector for instance by standard molecular biology techniques. It can for instance be cloned into a deleted E1 or E3 region of an adenoviral vector, or in the region between the E4 region and the rITR. A transgene is generally operably linked to expression control sequences. In preferred embodiments, the transgene is cloned into the E1-region of an adenoviral vector.

Production of vectors such as DNA vectors, MVA vectors, or recombinant adenovirus vectors, can be performed according to various methods well known to the person skilled in the art. Generally, the production entails propagation in cultured cells to generate a substantial amount of vector material, followed by harvest of the vector from the cell culture, and typically followed by further purification of the vector to remove other substances and obtain purified vectors that can be formulated into pharmaceutical compositions (e.g., Hoganson et al., 2002, *BioProcessing J* 1: 43-8; Evans et al., 2004, *J Pharm Sci* 93:2458-75). For example, methods for harvesting adenovirus from cultures of producer cells have for instance been extensively described in WO 2005/080556. For example WO 2010/060719, and WO 2011/098592, both incorporated by reference herein, describe suitable methods for obtaining and purifying large amounts of recombinant adenoviruses.

In certain aspects, also provided is a polypeptide that is encoded by a nucleic acid molecule of the disclosure. Such a polypeptide comprises SEQ ID NO: 1 (for HPV16), or SEQ ID NO: 20 (for HPV18). In certain embodiments, such a polypeptide may comprise SEQ ID NO: 3 or SEQ ID NO: 5 (each for HPV16), or SEQ ID NO: 22 (for HPV18). The characteristics of such a polypeptide are as described above. Such a polypeptide can for instance be used directly as a vaccine against HPV.

The invention further provides vaccines comprising nucleic acid molecules, vectors or polypeptides of the disclosure, wherein embodiments for each of these aspects can include those as described above. In preferred embodiments, a vaccine of the disclosure comprises a nucleic acid molecule of the disclosure. In further preferred embodiments, the vaccine comprises a vector of the disclosure, preferably a DNA vector, an MVA vector, or a recombinant adenovirus vector.

In certain embodiments, a vaccine of the disclosure that encodes the HPV16 designer polypeptide comprises further active ingredients, e.g. nucleic acid encoding at least one epitope of E6 and/or E7 protein of at least one HPV type different from HPV16, e.g. a high risk HPV type such as HPV18, -31, -33, -35, -39, -45, -51, -52, -56, -58, -59, -68, -73, or -82. In certain embodiments, a vaccine of the disclosure that encodes the HPV18 designer polypeptide comprises further active ingredients, e.g. nucleic acid encoding at least one epitope of E6 and/or E7 protein of at least one HPV type different from HPV18, e.g. a high risk HPV type such as HPV16, -31, -33, -35, -39, -45, -51, -52, -56, -58, -59, -68, -73, or -82.

Particularly preferred are vaccines comprising nucleic acids encoding both HPV16 and HPV18 designer polypeptides of the invention, i.e. encoding a polypeptide with SEQ ID NO: 1 as well as a polypeptide with SEQ ID NO: 20. In such vaccines, the HPV16 and HPV18 components may be in the same composition as separate molecules, or they may be in the same molecule, e.g. encoded on the same vector, or they could be provided as a kit of parts with a separate HPV16 component and a separate HPV18 component for combined use in vaccination, e.g. for reconstitution prior to administration, or for separate but essentially simultaneous administration. One advantage of such combinations is that such vaccines can work therapeutically in subjects that are infected with either HPV16 or with HPV18 (the two most prevailing high risk HPV types that together account for the majority of HPV-induced cancers), so that such vaccines have increased applicability over the monotype vaccines that have either HPV16 or HPV18 designer molecules.

The term "vaccine" refers to an agent or composition containing an active component effective to induce a prophylactic and/or therapeutic degree of immunity in a subject against a certain pathogen or disease, in this case therapeutically against HPV. The vaccine typically comprises the nucleic acid molecule, or vector, of the disclosure, and a pharmaceutically acceptable excipient. Upon administration to a subject, the polypeptide encoded by the nucleic acid molecule of the disclosure will be expressed in the subject, which will lead to an immune response towards E6 and/or E7 antigenic fragments that are present in the polypeptide. The advantage of the instant molecules is that essentially all T-cell epitopes of HPV16 (for SEQ ID NOs: 1-6) or HPV18 (for SEQ ID NOs: 20-23) E6 and E7 are present and thus a T-cell response to any epitope present in wild-type E6 or E7 can be mounted in the vaccine. Further, the vaccine has all the safety and efficacy advantages as outlined above for the nucleic acid molecules of the disclosure.

For administering to humans, the invention may employ pharmaceutical compositions comprising the vector and a pharmaceutically acceptable carrier or excipient. In the present context, the term "Pharmaceutically acceptable" means that the carrier or excipient, at the dosages and concentrations employed, will not cause any unwanted or harmful effects in the subjects to which they are administered. Such pharmaceutically acceptable excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). An excipient is generally a pharmacologically inactive substance formulated with the active ingredient of a medication. Excipients are commonly used to bulk up formulations that contain potent active ingredients (thus often referred to as "bulking agents," "fillers," or "diluents"), to allow convenient and accurate dispensation of a drug substance when producing a dosage form. They also can serve various therapeutic-enhancing purposes, such as facilitating drug absorption or solubility, or other pharmacokinetic considerations. Excipients can also be useful in the manufacturing process, to aid in the handling of the active substance concerned such as by facilitating powder flowability or non-stick properties, in addition to aiding in vitro stability such as prevention of denaturation over the expected shelf life. The selection of appropriate excipients also depends upon the route of administration and the dosage form, as well as the active ingredient and other factors.

The purified nucleic acid molecule, vector or polypeptide preferably is formulated and administered as a sterile solution although it is also possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5. The nucleic acid molecule or vector or polypeptide typically is in a solution having a suitable buffer, and the solution of vector may also contain a salt. Optionally stabilizing agent may be present, such as albumin. In certain embodiments, detergent is added. In certain embodiments, vaccine may be formulated into an injectable preparation. These formulations contain effective amounts of nucleic acid molecule, vector or polypeptide are either sterile liquid solutions, liquid suspensions or lyophilized versions and optionally contain stabilizers or excipients.

For instance recombinant adenovirus vector may be stored in the buffer that is also used for the Adenovirus World Standard (Hoganson et al., 2002, *Bioprocessing J* 1: 43-8): 20 mM Tris pH 8, 25 mM NaCl, 2.5% glycerol. Another useful formulation buffer suitable for administration to humans is 20 mM Tris, 2 mM $MgCl_2$, 25 mM NaCl, sucrose 10% w/v, polysorbate-80 0.02% w/v. Another formulation buffer that is suitable for recombinant adenovirus comprises 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Obviously, many other buffers can be used, and several examples of suitable formulations for the storage and for pharmaceutical administration of purified vectors are known.

In certain embodiments a composition comprising the vector further comprises one or more adjuvants. Adjuvants are known in the art to further increase the immune response to an applied antigenic determinant. The terms "adjuvant" and "immune stimulant" are used interchangeably herein, and are defined as one or more substances that cause stimulation of the immune system. In this context, an adjuvant is used to enhance an immune response to the polypeptides encoded by the nucleic acid molecules in the vectors of the invention. Examples of suitable adjuvants include aluminium salts such as aluminium hydroxide and/or aluminium phosphate and/or aluminium potassium phosphate; oil-emulsion compositions (or oil-in-water compositions), including squalene-water emulsions, such as MF59 (see e.g. WO 90/14837, the disclosure of which is incorporated herein by this reference); saponin formulations, such as for example QS21 and Immunostimulating Complexes (ISCOMS) (see e.g. U.S. Pat. No. 5,057,540; WO 90/03184, WO 96/11711, WO 2004/004762, and WO 2005/002620, the disclosure of each of which is incorporated herein by this reference); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like. It is also possible to use vector-encoded adjuvant, e.g. by using heterologous nucleic acid that encodes a fusion of the oligomerization domain of C4-binding protein (C4 bp) to the antigen of interest (e.g. Solabomi et al., 2008, *Infect Immun* 76: 3817-23), or by using a vector encoding both the transgene of interest and a TLR-3 agonist such as heterologous dsRNA (e.g. WO 2007/100908, the disclosure of which is incorporated herein by this reference), or the like.

In other embodiments, the compositions of the invention do not comprise adjuvants.

Pharmaceutical compositions may be administered to a subject, e.g. a human subject. The total dose of the vaccine active component provided to a subject during one administration can be varied as is known to the skilled practitioner, and for adenovirus is generally between $1\times10^7$ viral particles (vp) and $1\times10^{12}$ vp, preferably between $1\times10^8$ vp and $1\times10^{-11}$ vp, for instance between $3\times10^8$ and $5\times10^{10}$ vp, for instance between $10^9$ and $3\times10^{10}$ vp. For a DNA vaccine, total amounts of DNA per administration may for instance be between 1 µg and 10 mg. If a gene gun is used for administration, typically low amounts are used, e.g. 10 µg. For intramuscular injection, typically higher amounts are used, e.g. up to 5 mg.

Administration of pharmaceutical compositions can be performed using standard routes of administration. Non-limiting embodiments include parenteral administration, such as by injection, e.g. intradermal, intramuscular, etc., or subcutaneous or transcutaneous, or mucosal administration, e.g. intranasal, oral, intravaginal, rectal, and the like. In one embodiment a composition is administered by intramuscular injection, e.g. into the deltoid muscle of the arm, or vastus lateralis muscle of the thigh. In certain embodiments the vaccine is a DNA vaccine, and this can for instance be administered intradermally, e.g. by DNA tattooing (see, e.g. Oosterhuis et al., 2012, *Curr Top Microbiol Immunol* 351: 221-50). This route is also feasible for adenoviral vectors. In certain embodiments a composition of the disclosure comprises an adenoviral vector and is administered by intramuscular injection. The skilled person knows the various possibilities to administer a composition, such as a vaccine in order to induce an immune response to the antigen(s) in the vaccine.

A subject as used herein preferably is a mammal, for instance a rodent, e.g. a mouse, or anon-human-primate, or a human. Preferably, the subject is a human subject.

The vaccines of the invention can be used to treat patients having one of various stages of diseases caused by HPV (in particular type 16 for vaccines comprising or encoding any of SEQ ID NOs: 1-6, or type 18 for vaccines comprising or encoding any of SEQ ID NOs: 20-23, or both types for vaccines that comprise or encode both HPV16 and HPV18 designer molecules described herein), from incident and persistent HPV infection as such (e.g. as detected by HPV DNA testing), thus before (pre-)cancerous lesions are formed, as well as cervical intraepithelial neoplasia (CIN; also known as cervical dysplasia and cervical interstitial neoplasia, which is the potentially premalignant transformation and abnormal growth (dysplasia) of squamous cells on the surface of the cervix) up to and including cervical cancer (such as cervical squamous cell carcinoma (SCC). In addition, other HPV-induced neoplasias, such as vulvar intraepithelial neoplasia (VIN), vaginal intraepithelial neoplasia (VaIN), penile intraepithelial neoplasia (PIN), anal intraepithelial neoplasia (AIN) can be targeted as well as more advanced stages of oropharyngeal cancer (also known as head- and neck cancer), penile cancer, vaginal cancer, vulvar cancer and anal cancer. The vaccines of the invention thus can target a wide range of HPV induced lesions, and are likely most effective at the precancerous stages of HPV-induced disease, e.g. at the (persistent) infection and/or the neoplasia stages, where expression of E2, E6 and/or E7 is highest. It is also possible to combine the treatment using a vaccine of the invention with compounds that counteract or can overcome immune escape mechanisms in advanced cancer cells e.g. anti-PD1/PD-L1 antibodies, anti CTLA-4 antibodies such as Ipilimumab, anti-LAG-3 antibodies, anti-CD25 antibodies, IDO-inhibitors, CD40 agonistic antibodies, CD137 agonistic antibodies, etc. (see, e.g. Hamid and Carvajal, 2013, *Expert Opinion Blot Ther* 13: 847-861; Mellman et al., 2011, *Nature Rev* 480: 480-89). The therapeutic vaccination method could in principle also be used for treating external genital warts or precursors thereof in case the vaccine comprises further (sequences encoding) E6 and/or E7 of an HPV type causing external genital warts and is administered to a subject infected by such an HPV type.

As used herein, 'treating' means administration of the vaccine to induce a therapeutic immune response against cells that express (epitopes of) HPV16 or 18 E6 and/or E7 in the patient, which leads to at least reduction of the level of and preferably complete removal of HPV16 or 18 infection, which results in at least slowing and preferably stopping the progress of HPV16- or HPV18-caused disease such as neoplasias and/or symptoms thereof. Preferably treatment with the vaccine results also in remission of more advanced stages of HPV-induced cancers. It is preferred to administer the vaccine to patients that have an established HPV infection that has been typed, so that the vaccine that encodes the polypeptide of the corresponding HPV type can be administered. In the absence of screening the vaccine can also be administered in the part of the population that is likely to be HPV infected, i.e. sexually active people. It is also possible to administer a vaccine of the invention to subjects that have not been infected by HPV16 or 18, e.g. for prophylactic use, possibly in combination with a vaccine against another HPV type by which the patient has been infected, or alternatively in non-infected subjects. A vaccine of the invention can also be administered to a subject that is subject to further treatment by other means, e.g. surgery (removal of a lesion caused by HPV16 or 18 infection), or treatment with imiquimod (comprising a TLR-7/8 agonist, see e.g. Dayaana et al., 2010, *Br J Cancer* 102: 1129-36). The effect of the treatment can be measured either by cytology or by HPV testing.

The vaccination comprises administering the vaccine of the invention to a subject or patient at least once. It is also possible to provide one or more booster administrations of one or more further vaccines. If a boosting vaccination is performed, typically, such a boosting vaccination will be administered to the same subject at a moment between one week and one year, preferably between two weeks and four months, after administering an immunogenic composition with the same antigen to the subject for the first time (which is in such cases referred to as 'priming vaccination'). In alternative boosting regimens, it is also possible to administer different vectors, e.g. one or more adenoviruses of different serotype, or other vectors such as MVA, or DNA, or protein, to the subject as a priming or boosting vaccination. In certain embodiments, the same form of a vaccine of the invention is administered at least twice to the same patient in a prime-boost regimen, e.g. with the same recombinant adenovirus (such as Ad26) of the disclosure. In certain embodiments, a vaccine of the invention is administered at least twice in a prime-boost regimen, but the vector of the vaccine is different, e.g. two different serotypes of adenoviral vectors are used, e.g. priming with recombinant Ad26 and boosting with recombinant Ad35, or vice versa; or priming with DNA and boosting with an adenoviral vector, or vice versa; or priming with an adenoviral vector and boosting with an MVA vector, or vice versa. Exemplary embodiments include priming with Ad26 vector and boosting with Ad35 vector, priming with Ad26 vector and boosting with MVA vector, priming with Ad35 vector and boosting with MVA vector, priming with Ad35 vector and boosting with Ad26 vector, etc., wherein in each case the priming and boosting vector comprise nucleic acid encoding a designer polypeptide of the disclosure, preferably the priming and boosting vector each encoding the same designer polypeptide of the disclosure. In certain embodiments, a vaccine of the disclosure is administered at least three times, in a prime-boost-boost regimen. Further booster administrations might be added to the regimen. It is also possible to simultaneously or substantially simultaneously (e.g. not more than 10 minutes apart) administer an adenoviral vector and an MVA vector (which can either be in the same composition or in different compositions), to induce an immune response (see e.g. WO 2010/073043, the disclosure of which is incorporated herein by this reference).

It is also an aspect of the invention to induce a CTL response against HPV16 or HPV18 in a subject, comprising administering a vaccine of the disclosure to the subject. The skilled person will understand that the vaccines that include HPV16 sequences (encoding or comprising any of SEQ ID NOs: 1-6) work best against and are intended for use against HPV16 infection, while the vaccines that include HPV18 sequences (encoding or comprising any of SEQ ID NOs: 20-23) work best against and are intended for use against HPV18 infection.

Provided is also the following non-limiting embodiments:

1) a nucleic acid encoding a polypeptide comprising SEQ ID NO: 1;

2) a nucleic acid according to embodiment 1, wherein the polypeptide further comprises at least part of HPV E2 protein;

3) a nucleic acid according to embodiment 2, wherein the at least part of the HPV E2 protein is from the E2 protein of HPV16;

4) a nucleic acid according to embodiment 2, wherein the polypeptide comprises at least part of the E2 protein fused to the N-terminal side of the polypeptide with SEQ ID NO: 1;

5) a nucleic acid according to embodiment 2, wherein the polypeptide comprises at least part of the E2 protein fused to the C-terminal side of the polypeptide with SEQ ID NO: 1;

6) a nucleic acid according to embodiment 3, wherein the polypeptide comprises at least part of the E2 protein fused to the N-terminal side of the polypeptide with SEQ ID NO: 1;

7) a nucleic acid according to embodiment 3, wherein the polypeptide comprises at least part of the E2 protein fused to the C-terminal side of the polypeptide with SEQ ID NO: 1;

8) a nucleic acid according to embodiment 2, wherein the at least part of the E2 protein comprises a variant of the E2 protein with a mutation that abrogates DNA binding of E2;

9) a nucleic acid according to embodiment 3, wherein the at least part of the E2 protein comprises a variant of the E2 protein with a mutation that abrogates DNA binding of E2;

10) a nucleic acid according to embodiment 4, wherein the at least part of the E2 protein comprises a variant of the E2 protein with a mutation that abrogates DNA binding of E2;

11) a nucleic acid according to embodiment 5, wherein the at least part of the E2 protein comprises a variant of the E2 protein with a mutation that abrogates DNA binding of E2;

12) a nucleic acid according to embodiment 6, wherein the at least part of the E2 protein comprises a variant of the E2 protein with a mutation that abrogates DNA binding of E2;

13) a nucleic acid according to embodiment 7, wherein the at least part of the E2 protein comprises a variant of the E2 protein with a mutation that abrogates DNA binding of E2;

14) a vector comprising a nucleic acid according to embodiment 1, wherein a sequence encoding the polypeptide is operably linked to a promoter;

15) a vector comprising a nucleic acid according to embodiment 2, wherein a sequence encoding the polypeptide is operably linked to a promoter;

16) a vector comprising a nucleic acid according to embodiment 3, wherein a sequence encoding the polypeptide is operably linked to a promoter;

17) a vector comprising a nucleic acid according to embodiment 4, wherein a sequence encoding the polypeptide is operably linked to a promoter;

18) a vector comprising a nucleic acid according to embodiment 5, wherein a sequence encoding the polypeptide is operably linked to a promoter;

19) a vector comprising a nucleic acid according to embodiment 6, wherein a sequence encoding the polypeptide is operably linked to a promoter;

20) a vector comprising a nucleic acid according to embodiment 7, wherein a sequence encoding the polypeptide is operably linked to a promoter;

21) a vector comprising a nucleic acid according to embodiment 8, wherein a sequence encoding the polypeptide is operably linked to a promoter;

22) a vector comprising a nucleic acid according to embodiment 9, wherein a sequence encoding the polypeptide is operably linked to a promoter;

23) a vector comprising a nucleic acid according to embodiment 10, wherein a sequence encoding the polypeptide is operably linked to a promoter;

24) a vector comprising a nucleic acid according to embodiment 11, wherein a sequence encoding the polypeptide is operably linked to a promoter;

25) a vector comprising a nucleic acid according to embodiment 12, wherein a sequence encoding the polypeptide is operably linked to a promoter;

26) a vector comprising a nucleic acid according to embodiment 13, wherein a sequence encoding the polypeptide is operably linked to a promoter;

27) a vector according to embodiment 14, wherein the vector is an adenovirus;

28) a vector according to embodiment 15, wherein the vector is an adenovirus;

29) a vector according to embodiment 16, wherein the vector is an adenovirus;

30) a vector according to embodiment 17, wherein the vector is an adenovirus;

31) a vector according to embodiment 18, wherein the vector is an adenovirus;

32) a vector according to embodiment 19, wherein the vector is an adenovirus;

33) a vector according to embodiment 20, wherein the vector is an adenovirus;

34) a vector according to embodiment 21, wherein the vector is an adenovirus;

35) a vector according to embodiment 22, wherein the vector is an adenovirus;

36) a vector according to embodiment 23, wherein the vector is an adenovirus;

37) a vector according to embodiment 24, wherein the vector is an adenovirus;

38) a vector according to embodiment 25, wherein the vector is an adenovirus;

39) a vector according to embodiment 26, wherein the vector is an adenovirus;

40) a vector according to embodiment 27, wherein the adenovirus is a human adenovirus of serotype 26;

41) a vector according to embodiment 28, wherein the adenovirus is a human adenovirus of serotype 26;

42) a vector according to embodiment 29, wherein the adenovirus is a human adenovirus of serotype 26;

43) a vector according to embodiment 30, wherein the adenovirus is a human adenovirus of serotype 26;

44) a vector according to embodiment 31, wherein the adenovirus is a human adenovirus of serotype 26;

45) a vector according to embodiment 32, wherein the adenovirus is a human adenovirus of serotype 26;

46) a vector according to embodiment 33, wherein the adenovirus is a human adenovirus of serotype 26;

47) a vector according to embodiment 34, wherein the adenovirus is a human adenovirus of serotype 26;

48) a vector according to embodiment 35, wherein the adenovirus is a human adenovirus of serotype 26;

49) a vector according to embodiment 36, wherein the adenovirus is a human adenovirus of serotype 26;

50) a vector according to embodiment 37, wherein the adenovirus is a human adenovirus of serotype 26;

51) a vector according to embodiment 38, wherein the adenovirus is a human adenovirus of serotype 26;

52) a vector according to embodiment 39, wherein the adenovirus is a human adenovirus of serotype 26;

53) a vector according to embodiment 28, wherein the adenovirus is a human adenovirus of serotype 35;

54) a vector according to embodiment 29, wherein the adenovirus is a human adenovirus of serotype 35;

55) a vector according to embodiment 30, wherein the adenovirus is a human adenovirus of serotype 35;

56) a vector according to embodiment 31, wherein the adenovirus is a human adenovirus of serotype 35;

57) a vector according to embodiment 32, wherein the adenovirus is a human adenovirus of serotype 35;

58) a vector according to embodiment 33, wherein the adenovirus is a human adenovirus of serotype 35;

59) a vector according to embodiment 34, wherein the adenovirus is a human adenovirus of serotype 35;

60) a vector according to embodiment 35, wherein the adenovirus is a human adenovirus of serotype 35;

61) a vector according to embodiment 36, wherein the adenovirus is a human adenovirus of serotype 35;

62) a vector according to embodiment 37, wherein the adenovirus is a human adenovirus of serotype 35;

63) a vector according to embodiment 38, wherein the adenovirus is a human adenovirus of serotype 35;

64) a vector according to embodiment 39, wherein the adenovirus is a human adenovirus of serotype 35;

65) a vaccine composition comprising a vector according to embodiment 14, and a pharmaceutically acceptable excipient;

66) a vaccine composition comprising a vector according to embodiment 15, and a pharmaceutically acceptable excipient;

67) a vaccine composition comprising a vector according to embodiment 16, and a pharmaceutically acceptable excipient;

68) a vaccine composition comprising a vector according to embodiment 17, and a pharmaceutically acceptable excipient;

69) a vaccine composition comprising a vector according to embodiment 18, and a pharmaceutically acceptable excipient;

70) a vaccine composition comprising a vector according to embodiment 19, and a pharmaceutically acceptable excipient;
71) a vaccine composition comprising a vector according to embodiment 20, and a pharmaceutically acceptable excipient;
72) a vaccine composition comprising a vector according to embodiment 21, and a pharmaceutically acceptable excipient;
73) a vaccine composition comprising a vector according to embodiment 22, and a pharmaceutically acceptable excipient;
74) a vaccine composition comprising a vector according to embodiment 23, and a pharmaceutically acceptable excipient;
75) a vaccine composition comprising a vector according to embodiment 24, and a pharmaceutically acceptable excipient;
76) a vaccine composition comprising a vector according to embodiment 25, and a pharmaceutically acceptable excipient;
77) a vaccine composition comprising a vector according to embodiment 26, and a pharmaceutically acceptable excipient;
78) a vaccine composition comprising a vector according to embodiment 27, and a pharmaceutically acceptable excipient;
79) a vaccine composition comprising a vector according to embodiment 28, and a pharmaceutically acceptable excipient;
80) a vaccine composition comprising a vector according to embodiment 29, and a pharmaceutically acceptable excipient;
81) a vaccine composition comprising a vector according to embodiment 30, and a pharmaceutically acceptable excipient;
82) a vaccine composition comprising a vector according to embodiment 31, and a pharmaceutically acceptable excipient;
83) a vaccine composition comprising a vector according to embodiment 32, and a pharmaceutically acceptable excipient;
84) a vaccine composition comprising a vector according to embodiment 33, and a pharmaceutically acceptable excipient;
85) a vaccine composition comprising a vector according to embodiment 34, and a pharmaceutically acceptable excipient;
86) a vaccine composition comprising a vector according to embodiment 35, and a pharmaceutically acceptable excipient;
87) a vaccine composition comprising a vector according to embodiment 36, and a pharmaceutically acceptable excipient;
88) a vaccine composition comprising a vector according to embodiment 37, and a pharmaceutically acceptable excipient;
89) a vaccine composition comprising a vector according to embodiment 38, and a pharmaceutically acceptable excipient;
90) a vaccine composition comprising a vector according to embodiment 39, and a pharmaceutically acceptable excipient;
91) a vaccine composition comprising a vector according to embodiment 40, and a pharmaceutically acceptable excipient;
92) a vaccine composition comprising a vector according to embodiment 41, and a pharmaceutically acceptable excipient;
93) a vaccine composition comprising a vector according to embodiment 42, and a pharmaceutically acceptable excipient;
94) a vaccine composition comprising a vector according to embodiment 43, and a pharmaceutically acceptable excipient;
95) a vaccine composition comprising a vector according to embodiment 44, and a pharmaceutically acceptable excipient;
96) a vaccine composition comprising a vector according to embodiment 45, and a pharmaceutically acceptable excipient;
97) a vaccine composition comprising a vector according to embodiment 46, and a pharmaceutically acceptable excipient;
98) a vaccine composition comprising a vector according to embodiment 47, and a pharmaceutically acceptable excipient;
99) a vaccine composition comprising a vector according to embodiment 48, and a pharmaceutically acceptable excipient;
100) a vaccine composition comprising a vector according to embodiment 49, and a pharmaceutically acceptable excipient;
101) a vaccine composition comprising a vector according to embodiment 50, and a pharmaceutically acceptable excipient;
102) a vaccine composition comprising a vector according to embodiment 51, and a pharmaceutically acceptable excipient;
103) a vaccine composition comprising a vector according to embodiment 52, and a pharmaceutically acceptable excipient;
104) a vaccine composition comprising a vector according to embodiment 53, and a pharmaceutically acceptable excipient;
105) a vaccine composition comprising a vector according to embodiment 54, and a pharmaceutically acceptable excipient;
106) a vaccine composition comprising a vector according to embodiment 55, and a pharmaceutically acceptable excipient;
107) a vaccine composition comprising a vector according to embodiment 56, and a pharmaceutically acceptable excipient;
108) a vaccine composition comprising a vector according to embodiment 57, and a pharmaceutically acceptable excipient;
109) a vaccine composition comprising a vector according to embodiment 58, and a pharmaceutically acceptable excipient;
110) a vaccine composition comprising a vector according to embodiment 59, and a pharmaceutically acceptable excipient;
111) a vaccine composition comprising a vector according to embodiment 60, and a pharmaceutically acceptable excipient;
112) a vaccine composition comprising a vector according to embodiment 61, and a pharmaceutically acceptable excipient;
113) a vaccine composition comprising a vector according to embodiment 62, and a pharmaceutically acceptable excipient;

114) a vaccine composition comprising a vector according to embodiment 63, and a pharmaceutically acceptable excipient;

115) a vaccine composition comprising a vector according to embodiment 64, and a pharmaceutically acceptable excipient;

116) a method for inducing an immune response against HPV in a subject, comprising administering to the subject a vaccine composition according to any one of embodiments 65-115;

117) a method for treating persistent HPV (type 16) infection, comprising administering a vaccine according to any one of embodiments 65-115 to a subject that suffers from persistent HPV infection;

118) a method for treating vulvar intraepithelial neoplasia (VIN) (with underlying HPV type 16 infection), comprising administering a vaccine according to any one of embodiments 65-115 to a subject that suffers from VIN;

119) a method for treating vulvar cancer (with underlying HPV type 16 infection), comprising administering a vaccine according to any one of embodiments 65-115 to a subject that suffers from vulvar cancer;

120) a method for treating cervical intraepithelial neoplasia (CIN) (with underlying HPV type 16 infection), comprising administering a vaccine according to any one of embodiments 65-115 to a subject that suffers from CIN;

121) a method for treating cervical cancer (with underlying HPV type 16 infection), comprising administering a vaccine according to any one of embodiments 65-115 to a subject that suffers from cervical cancer;

122) a method for treating oropharyngeal cancer (with underlying HPV type 16 infection), comprising administering a vaccine according to any one of embodiments 65-115 to a subject that suffers from oropharyngeal cancer;

123) a method for treating penile intraepithelial neoplasia (PIN) (with underlying HPV type 16 infection), comprising administering a vaccine according to any one of embodiments 65-115 to a subject that suffers from PIN;

124) a method for treating penile cancer (with underlying HPV type 16 infection), comprising administering a vaccine according to any one of embodiments 65-115 to a subject that suffers from penile cancer;

125) a method for treating vaginal intraepithelial neoplasia (VaIN) (with underlying HPV type 16 infection), comprising administering a vaccine according to any one of embodiments 65-115 to a subject that suffers from VaIN;

126) a method for treating vaginal cancer (with underlying HPV type 16 infection), comprising administering a vaccine according to any one of embodiments 65-115 to a subject that suffers from vaginal cancer;

127) a method for treating anal intraepithelial neoplasia (AIN) (with underlying HPV type 16 infection), comprising administering a vaccine according to any one of embodiments 65-115 to a subject that suffers from AIN;

128) a method for treating anal cancer (with underlying HPV type 16 infection), comprising administering a vaccine according to any one of embodiments 65-115 to a subject that suffers from anal cancer;

129) a polypeptide comprising SEQ ID NO: 1;

130) a polypeptide according to embodiment 129, wherein the polypeptide further comprises at least part of HPV E2 protein;

131) a polypeptide according to embodiment 130, wherein the at least part of the HPV E2 protein is from the E2 protein of HPV16;

132) a polypeptide according to embodiment 130, wherein at least part of the E2 protein is fused to the N-terminal side of the polypeptide with SEQ ID NO: 1;

133) a polypeptide according to embodiment 130, wherein at least part of the E2 protein is fused to the C-terminal side of the polypeptide with SEQ ID NO: 1;

134) a polypeptide according to embodiment 131, wherein at least part of the E2 protein is fused to the N-terminal side of the polypeptide with SEQ ID NO: 1;

135) a polypeptide according to embodiment 131, wherein at least part of the E2 protein is fused to the C-terminal side of the polypeptide with SEQ ID NO: 1;

136) a polypeptide according to embodiment 130, wherein the at least part of the E2 protein comprises a variant of the E2 protein with a mutation that abrogates DNA binding of E2;

137) a polypeptide according to embodiment 131, wherein the at least part of the E2 protein comprises a variant of the E2 protein with a mutation that abrogates DNA binding of E2;

138) a polypeptide according to embodiment 132, wherein the at least part of the E2 protein comprises a variant of the E2 protein with a mutation that abrogates DNA binding of E2;

139) a polypeptide according to embodiment 133, wherein the at least part of the E2 protein comprises a variant of the E2 protein with a mutation that abrogates DNA binding of E2;

140) a polypeptide according to embodiment 134, wherein the at least part of the E2 protein comprises a variant of the E2 protein with a mutation that abrogates DNA binding of E2;

141) a polypeptide according to embodiment 135, wherein the at least part of the E2 protein comprises a variant of the E2 protein with a mutation that abrogates DNA binding of E2;

142) a nucleic acid according to embodiment 3, encoding a polypeptide according to SEQ ID NO: 3;

143) a nucleic acid according to embodiment 3, encoding a polypeptide according to SEQ ID NO: 5;

144) a vector encoding a nucleic acid according to embodiment 142, wherein a sequence encoding the polypeptide is operably linked to a promoter;

145) a vector encoding a nucleic acid according to embodiment 143, wherein a sequence encoding the polypeptide is operably linked to a promoter;

146) a vector according to embodiment 144, wherein the vector is an adenovirus;

147) a vector according to embodiment 145, wherein the vector is an adenovirus;

148) a vector according to embodiment 146, wherein the adenovirus is a human adenovirus of serotype 26;

149) a vector according to embodiment 147, wherein the adenovirus is a human adenovirus of serotype 26;

150) a vector according to embodiment 146, wherein the adenovirus is a human adenovirus of serotype 35;

151) a vector according to embodiment 147, wherein the adenovirus is a human adenovirus of serotype 35;

152) a vaccine composition comprising a vector according to embodiment 144, and a pharmaceutically acceptable excipient;

153) a vaccine composition comprising a vector according to embodiment 145, and a pharmaceutically acceptable excipient;

154) a vaccine composition comprising a vector according to embodiment 146, and a pharmaceutically acceptable excipient;

155) a vaccine composition comprising a vector according to embodiment 147, and a pharmaceutically acceptable excipient;

156) a vaccine composition comprising a vector according to embodiment 148, and a pharmaceutically acceptable excipient;

157) a vaccine composition comprising a vector according to embodiment 149, and a pharmaceutically acceptable excipient;

158) a vaccine composition comprising a vector according to embodiment 150, and a pharmaceutically acceptable excipient;

159) a vaccine composition comprising a vector according to embodiment 151, and a pharmaceutically acceptable excipient;

160) a method for inducing an immune response against HPV in a subject, comprising administering to the subject a vaccine composition according to any one of embodiments 152-159;

161) a method for treating vulvar intraepithelial neoplasia (VIN), comprising administering a vaccine according to any one of embodiments 152-159 to a subject that suffers from VIN;

162) a method for treating vulvar cancer, comprising administering a vaccine according to any one of embodiments 152-159 to a subject that suffers from vulvar cancer;

163) a method for treating cervical intraepithelial neoplasia (CIN), comprising administering a vaccine according to any one of embodiments 152-159 to a subject that suffers from CIN;

164) a method for treating cervical cancer, comprising administering a vaccine according to any one of embodiments 152-159 to a subject that suffers from cervical cancer;

165) a method for treating opopharyngeal cancer, comprising administering a vaccine according to any one of embodiments 152-159 to a subject that suffers from oropharyngeal cancer;

166) a method for treating penile intraepithelial neoplasia (PIN), comprising administering a vaccine according to any one of embodiments 152-159 to a subject that suffers from PIN;

167) a method for treating penile cancer, comprising administering a vaccine according to any one of embodiments 152-159 to a subject that suffers from penile cancer;

168) a method for treating vaginal intraepithelial neoplasia (VaIN), comprising administering a vaccine according to any one of embodiments 152-159 to a subject that suffers from VaIN;

169) a method for treating vaginal cancer, comprising administering a vaccine according to any one of embodiments 152-159 to a subject that suffers from vaginal cancer;

170) a method for treating anal intraepithelial neoplasia (AIN), comprising administering a vaccine according to any one of embodiments 152-159 to a subject that suffers from AIN;

171) a method for treating anal cancer, comprising administering a vaccine according to any one of embodiments 152-159 to a subject that suffers from anal cancer;

172) a nucleic acid encoding a polypeptide comprising SEQ ID NO: 20;

173) a nucleic acid according to embodiment 172, wherein the polypeptide further comprises at least part of HPV E2 protein;

174) a nucleic acid according to embodiment 173, wherein the at least part of the HPV E2 protein is from the E2 protein of HPV18;

175) a nucleic acid according to embodiment 173, wherein the polypeptide comprises at least part of the E2 protein fused to the N-terminal side of the polypeptide with SEQ ID NO: 20;

176) a nucleic acid according to embodiment 173, wherein the polypeptide comprises at least part of the E2 protein fused to the C-terminal side of the polypeptide with SEQ ID NO: 20;

177) a nucleic acid according to embodiment 174, wherein the polypeptide comprises at least part of the E2 protein fused to the N-terminal side of the polypeptide with SEQ ID NO: 20;

178) a nucleic acid according to embodiment 174, wherein the polypeptide comprises at least part of the E2 protein fused to the C-terminal side of the polypeptide with SEQ ID NO: 20;

179) a nucleic acid according to embodiment 173, wherein the at least part of the E2 protein comprises a variant of the E2 protein with a mutation that abrogates DNA binding of E2;

180) a nucleic acid according to embodiment 174, wherein the at least part of the E2 protein comprises a variant of the E2 protein with a mutation that abrogates DNA binding of E2;

181) a nucleic acid according to embodiment 175, wherein the at least part of the E2 protein comprises a variant of the E2 protein with a mutation that abrogates DNA binding of E2;

182) a nucleic acid according to embodiment 176, wherein the at least part of the E2 protein comprises a variant of the E2 protein with a mutation that abrogates DNA binding of E2;

183) a nucleic acid according to embodiment 177, wherein the at least part of the E2 protein comprises a variant of the E2 protein with a mutation that abrogates DNA binding of E2;

184) a nucleic acid according to embodiment 178, wherein the at least part of the E2 protein comprises a variant of the E2 protein with a mutation that abrogates DNA binding of E2;

185) a vector comprising a nucleic acid according to embodiment 172, wherein a sequence encoding the polypeptide is operably linked to a promoter;

186) a vector comprising a nucleic acid according to embodiment 173, wherein a sequence encoding the polypeptide is operably linked to a promoter;

187) a vector comprising a nucleic acid according to embodiment 174, wherein a sequence encoding the polypeptide is operably linked to a promoter;

188) a vector comprising a nucleic acid according to embodiment 175, wherein a sequence encoding the polypeptide is operably linked to a promoter;

189) a vector comprising a nucleic acid according to embodiment 176, wherein a sequence encoding the polypeptide is operably linked to a promoter;

190) a vector comprising a nucleic acid according to embodiment 177, wherein a sequence encoding the polypeptide is operably linked to a promoter;

191) a vector comprising a nucleic acid according to embodiment 178, wherein a sequence encoding the polypeptide is operably linked to a promoter;

192) a vector comprising a nucleic acid according to embodiment 179, wherein a sequence encoding the polypeptide is operably linked to a promoter;

193) a vector comprising a nucleic acid according to embodiment 180, wherein a sequence encoding the polypeptide is operably linked to a promoter;

194) a vector comprising a nucleic acid according to embodiment 181, wherein a sequence encoding the polypeptide is operably linked to a promoter;

195) a vector comprising a nucleic acid according to embodiment 182, wherein a sequence encoding the polypeptide is operably linked to a promoter;

196) a vector comprising a nucleic acid according to embodiment 183, wherein a sequence encoding the polypeptide is operably linked to a promoter;

197) a vector comprising a nucleic acid according to embodiment 184, wherein a sequence encoding the polypeptide is operably linked to a promoter;

198) a vector according to embodiment 185, wherein the vector is an adenovirus;

199) a vector according to embodiment 186, wherein the vector is an adenovirus;

200) a vector according to embodiment 187, wherein the vector is an adenovirus;

201) a vector according to embodiment 188, wherein the vector is an adenovirus;

202) a vector according to embodiment 189, wherein the vector is an adenovirus;

203) a vector according to embodiment 190, wherein the vector is an adenovirus;

204) a vector according to embodiment 191, wherein the vector is an adenovirus;

205) a vector according to embodiment 192, wherein the vector is an adenovirus;

206) a vector according to embodiment 193, wherein the vector is an adenovirus;

207) a vector according to embodiment 194, wherein the vector is an adenovirus;

208) a vector according to embodiment 195, wherein the vector is an adenovirus;

209) a vector according to embodiment 196, wherein the vector is an adenovirus;

210) a vector according to embodiment 197, wherein the vector is an adenovirus;

211) a vector according to embodiment 198, wherein the adenovirus is a human adenovirus of serotype 26;

212) a vector according to embodiment 199, wherein the adenovirus is a human adenovirus of serotype 26;

213) a vector according to embodiment 200, wherein the adenovirus is a human adenovirus of serotype 26;

214) a vector according to embodiment 201, wherein the adenovirus is a human adenovirus of serotype 26;

215) a vector according to embodiment 202, wherein the adenovirus is a human adenovirus of serotype 26;

216) a vector according to embodiment 203, wherein the adenovirus is a human adenovirus of serotype 26;

217) a vector according to embodiment 204, wherein the adenovirus is a human adenovirus of serotype 26;

218) a vector according to embodiment 205, wherein the adenovirus is a human adenovirus of serotype 26;

219) a vector according to embodiment 206, wherein the adenovirus is a human adenovirus of serotype 26;

220) a vector according to embodiment 207, wherein the adenovirus is a human adenovirus of serotype 26;

221) a vector according to embodiment 208, wherein the adenovirus is a human adenovirus of serotype 26;

222) a vector according to embodiment 209, wherein the adenovirus is a human adenovirus of serotype 26;

223) a vector according to embodiment 210, wherein the adenovirus is a human adenovirus of serotype 26;

224) a vector according to embodiment 198, wherein the adenovirus is a human adenovirus of serotype 35;

225) a vector according to embodiment 199, wherein the adenovirus is a human adenovirus of serotype 35;

226) a vector according to embodiment 200, wherein the adenovirus is a human adenovirus of serotype 35;

227) a vector according to embodiment 201, wherein the adenovirus is a human adenovirus of serotype 35;

228) a vector according to embodiment 202, wherein the adenovirus is a human adenovirus of serotype 35;

229) a vector according to embodiment 203, wherein the adenovirus is a human adenovirus of serotype 35;

230) a vector according to embodiment 204, wherein the adenovirus is a human adenovirus of serotype 35;

231) a vector according to embodiment 205, wherein the adenovirus is a human adenovirus of serotype 35;

232) a vector according to embodiment 206, wherein the adenovirus is a human adenovirus of serotype 35;

233) a vector according to embodiment 207, wherein the adenovirus is a human adenovirus of serotype 35;

234) a vector according to embodiment 208, wherein the adenovirus is a human adenovirus of serotype 35;

235) a vector according to embodiment 209, wherein the adenovirus is a human adenovirus of serotype 35;

236) a vector according to embodiment 210, wherein the adenovirus is a human adenovirus of serotype 35;

237) a vaccine composition comprising a vector according to embodiment 185, and a pharmaceutically acceptable excipient;

238) a vaccine composition comprising a vector according to embodiment 186, and a pharmaceutically acceptable excipient;

239) a vaccine composition comprising a vector according to embodiment 187, and a pharmaceutically acceptable excipient;

240) a vaccine composition comprising a vector according to embodiment 188, and a pharmaceutically acceptable excipient;

241) a vaccine composition comprising a vector according to embodiment 189, and a pharmaceutically acceptable excipient;

242) a vaccine composition comprising a vector according to embodiment 190, and a pharmaceutically acceptable excipient;

243) a vaccine composition comprising a vector according to embodiment 191, and a pharmaceutically acceptable excipient;

244) a vaccine composition comprising a vector according to embodiment 192, and a pharmaceutically acceptable excipient;

245) a vaccine composition comprising a vector according to embodiment 193, and a pharmaceutically acceptable excipient;

246) a vaccine composition comprising a vector according to embodiment 194, and a pharmaceutically acceptable excipient;

247) a vaccine composition comprising a vector according to embodiment 195, and a pharmaceutically acceptable excipient;

248) a vaccine composition comprising a vector according to embodiment 196, and a pharmaceutically acceptable excipient;

249) a vaccine composition comprising a vector according to embodiment 197, and a pharmaceutically acceptable excipient;

250) a vaccine composition comprising a vector according to embodiment 198, and a pharmaceutically acceptable excipient;

251) a vaccine composition comprising a vector according to embodiment 199, and a pharmaceutically acceptable excipient;
252) a vaccine composition comprising a vector according to embodiment 200, and a pharmaceutically acceptable excipient;
253) a vaccine composition comprising a vector according to embodiment 201, and a pharmaceutically acceptable excipient;
254) a vaccine composition comprising a vector according to embodiment 202, and a pharmaceutically acceptable excipient;
255) a vaccine composition comprising a vector according to embodiment 203, and a pharmaceutically acceptable excipient;
256) a vaccine composition comprising a vector according to embodiment 204, and a pharmaceutically acceptable excipient;
257) a vaccine composition comprising a vector according to embodiment 205, and a pharmaceutically acceptable excipient;
258) a vaccine composition comprising a vector according to embodiment 206, and a pharmaceutically acceptable excipient;
259) a vaccine composition comprising a vector according to embodiment 207, and a pharmaceutically acceptable excipient;
260) a vaccine composition comprising a vector according to embodiment 208, and a pharmaceutically acceptable excipient;
261) a vaccine composition comprising a vector according to embodiment 209, and a pharmaceutically acceptable excipient;
262) a vaccine composition comprising a vector according to embodiment 210, and a pharmaceutically acceptable excipient;
263) a vaccine composition comprising a vector according to embodiment 211, and a pharmaceutically acceptable excipient;
264) a vaccine composition comprising a vector according to embodiment 212, and a pharmaceutically acceptable excipient;
265) a vaccine composition comprising a vector according to embodiment 213, and a pharmaceutically acceptable excipient;
266) a vaccine composition comprising a vector according to embodiment 214, and a pharmaceutically acceptable excipient;
267) a vaccine composition comprising a vector according to embodiment 215, and a pharmaceutically acceptable excipient;
268) a vaccine composition comprising a vector according to embodiment 216, and a pharmaceutically acceptable excipient;
269) a vaccine composition comprising a vector according to embodiment 217, and a pharmaceutically acceptable excipient;
270) a vaccine composition comprising a vector according to embodiment 218, and a pharmaceutically acceptable excipient;
271) a vaccine composition comprising a vector according to embodiment 219, and a pharmaceutically acceptable excipient;
272) a vaccine composition comprising a vector according to embodiment 220, and a pharmaceutically acceptable excipient;
273) a vaccine composition comprising a vector according to embodiment 221, and a pharmaceutically acceptable excipient;
274) a vaccine composition comprising a vector according to embodiment 222, and a pharmaceutically acceptable excipient;
275) a vaccine composition comprising a vector according to embodiment 223, and a pharmaceutically acceptable excipient;
276) a vaccine composition comprising a vector according to embodiment 224, and a pharmaceutically acceptable excipient;
277) a vaccine composition comprising a vector according to embodiment 225, and a pharmaceutically acceptable excipient;
278) a vaccine composition comprising a vector according to embodiment 226, and a pharmaceutically acceptable excipient;
279) a vaccine composition comprising a vector according to embodiment 227, and a pharmaceutically acceptable excipient;
280) a vaccine composition comprising a vector according to embodiment 228, and a pharmaceutically acceptable excipient;
281) a vaccine composition comprising a vector according to embodiment 229, and a pharmaceutically acceptable excipient;
282) a vaccine composition comprising a vector according to embodiment 230, and a pharmaceutically acceptable excipient;
283) a vaccine composition comprising a vector according to embodiment 231, and a pharmaceutically acceptable excipient;
284) a vaccine composition comprising a vector according to embodiment 232, and a pharmaceutically acceptable excipient;
285) a vaccine composition comprising a vector according to embodiment 233, and a pharmaceutically acceptable excipient;
286) a vaccine composition comprising a vector according to embodiment 234, and a pharmaceutically acceptable excipient;
287) a vaccine composition comprising a vector according to embodiment 235, and a pharmaceutically acceptable excipient;
288) a vaccine composition comprising a vector according to embodiment 236, and a pharmaceutically acceptable excipient;
289) a method for inducing an immune response against HPV in a subject, comprising administering to the subject a vaccine composition according to any one of embodiments 237-288;
290) a method for treating persistent HPV (type 18) infection, comprising administering a vaccine according to any one of embodiments 237-288 to a subject that suffers from persistent HPV infection;
291) a method for treating vulvar intraepithelial neoplasia (VIN) (with underlying HPV type 18 infection), comprising administering a vaccine according to any one of embodiments 237-288 to a subject that suffers from VIN;
292) a method for treating vulvar cancer (with underlying HPV type 18 infection), comprising administering a vaccine according to any one of embodiments 237-288 to a subject that suffers from vulvar cancer;
293) a method for treating cervical intraepithelial neoplasia (CIN) (with underlying HPV type 18 infection), comprising administering a vaccine according to any one of embodiments 237-288 to a subject that suffers from CIN;

294) a method for treating cervical cancer (with underlying HPV type 18 infection), comprising administering a vaccine according to any one of embodiments 237-288 to a subject that suffers from cervical cancer;

295) a method for treating opopharyngeal cancer (with underlying HPV type 18 infection), comprising administering a vaccine according to any one of embodiments 237-288 to a subject that suffers from oropharyngeal cancer;

296) a method for treating penile intraepithelial neoplasia (PIN) (with underlying HPV type 18 infection), comprising administering a vaccine according to any one of embodiments 237-288 to a subject that suffers from PIN;

297) a method for treating penile cancer (with underlying HPV type 18 infection), comprising administering a vaccine according to any one of embodiments 237-288 to a subject that suffers from penile cancer;

298) a method for treating vaginal intraepithelial neoplasia (VaIN) (with underlying HPV type 18 infection), comprising administering a vaccine according to any one of embodiments 237-288 to a subject that suffers from VaIN;

299) a method for treating vaginal cancer (with underlying HPV type 18 infection), comprising administering a vaccine according to any one of embodiments 237-288 to a subject that suffers from vaginal cancer;

300) a method for treating anal intraepithelial neoplasia (AIN) (with underlying HPV type 18 infection), comprising administering a vaccine according to any one of embodiments 237-288 to a subject that suffers from AIN;

301) a method for treating anal cancer (with underlying HPV type 18 infection), comprising administering a vaccine according to any one of embodiments 237-288 to a subject that suffers from anal cancer;

302) a polypeptide comprising SEQ ID NO: 20;

303) a polypeptide according to embodiment 302, wherein the polypeptide further comprises at least part of HPV E2 protein;

304) a polypeptide according to embodiment 303, wherein the at least part of the HPV E2 protein is from the E2 protein of HPV18;

305) a polypeptide according to embodiment 303, wherein at least part of the E2 protein is fused to the N-terminal side of the polypeptide with SEQ ID NO: 20;

306) a polypeptide according to embodiment 303, wherein at least part of the E2 protein is fused to the C-terminal side of the polypeptide with SEQ ID NO: 20;

307) a polypeptide according to embodiment 304, wherein at least part of the E2 protein is fused to the N-terminal side of the polypeptide with SEQ ID NO: 20;

308) a polypeptide according to embodiment 304, wherein at least part of the E2 protein is fused to the C-terminal side of the polypeptide with SEQ ID NO: 20;

309) a polypeptide according to embodiment 303, wherein the at least part of the E2 protein comprises a variant of the E2 protein with a mutation that abrogates DNA binding of E2;

310) a polypeptide according to embodiment 304, wherein the at least part of the E2 protein comprises a variant of the E2 protein with a mutation that abrogates DNA binding of E2;

311) a polypeptide according to embodiment 305, wherein the at least part of the E2 protein comprises a variant of the E2 protein with a mutation that abrogates DNA binding of E2;

312) a polypeptide according to embodiment 306, wherein the at least part of the E2 protein comprises a variant of the E2 protein with a mutation that abrogates DNA binding of E2;

313) a polypeptide according to embodiment 307, wherein the at least part of the E2 protein comprises a variant of the E2 protein with a mutation that abrogates DNA binding of E2;

314) a polypeptide according to embodiment 308, wherein the at least part of the E2 protein comprises a variant of the E2 protein with a mutation that abrogates DNA binding of E2;

315) a nucleic acid according to embodiment 174, encoding a polypeptide according to SEQ ID NO: 22;

316) a vector encoding a nucleic acid according to embodiment 315, wherein a sequence encoding the polypeptide is operably linked to a promoter;

317) a vector according to embodiment 316, wherein the vector is an adenovirus;

318) a vector according to embodiment 317, wherein the adenovirus is a human adenovirus of serotype 26;

319) a vector according to embodiment 317, wherein the adenovirus is a human adenovirus of serotype 35;

320) a vaccine composition comprising a vector according to embodiment 316, and a pharmaceutically acceptable excipient;

321) a vaccine composition comprising a vector according to embodiment 317, and a pharmaceutically acceptable excipient;

322) a vaccine composition comprising a vector according to embodiment 318, and a pharmaceutically acceptable excipient;

323) a vaccine composition comprising a vector according to embodiment 319, and a pharmaceutically acceptable excipient;

324) a method for inducing an immune response against HPV in a subject, comprising administering to the subject a vaccine composition according to any one of embodiments 320-324;

325) a method for treating vulvar intraepithelial neoplasia (VIN), comprising administering a vaccine according to any one of embodiments 320-324 to a subject that suffers from VIN;

326) a method for treating vulvar cancer, comprising administering a vaccine according to any one of embodiments 320-324 to a subject that suffers from vulvar cancer;

327) a method for treating cervical intraepithelial neoplasia (CIN), comprising administering a vaccine according to any one of embodiments 320-324 to a subject that suffers from CIN;

328) a method for treating cervical cancer, comprising administering a vaccine according to any one of embodiments 320-324 to a subject that suffers from cervical cancer;

329) a method for treating opopharyngeal cancer, comprising administering a vaccine according to any one of embodiments 320-324 to a subject that suffers from oropharyngeal cancer;

330) a method for treating penile intraepithelial neoplasia (PIN), comprising administering a vaccine according to any one of embodiments 320-324 to a subject that suffers from PIN;

331) a method for treating penile cancer, comprising administering a vaccine according to any one of embodiments 320-324 to a subject that suffers from penile cancer;

332) a method for treating vaginal intraepithelial neoplasia (VaIN), comprising administering a vaccine according to any one of embodiments 320-324 to a subject that suffers from VaIN;

333) a method for treating vaginal cancer, comprising administering a vaccine according to any one of embodiments 320-324 to a subject that suffers from vaginal cancer;

334) a method for treating anal intraepithelial neoplasia (AIN), comprising administering a vaccine according to any one of embodiments 320-324 to a subject that suffers from AIN;

335) a method for treating anal cancer, comprising administering a vaccine according to any one of embodiments 320-324 to a subject that suffers from anal cancer;

336) a composition comprising nucleic acid encoding SEQ ID NO: 1 and nucleic acid encoding SEQ ID NO: 20;

337) a composition according to embodiment 336, comprising nucleic acid encoding SEQ ID NO: 3 and nucleic acid encoding SEQ ID NO: 22;

338) a method for inducing an immune response in a subject against HPV, comprising administering to the subject nucleic acid encoding SEQ ID NO: 1 and nucleic acid encoding SEQ ID NO: 20;

339) a method according to embodiment 338, comprising administering to the subject nucleic acid encoding SEQ ID NO: 3 and nucleic acid encoding SEQ ID NO: 22;

340) a kit of parts comprising (i) nucleic acid encoding SEQ ID NO: 1 and (ii) nucleic acid encoding SEQ ID NO: 20;

341) a vaccine composition comprising nucleic acid encoding SEQ ID NO: 1 and nucleic acid encoding SEQ ID NO: 20, and a pharmaceutically acceptable excipient;

342) a method for treating persistent HPV infection, vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC), oropharyngeal cancer, penile cancer, vaginal cancer or anal cancer in a subject, the method comprising administering to the subject nucleic acid encoding SEQ ID NO: 1 and nucleic acid encoding SEQ ID NO: 20.

The practice of this invention will employ, unless otherwise indicated, conventional techniques of immunology, molecular biology, microbiology, cell biology, and recombinant DNA, which are within the skill of the art. See e.g. Sambrook, Fritsch and Maniatis, Molecular Cloning: A Laboratory Manual, 2$^{nd}$ edition, 1989; Current Protocols in Molecular Biology, Ausubel F M, et al., eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

The invention is further explained in the following examples. The examples do not limit the invention in any way. They merely serve to clarify the invention.

EXAMPLES

Example 1: Construction of a Designer Polypeptide Comprising Essentially all HPV16 E6 and E7 CTL Epitopes We designed a novel, non-tumorigenic polypeptide (and nucleic acid encoding such) that contains essentially all CTL epitopes of HPV16 E6 and E7 proteins, and has a minimum number of anticipated/predicted strong neo-epitopes (neo-epitopes meaning epitopes not present in the wild type HPV16 E6 and E7 proteins). The polypeptide of the disclosure (also sometimes referred to as 'E6E7SH' herein) for HPV16 comprises a sequence as provided in SEQ ID NO: 1. A codon-optimized nucleic acid encoding this polypeptide is provided in SEQ ID NO: 2.

The molecules of the disclosure are single molecules, which provides manufacturing advantages over strategies where multiple molecules are used. In addition, the polypeptide of the disclosure comprises essentially all putative CTL epitopes that are present in wild-type E6 and E7 of HPV16, and at the same time have a minimum number of anticipated/predicted strong neo-epitopes that could potentially be immunodominant and thus divert the immune response from relevant wild-type CTL epitopes. Thus the constructs of the disclosure are immunologically more favourable than molecules described by others that either lack possible CTL epitopes and/or that contain more or stronger neo-epitopes.

For instance, the construct of SEQ ID NO: 1 contains only one neo-epitope with a length of nine amino acids with a predicted binding affinity <50 nM for the 20 most common HLA-A, 20 most common HLA-B and 20 most common HLA-C alleles (HLA-A*01:01, HLA-A*02:01, HLA-A*02:03, HLA-A*02:06, HLA-A*02:07, HLA-A*03:01, HLA-A*11:01, HLA-A*23:01, HLA-A*24:02, HLA-A*26:01, HLA-A*29:02, HLA-A*30:01, HLA-A*30:02, HLA-A*31:01, HLA-A*32:01, HLA-A*33:01, HLA-A*33:03, HLA-A*34:01, HLA-A*68:01, HLA-A*68:02, HLA-B*07:02, HLA-B*07:04, HLA-B*08:01, HLA-B*13:01, HLA-B*15:01, HLA-B*18:01, HLA-B*35:01, HLA-B*37:01, HLA-B*39:01, HLA-B*40:01, HLA-B*40:02, HLA-B*40:06, HLA-B*44:02, HLA-B*44:03, HL-B*46:01, HLA-B*48:01, HLA-B*51:01, HLA-B*52:01, HLA-B*53:01, HLA-B*58:01, HLA-C*07:02, HLA-C*04:01, HLA-C*03:04, HLA-C*01:02, HLA-C*07:01, HLA-C*06:02, HLA-C*03:03, HLA-C*08:01, HLA-C*15:02, HLA-C*12:02, HLA-C*02:02, HLA-C*05:01, HLA-C*14:02, HLA-C*03:02, HLA-C*16:01, HLA-C*08:02, HLA-C*12:03, HLA-C*04:03, HLA-C*17:01, HLA-C*14:03), as determined using the ANN (Lundegaard et al., 2008, *Nucl Acids Res* 36: W509-12) and SMM method (Peters et al., 2003, *Bioinformatics* 19: 1765-72) for HLA-A and HLA-B and the NetMHCpan method (Hoof et al., 2009, *Immunogenetics* 61: 1-13) for HLA-C of the prediction tool for 'Peptide binding to MHC class I molecules' at the IEDB website (http://tools.mmu-norg/analyze/html/mhc_binding.html, version 2009-09-01B). Zhang et al (2008) describe the IEDB analysis resource.

As a non-limiting example, using the SMM prediction tool at the IEDB website, the shuffled E6 and E7 sequences as described by Oosterhuis et al., 2011, *Int J Cancer* 129: 397-406 and Öhlschläger et al., 2006, *Vaccine* 24: 2880-93 contain each nine potential strong unique neo-epitopes (ANN or SMM IC50<50 nM) for the 20 most HLA-A and -B, in the core part. This even excludes the appendices used in that approach (in which appendices will further contribute to additional neo-epitopes, and may miss out on more native MHC II epitopes due to the limited length of the 'overlap'). Indeed, a reportedly improved molecule containing a variant with shuffled E6 and E7 proteins that was described in WO 2013/083287, the disclosure of which is incorporated herein by this reference, contains 22 unique neo-epitopes with a length of nine amino acids with a predicted IC50<50 nM (ANN, SMM or NetMHCPan) for the 20 most common HLA-A, 20 most common HLA-B and 20 most common HLA-C alleles.

Hence, the designer molecules of the disclosure clearly are favourable in having much lower number of predicted neo-epitopes compared to other published approaches where E6 and E7 where shuffled to remove functionality.

Nucleic acid encoding our thus designed HPV16 E6E7SH molecule (i.e. a polypeptide having amino acid sequence as provided in SEQ ID NO:1) was synthesized, the nucleic acid sequence comprising SEQ ID NO: 2, and flanked by a HindIII site and a Kozak sequence on the 5'end and an XbaI site on the 3'site (custom synthesis and standard molecular cloning at Invitrogen Life technologies, Germany).

The synthesised fragments were cloned using HindIII and XbaI into a standard expression vector, pCDNA2004.Neo, harbouring both a bacterial resistance marker (Ampicillin) and a mammalian resistance marker (Neomycin), to obtain plasmid vectors encoding a molecule of the invention, e.g. for (transient) transfection based experiments.

These molecules could be used as such, but also as the basis for further molecules that contain additional features. As non-limiting examples, some further variants were prepared as described below.

The HPV16 E6E7SH fusion protein sequence can be combined with sequences of other HPV16 early proteins to target individuals with persistent infection and to broaden the immune repertoire in an immunized individual. Immune responses against E2 have been suggested to play an important role in the clearance of HPV16 infections (de Jong et al., 2002, Cancer Res 62: 472-479). Fusion of E2 to E6E7SH will give a vaccine component that harbours antigens against the stages of HPV-related cancer from persistent infection to invasive cancer or recurrent/refractory disease after LEEP surgery. Therefore, as a non-limiting example of such embodiments, we prepared a sequence coding for a fusion protein of E6E7SH with E2 at its N-terminus. In the E2 sequence modifications can be made to abrogate DNA binding activity that might affect gene expression in cells expressing the fusion protein. We mutated Glycine at position 293, Lysine at position 299 and Cysteine at position 300 of the wt HPV16 E2 protein into respectively Valine, Methionine and Arginine. Each of these mutations on its own already completely abrogates the binding of E2 to DNA sequences that harbour E2 binding domains (Prakash et al., 1992, Genes Dev 6: 105-16).

The resulting polypeptide is referred to as HPV16 E2E6E7SH and comprises SEQ ID NO: 3. A codon-optimized sequence encoding this polypeptide was prepared and is provided in SEQ ID NO: 4.

A variant was also constructed wherein the same E2 mutant protein was fused to the C-terminus of the HPV16 E6E7SH fusion polypeptide, giving rise to a polypeptide referred to as HPV16 E6E7E2SH, which comprises SEQ ID NO: 5. The sequence encoding this construct is provided as SEQ ID NO: 6.

For control purposes, we also constructed sequences encoding a polypeptide that contains the wild-type sequences for full-length HPV16 E6 and E7 as a fusion protein (E6 from aa 1 to 158 directly fused to E7 from aa 1 to 98, named herein E6E7 wt).

We also tested the effect of adding leader sequences to the polypeptide. As a non-limiting example, a sequence encoding an IgE leader sequence (see e.g. U.S. Pat. No. 6,733,994, the disclosure of which is incorporated herein by this reference) [the sequence of the leader peptide is provided in SEQ ID NO: 7] was fused at the N-terminus of some of the constructs, e.g. in the E6E7 wt construct, which rendered LSE6E7 wt, and in the E2E6E7SH construct, which rendered LSE2E6E7SH. The effect thereof was significantly (p<0.05) enhanced immunogenicity in comparison to the same antigen without the LS sequence as measured by E7-tetramer analysis in immunized mice (as can for instance be seen in FIG. 9).

The sequences that encode the E6E7SH polypeptides of the invention, with or without E2, can for instance be expressed from DNA constructs, from RNA or from viral vectors. FIG. 1 demonstrates expression in HEK-293T cells upon transient transfection with DNA vectors expressing the transgenes as described above. After transfection, cells were harvested and cell extracts were analyzed by SDS-PAGE and western blotting with an antibody against HPV16 E7. This experiment demonstrates expression of the expected fusion proteins of appropriate size upon transfection of the expression vectors.

Adenoviral vectors can be used to express the E6E7, either with or without E2, and with or without additional sequences to augment the immunogenicity of the encoded fusion protein.

The genes, coding for HPV16 E6E7 wt control or HPV16 designer sequences described above were gene optimized for human expression and synthesized, at Geneart. A Kozak sequence (5' GCCACC 3') was included directly in front of the ATG start codon, and two stop codons (5' TGA TAA 3') were added at the end of the respective coding sequence. The genes were inserted in the pAdApt35BSU plasmid and in the pAdApt26 plasmid (Havenga et al., 2006, J Gen Virol 87, 2135-43) via HindIII and XbaI sites.

All adenoviruses were generated in PER.C6 cells by single homologous recombination and produced as previously described (for rAd35: Havenga et al., 2006, J Gen Virol 87: 2135-43; for rAd26: Abbink et al., 2007, J Virol 81: 4654-63). PER.C6 cells (Fallaux et al., 1998, Hum Gene Ther 9: 1909-17) were maintained in Dulbecco's modified Eagle's medium (DMEM) with 10% fetal bovine serum (FBS), supplemented with 10 mM MgCl2.

Briefly, PER.C6 cells were transfected with Ad vector plasmids, using Lipofectamine according to the instructions provided by the manufacturer (Life Technologies). Cells were harvested one day after full cytopathic effect (CPE) was reached, freeze-thawed, centrifuged for 5 min at 3,000 rpm, and stored at −20° C. The viruses were plaque purified and amplified in PER.C6 cells cultured in a single well of a multiwell 24 tissue culture plate. Further amplification was carried out in PER.C6 cells cultured in a T25 tissue culture flask and subsequently in a T175 tissue culture flask. Of the crude lysate prepared from the cells obtained after the T175 flask, 3 to 5 ml was used to inoculate 24×T1000 five-layer tissue culture flasks containing 70% confluent layers of PER.C6 cells. The virus was purified using a two-step CsCl purification method. Finally, the virus was stored in aliquots at −85° C.

Ad35.HPV16-E6E7 wt, and Ad35.HPV16-E6E7SH are recombinant adenovirus serotype 35 (Ad35) vectors comprising the codon-optimized nucleotide sequences for the expression of, respectively, a fusion protein of the wild type HPV16 E6 and E7 proteins (E6E7 wt), and a designer fusion protein variant as described above (E6E7SH, having the amino acid sequence provided in SEQ ID NO: 1). The combined E6 and E7 sequences were placed under the control of a CMV promoter in the E1 region of the E1,E3 deleted adenovirus genome. Ad26.HPV16-E6E7 wt, and Ad26.HPV16-E6E7SH are the equivalent vectors based on recombinant adenovirus serotype 26.

Similarly, Ad26 and Ad35-based recombinant adenoviral vectors were produced that encode the HPV16 E2E6E7SH (SEQ ID NO: 3) variant. Likewise, Ad26 and Ad35 encoding the HPV16 E6E7E2SH (SEQ ID NO: 5) variant were produced. Also, an Ad35 vector encoding the E2E6E7SH fusion protein with an IgE leader sequence at the N-terminus was produced, named Ad35.HPV16-LSE2E6E7SH. Also a control adenovirus with the E6E7 wt fused to the IgE leader sequence at the N-terminus was produced.

The recombinant adenoviruses were produced on PER.C6 cells and purified by centrifugation on cesium chloride gradients.

Further examples of constructs that were coupled to repressor systems are provided in a later example below.

Example 2. Lack of Transforming Activity of the HPV16 Designer Constructs

Wild-type HPV16 E6 and E7 proteins have tumorigenic potential, which is apparent as transforming activity in certain assays, such as colony formation in a soft-agar assay (Massimi and Banks, 2005, *Methods Mol Med* 119: 381-395). The E6E7SH polypeptide as described in example 1 comprises the fragments of the E6 and E7 proteins in a re-ordered fashion. This is expected to remove the tumorigenic potential, as can be measured for instance by a significantly reduced transforming activity as compared to either of wt E6 and E7 proteins in such assays.

Others reported that gene-shuffled variants of HPV16 E6 and E7 have indeed lost their oncogenic potential (Öhlschläger et al., 2006, *Vaccine* 24: 2880-93; Henken et al., 2012, *Vaccine* 30: 4259-66), demonstrating that gene shuffling destroys the wild-type functions of E6 and E7 proteins.

Figure 2:
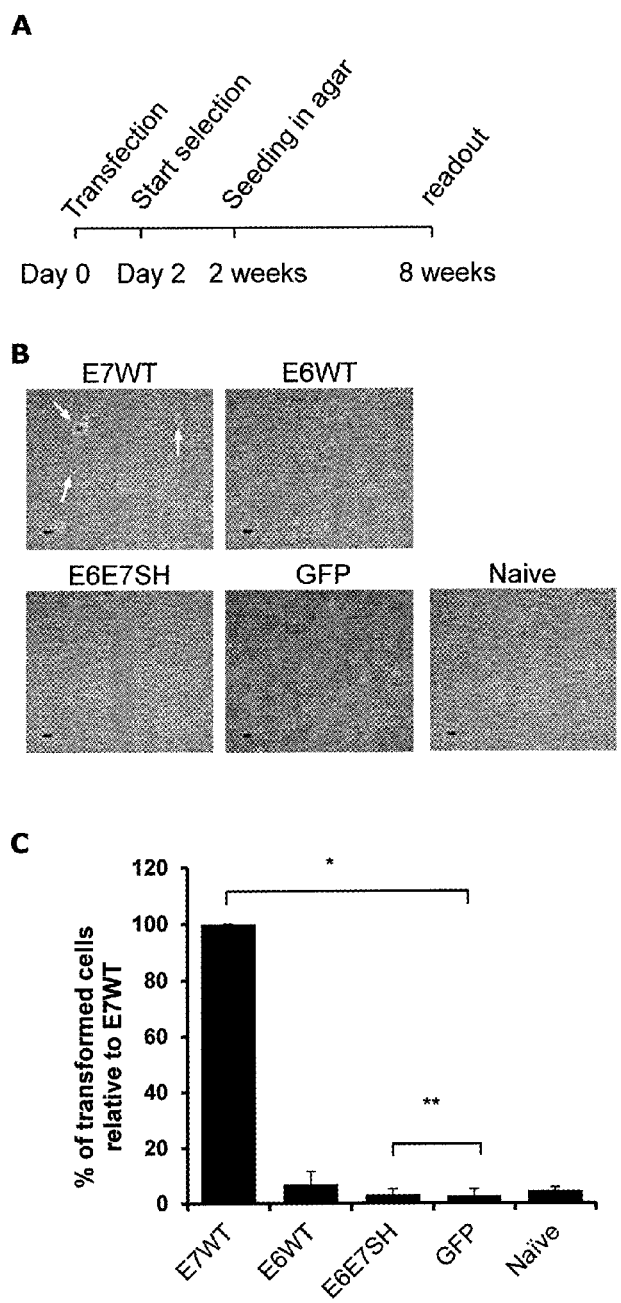
FIG. 2. Colony formation in soft agar. A) Schematic representation of the setup of the soft-agar assay. B) Representative microscopic images at 40× magnification of the cells in agar six weeks post seeding. The white arrows highlight colonies observed in the E7 wt transfected cells. C) Colony quantification six weeks post seeding in agar using the Gelcount™ and associated software. *: $p<0.05$ (Poisson regression model); **: non-inferior (generalized linear model with non-inferiority margin of 5%).

To assess the loss of tumorigenic properties, we assessed the ability of our E6E7SH constructs to confer the ability to grow in soft agar upon NIH 3T3 cells (as described by e.g. Massimi and Banks, 2005, *Methods Mol Med* 119: 381-395). Transfection of NIH3T3 cells with a plasmid expressing the wild type HPV16 E7 resulted consistently in colony formation. In these assays, expression of wild type HPV16 E6 alone did not cause colony formation above background. This is in line with published observations that E7 wt is much more efficient than E6 wt in this assay (Sedman et al., 1991, *J Virol* 65: 4860-66). Transfection with our E6E7SH construct did not lead to growth of colonies of cells in soft agar (FIG. 2) in four independent experiments, demonstrating that nucleic acids encoding a polypeptide of the disclosure, E6E7SH, have lost the transforming capacity that is associated with E7.

Figure 3:
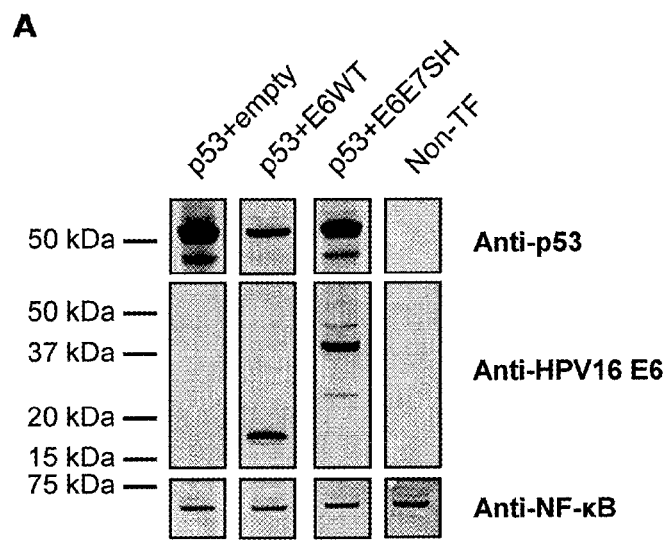
FIG. 3. HPV16 E6E7SH has lost E6 and E7 activities. A) Representative western blot demonstrating absence of p53 degradation by E6E7SH. Human p53 null NCI-H1299 cells were co-transfected with a plasmid expressing p53 in combination with a plasmid expressing HPV16 E6 wild-type, HPV16 E6E7SH or the empty vector. Non-TF indicates non-transfected cells. 24 hours after transfection cell lysates were prepared and 30 µg of total protein was loaded on gel. Upper panel—p53 staining, middle panel—E6 staining, lower panel—NF-κB staining (loading control). (B) Quantification of p53 levels in four independent assays. The p53 signal was normalized to the NF-κB signal. C) Western blot demonstrating lack of pRb degradation by E6E7SH. pRb null Saos-2 cells were transfected with a plasmid expressing pRb in combination with a plasmid expressing HPV16 E7 wild-type, HPV16 E6E7SH or the empty vector. Non-TF indicates non-transfected cells. 24 hours after transfection cell lysates were prepared and 10 µg of total protein was loaded on gel. Upper panel—pRb staining, middle panel—E7 staining, lower panel—NF-κB staining (loading control). D) Quantification of pRb levels in four independent assays. The pRb signal was normalized to the NF-κB signal. *: $p<0.05$ (ANOVA models); **: non-inferior (testing was based on 95% CI's derived from ANOVA models. Non-inferiority margin was set at 75%).
Figure 3:
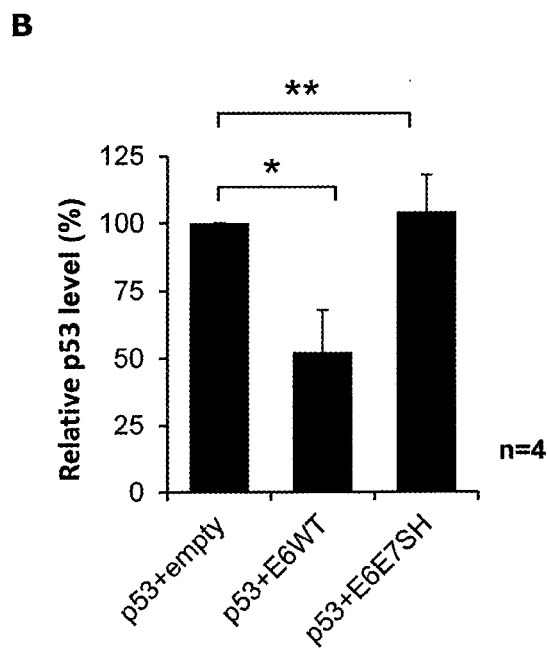

The tumorigenic potential of E6 and E7 is associated with their ability to reduce the levels of the cellular proteins p53 and pRb respectively. p53 and pRb degradation assays were performed to demonstrate that nucleic acid encoding a polypeptide of the disclosure, E6E7SH, construct does not have the biological activity associated with the wild-type E6 and E7 at the molecular level. In short, HPV16 E6 wt and our E6E7SH construct were expressed in NCI-H1299 cells that lack endogenous p53 for the p53 degradation assay. For the pRb degradation assay HPV16 E7 wt and the E6E7SH construct were expressed in pRb null Saos-2 cells. As can be seen in FIG. 3, co-expression of p53 with E6 wt, but not with E6E7SH, leads to reduced p53 levels (panels A and B). Likewise, panels 3C and 3D show that co-expression of pRb with E7 wt, but not with E6E7SH, leads to reduced pRB levels. These data demonstrate that nucleic acid encoding a polypeptide of the disclosure has no ability to form colonies in soft agar and does not contain main biological activities of the wild-type E6 and E7 polypeptides, namely the inactivation of p53 and pRb respectively.

Figure 4:
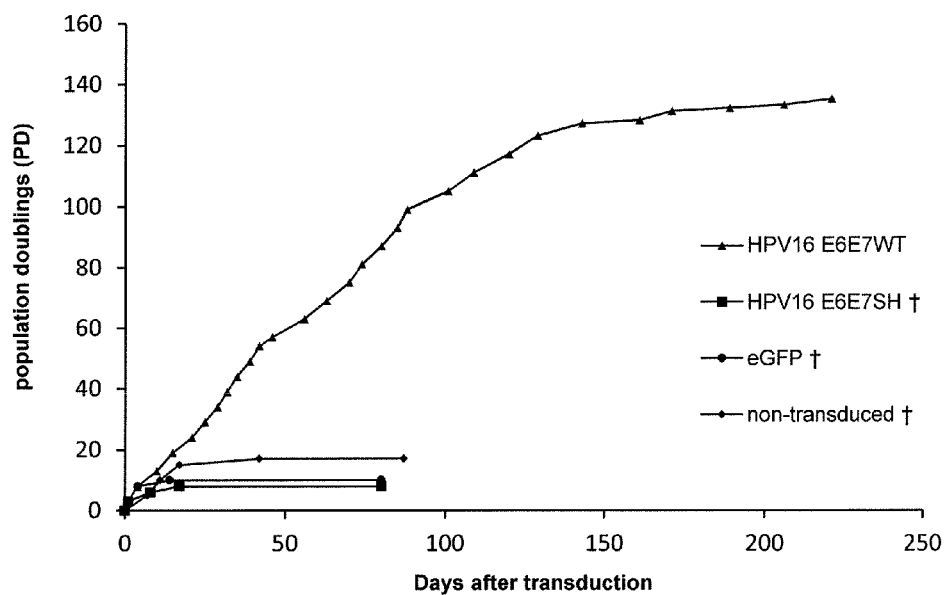
FIG. 4. HPV16 E6E7SH does not immortalize primary human epidermal keratinocytes. Primary human epidermal keratinocytes were transduced with lentiviruses encoding either the wild-type E6- and E7-encoding open reading frame of HPV16 (E6E7 wt), the HPV16 E6E7SH sequence or eGFP. Non-transduced donor cells were used as a control. Only expression of E6E7 wt induces immortalization of primary keratinocytes as indicated by the extended lifespan and hTERT activation around day 200 (not shown). The cross symbol indicates that the cells died in senescence and could not be further cultured. For details see example 2. Similar results were obtained in two additional donors (not shown).

To further demonstrate the safety of nucleic acid constructs encoding polypeptide of the disclosure, we made use of primary human foreskin keratinocytes that are the natural target cells for HPV mediated transformation. Immortalization of primary human keratinocytes requires the action of both E6 and E7 wild-type (Munger et al., 1989, *J Virol* 63: 4417-21). This assay is probably the physiologically most relevant in vitro assay to demonstrate the safety of our constructs (Massimi and Banks, 2005, *Methods Mol Med* 119: 381-395). Cells transduced with lentiviruses expressing wild type E6 and E7 from HPV16 (E6E7 wt) induce immortalization in primary keratinocytes as indicated by the extension of their lifespan as compared to non-transduced control cells (FIG. 4) and activation of hTERT, the catalytic subunit of telomerase (data not shown). Expression of the polypeptide of the disclosure (E6E7SH) is not able to extend the lifespan compared to GFP-transduced or non-transduced keratinocytes. A similar result was obtained in two additional independent donors (data not shown). Taken together these data demonstrate that our constructs have lost the ability to induce immortalization in primary human keratinocytes, that are considered a highly physiological model.

Another construct wherein comparable fragments of HPV16 E6 and E7 were recombined in a different order was also incapable of immortalization of primary human foreskin keratinocytes. However, an expanded life span up to approximately 120-150 days was observed for that construct. This indicates some unpredictability in this field, and demonstrates the superiority of the selected designer molecules of the disclosure in this safety-related aspect.

All together the experiments in this example provide strong evidence of the lack of transforming activity of nucleic acids encoding HPV16 designer polypeptides of the disclosure, and thus a strongly improved safety over HPV16 E6 and E7 wt constructs.

Example 3. Immune Responses to the HPV16 E6E7SH Designer Constructs

DNA vectors and adenoviral vectors were prepared, as described in Example 1.

Figure 5:
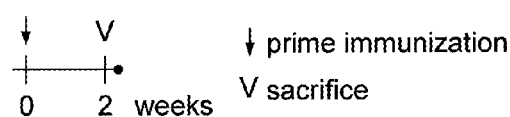
FIG. 5. Immune response induced by HPV16 E6E7SH after DNA immunization—IFNγ ELISPOT analysis. A. Immunization scheme. CB6F1 mice were immunized with DNA plasmids expressing HPV16 E6E7SH or a plasmid expressing no transgene (control). Two weeks after immunization the mice were sacrificed and isolated splenocytes were stimulated overnight with 15mer peptide pools corresponding to E7. B. HPV16 E7-specific immune responses in individual mice as measured by IFNγ ELISPOT assays are given as spot forming units (SFU) per $10^6$ splenocytes.
Figure 5:
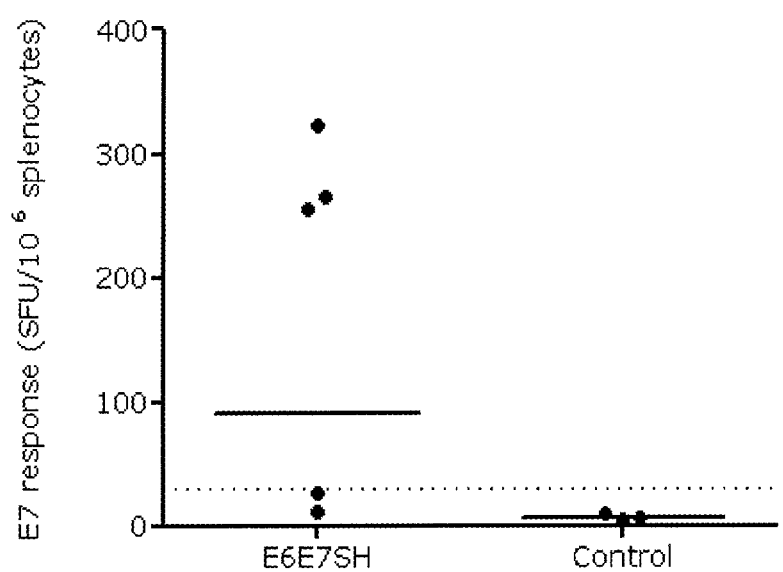

The CB6F1 mouse strain was used for measuring immune responses, based on initial experiments where mice where immunized with DNA plasmids encoding wild type E2, or E6 or E7, and immunization with HPV16 E2, E6 and E7 antigens induced a broader cellular immune response in CB6F1 than in C57BL/6 mice or Balb/c mice. In a separate experiment mice were immunized with DNA vectors encoding molecules of the disclosure and cellular immune responses were measured. HPV16 E7-specific immune responses could be measured in mice immunized with DNA plasmids expressing E6E7SH (FIG. 5).

The following data shown in this example are from mouse experiments that were carried out with adenoviral vectors.

To evaluate the vaccine induced immunogenicity, CB6F1 mice were immunized with adenovectors (Ad35) expressing HPV16 E6E7wt, LSE6E7wt, E6E7SH or adenovectors not encoding a transgene (Empty). Two doses were tested for administration to the mice: $5*10^9$ viral particles (vp) and $1*10^{10}$ vp. Two and eight weeks after immunization the mice were sacrificed and isolated splenocytes were stimulated overnight with an HPV16 E7 15mer peptide pool. E7-specific responses at two weeks and at eight weeks were analyzed by IFNγ ELISPOT. The data are presented in FIG. 6.

This shows that immunization of mice with Ad35.HPV16-E6E7SH induces E7-specific immune responses as measured by ELISPOT analysis. In addition, the results in FIG. 6 demonstrates the possibility to enhance the immune response against an adenoviral expressed transgene by adding an N-terminal leader sequence to the transgene.

Figure 7:
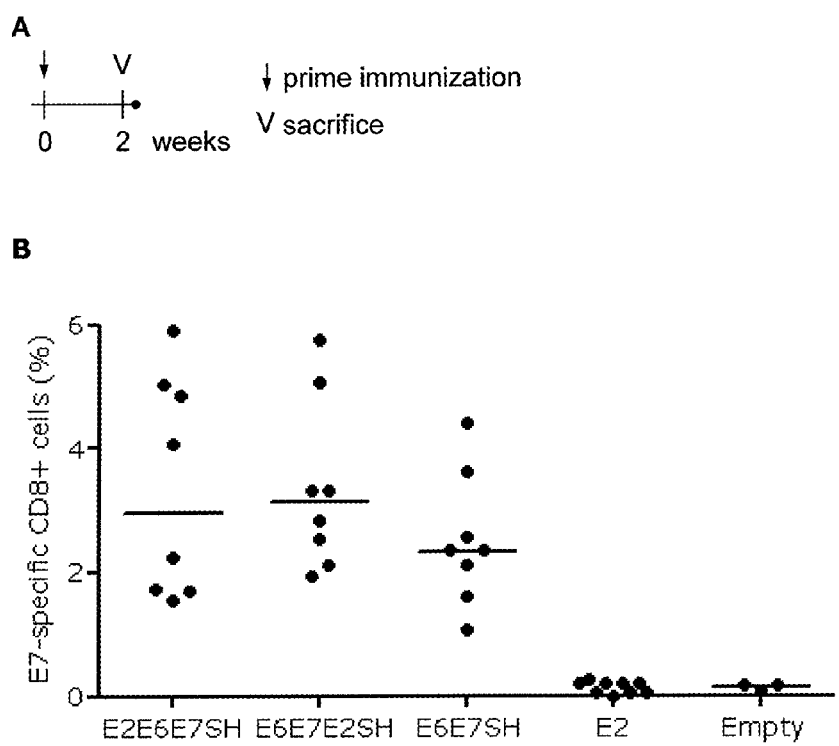
FIG. 7. Immunogenicity of HPV16 E2E6E7SH—E7-tetramer staining. (A). Immunization scheme. CB6F1 mice were immunized with $1*10^{10}$ vp of adenovectors expressing the transgenes as indicated. Two weeks after immunization the mice were sacrificed and isolated splenocytes analyzed for the presence of CD8+ cells capable of interacting with $E7_{49-57}$-H2-Db tetramers (B). The percentage of E7-tetramer positive CD8+ T-cells is indicated on the y-axis. ANOVA Post-hoc Bonferroni statistical analysis was performed on log transformed data, the differences between the different E6E7SH variants were not statistically significant.

Next the effect of adding HPV16 E2 to the HPV16 E6E7SH polypeptide with respect to immunogenicity was tested. The Ad35 vectors encoded polypeptides that had E2 either fused to the N-terminus (E2E6E7SH) or to the C-terminus (E6E7E2SH). CB6F1 mice were immunized with a dose of 1×10$^{10}$ vp. FIG. 7 (E7-tetramer staining) and FIG. 8 (Panel C, IFNγ ELISPOT) show the immune responses against E7, which for the designer constructs including E2 tends to be higher in comparison to the construct without E2, although the differences were not statistically significant. The response against E2 was higher for adenoviral vectors encoding only E2 compared to the response for adenoviral vectors that had E2 fused to the E6E7SH designer polypeptide (FIG. 8B), with differences being significant for both E2 vs E2E6E7SH and E2 vs E6E7E2SH (p-value: <0.05).

It is concluded that the designer constructs that further include E2 can still provide an immune response against E7, and in addition also provide an immune response against E2, thus increasing the breadth of the immune response over the constructs that do not include E2.

Figure 8:
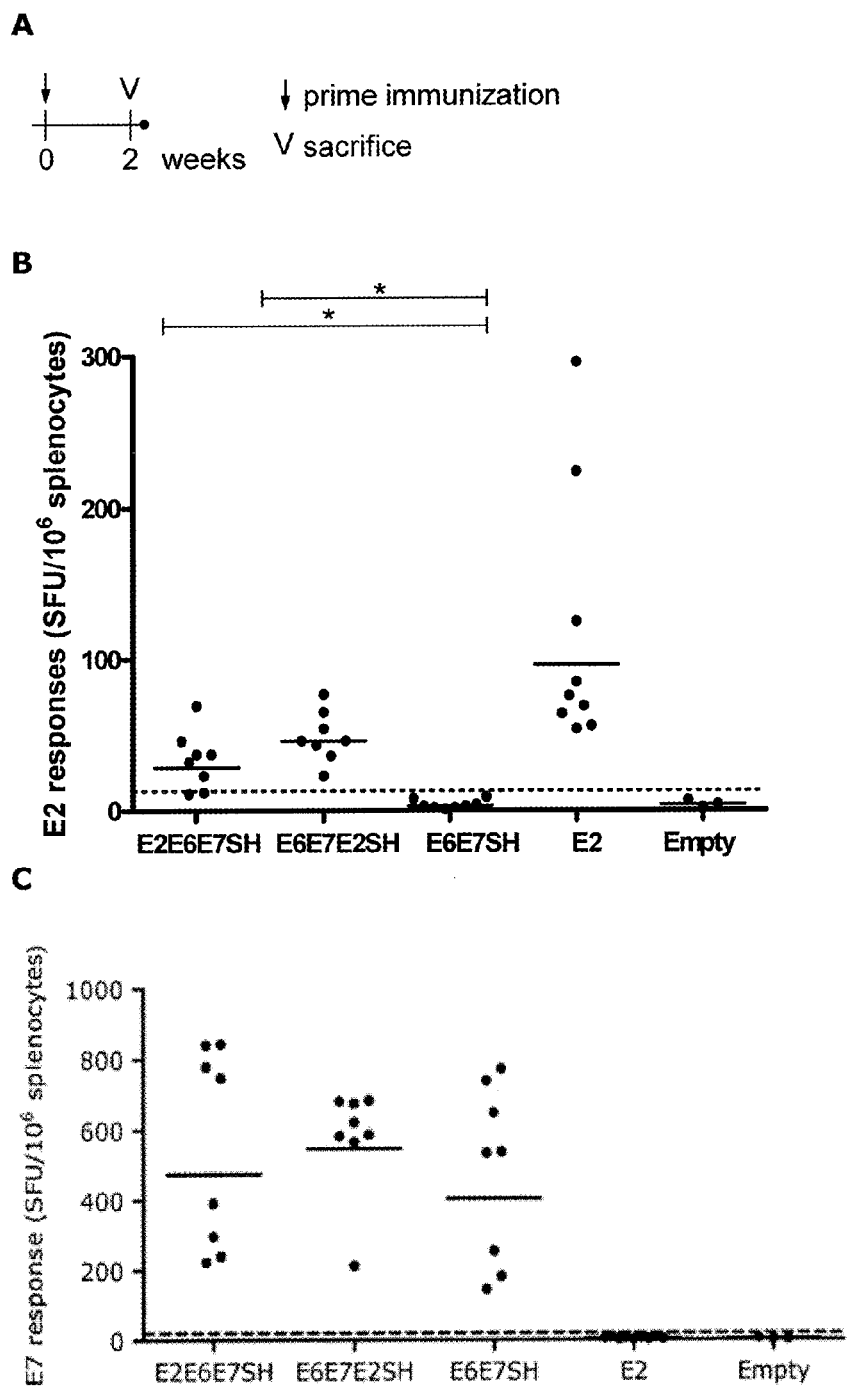
FIG. 8. Immunogenicity of HPV16 E2E6E7SH—IFNγ ELISPOT analysis. (A). Immunization scheme. CB6F1 mice were immunized with adenovectors expressing the transgenes indicated below panels B and C. Two weeks after immunization the mice were sacrificed and isolated splenocytes were stimulated overnight with 15mer peptide pools corresponding to E2 (B), E6 (not shown) or E7 (C). Responses are given as SFU per $10^6$ splenocytes. ANOVA Post-hoc Bonferroni statistical analysis was performed on log transformed data. The E2 response induced by Adenovectors encoding E2 alone is higher than the response induced by the polypeptides of the invention that include the E6 and E7 fragments. The difference is significant for E2 vs E2E6E7SH and E2 vs E6E7E2SH (*: p<0.05). ANOVA Post-hoc Bonferroni statistical analysis was performed on log transformed data.
Figure 9:
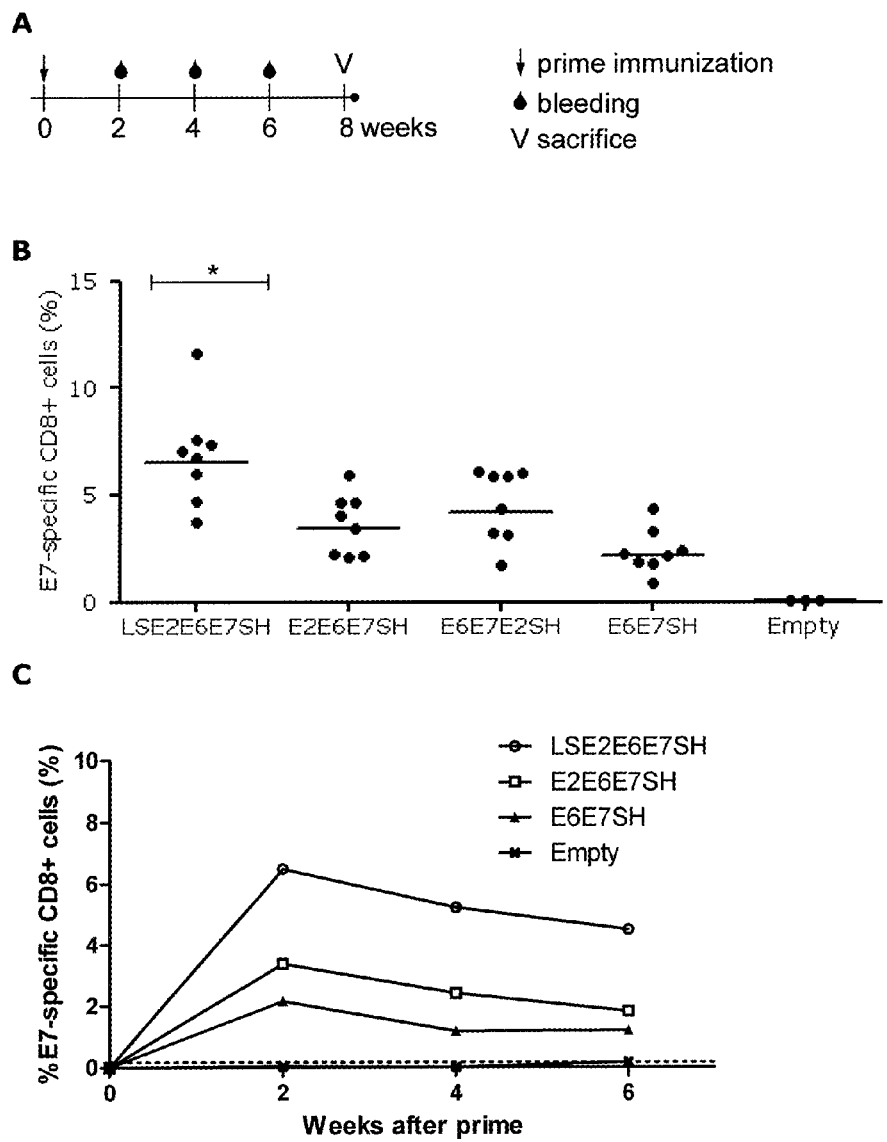
FIG. 9. Sustained HPV16 immune responses in immunized mice. (A) Immunization scheme. CB6F1 mice were immunized with $1*10^{10}$ vp of Ad35 vectors expressing variants HPV16 LSE2E6E7SH, HPV16 E2E6E7SH, HPV16 E6E7SH, or with an adenovector not expressing a transgene (Empty). Blood samples were taken every two weeks to determine the percentage E7-specific CD8+ T-cells by tetramer staining. (B) Immune responses two weeks after immunization. The vector including a leader sequence induced a higher response than vectors without the leader sequence; LSE2E6E7SH vs E2E6E7SH (*: p<0.05). (C) Kinetics of the responses. ANOVA Post-hoc Bonferroni statistical analysis was performed on log transformed data of the week 2 data set. The E7 response induced by molecules including E2 tend to be higher compared to the molecule without E2, though the results were not statistically significant.

Addition of a leader sequence was shown to result in higher E7-specific responses when fused to the N-terminus of the fusion protein of wild type E6 and E7 (FIG. 6C). Similarly, the effect of the leader sequence on immunogenicity of the E2E6E7SH fusion protein was determined. Therefore, Ad35 vectors encoding the HPV16 designer polypeptide, with or without N-terminal E2 and an Ad35 vector encoding LSE2E6E7SH were used for immunization of mice and blood samples were taken at two-week intervals to measure E7-specific immune responses (FIG. 9). As shown in FIGS. 7 and 8 the presence of E2 at either N- or C-terminally fused to E6E7SH tended to increase the immune responses. Addition of the IgE leader sequence further increased the E7-specific response (FIG. 9B). Over time sustained immune responses were observed for all three adenoviral vectors that encoded designer molecules of the disclosure, and the highest response after the immunization corresponded with the highest responses over the duration of the experiment.

It is concluded that the responses that are induced by the designer construct that further includes N-terminal E2 can be increased by addition of specific sequences, e.g., the IgE leader sequence, that target the encoded protein to specific cellular compartments.

Figure 10:
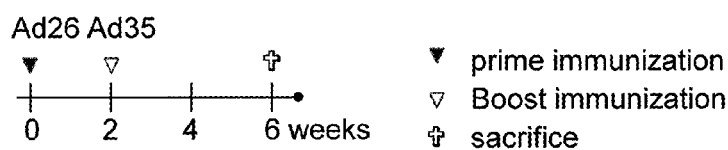
FIG. 10. Use of different Adenoviral vectors to boost immune responses. (A). Immunization scheme. CB6F1 mice were immunized with an Ad26 vector expressing HPV16 E2E6E7SH (HPV16-Tx) or with an Ad26 vector expressing no transgene (empty). Two weeks later the immunizations were repeated with Ad35-based vectors as indicated below the figure. Four weeks after the second immunization the mice were sacrificed and blood samples were used to determine the percentage of E7-specific CD8+ T-cells by tetramer staining (B). * indicates the comparison of Ad26.HPV16-Tx/Ad35.HPV16-Tx versus Ad26.HPV16-Tx/Ad35.Empty, p<0.05 (student t-test on log transformed data, with alpha=0.01 for multiple comparisons).
Figure 10:
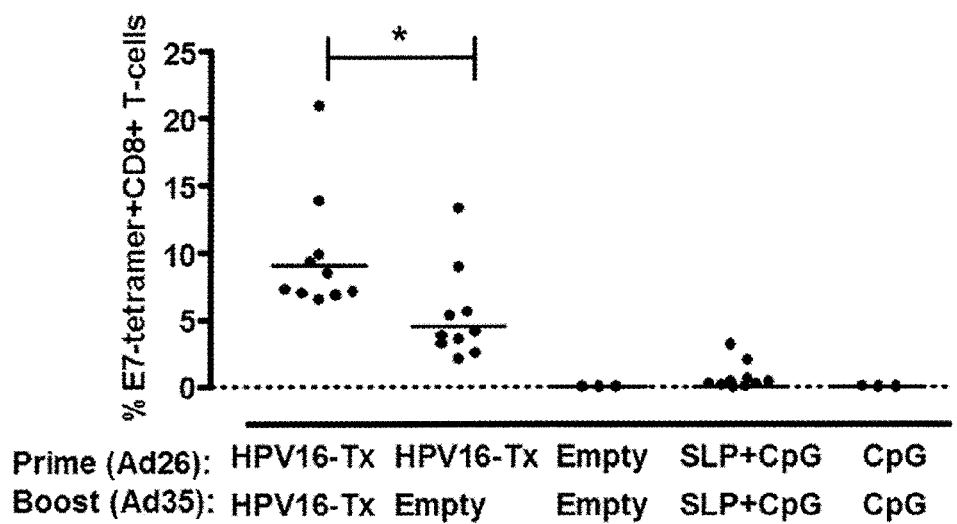

The cellular immune response against the peptide of the invention can be induced with different types of adenoviral vectors. In the previous experiment we used Ad35 vectors, while in the experiment of FIG. 10, mice were immunized with an Ad26 adenoviral vector expressing HPV16 E2E6E7SH. The data show that also immunization with an Ad26-based vaccine induced E7-specific T-cells. In addition, the results demonstrate that a second immunization with an Ad35 adenoviral vector expressing HPV16 E2E6E7SH further boosted the cellular immune responses (FIG. 10).

Example 4. Immunogenicity of HPV16 Designer Constructs in Rhesus Macaques

Figure 11:
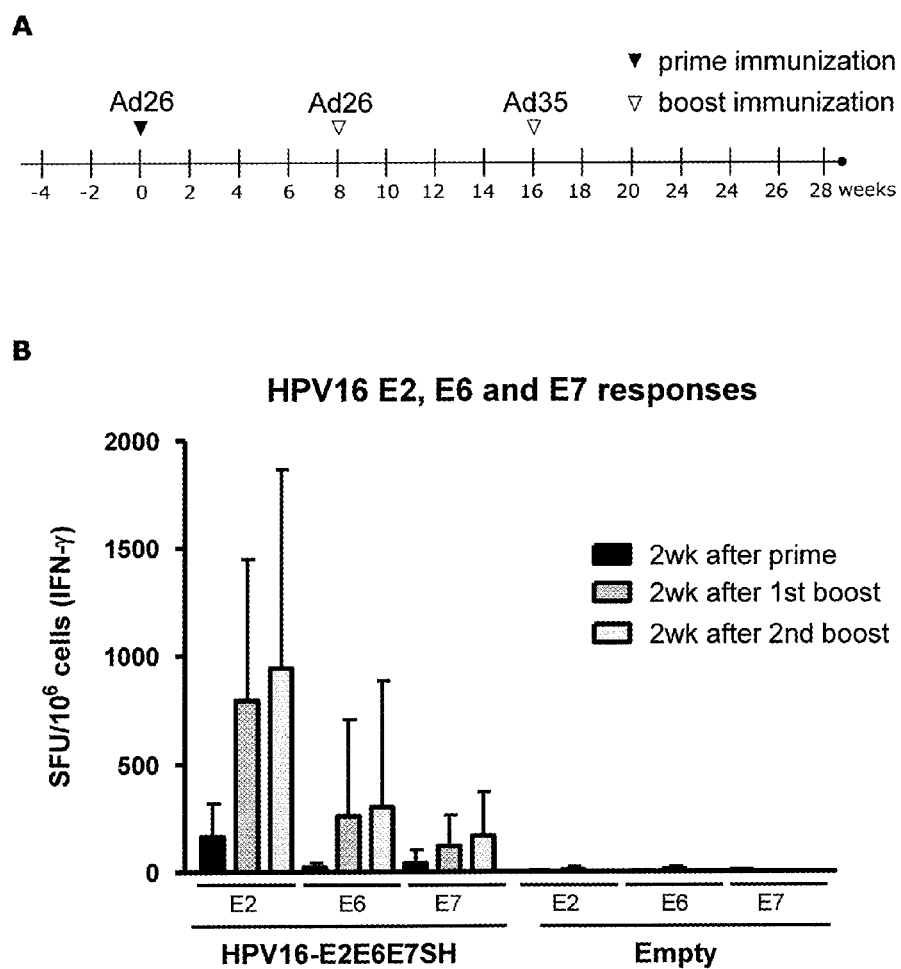
FIG. 11. Cellular immunogenicity of HPV16 E2E6E7SH in Rhesus macaques. (A) Immunization scheme. Rhesus macaques were immunized at day 0: Eight animals received Ad26.HPV16-E2E6E7SH and two control animals received Ad26.Empty by intramuscular immunization (i.m). A boost immunization was given (Ad26.HPV16-E2E6E7SH or Ad26.Empty) at 8 weeks. At 16 weeks, animals received a second boost immunization with Ad35 vectors expressing the same HPV16 E2E6E7SH, while control animals received Ad35.Empty. The dose of adenovectors was $1*10^{11}$ vp per immunization. Blood drawings were performed at several time points. (B) Cellular immune responses in PBMCs were measured by IFNγ ELISPOT. PBMCs were stimulated with peptide pools corresponding to HPV16 E2, E6 or E7 and the number of spot-forming units (SFU) in $1*10^6$ PBMCs are depicted. The empty control animal (n=2) showed no detectable response. For details see example 4.

To evaluate the ability of the adenoviral vectors expressing the designer sequence of the invention to induce immune responses in non-human primates, rhesus macaques were immunized by intramuscular injection with adenovectors (Ad26) expressing HPV16 E2E6E7SH or adenovectors not encoding a transgene (Empty), with a dose of 1*10$^{11}$ vp. Eight weeks after the immunization the immune responses were boosted by immunization with Ad26 vectors expressing the same antigen. At week 16 the animals received one more injection with the Ad35 vectors expressing the same antigen. Blood samples were taken at several time points and isolated white blood cells were stimulated overnight with a peptide pools corresponding to HPV16 E2, E6 or E7. Specific responses were measured by IFNγ ELISPOT. The data are presented in FIG. 11. In addition at week 10 and week 18 post prime immunization, the cellular immune response specific to peptides spanning the novel junctions in the invention was evaluated. The induction of IFNγ response was in all animals below the limit of detection of <50 SFU per 1*10$^6$ PBMC (data not shown).

The data show that immunization of non-human primates with Ad26.HPV16-E2E6E7SH resulted in cellular immune responses against all three HPV16 proteins that are present in the encoded transgene, but not against the novel junctions. Responses could be boosted by the additional immunization with Ad26.HPV16-E2E6E7SH and additional boost at week 16 with the corresponding Ad35 vector further increased the HPV16 E2, E6 and E7-specific immune responses.

In a separate experiment (not shown), Rhesus macaques were immunized by intravaginal administration with a combination of two adenoviral vectors, one expressing HPV16 E6E7SH and the other the HPV16 L1 protein. Low but measurable cellular responses were measured in peripheral mononuclear blood cells against both E6 and E7. In these experiments, strong cellular immune responses against L1 were detected.

Example 5. Therapeutic Efficacy in a Mouse Tumor Model

The polypeptide of the disclosure for HPV16 (comprising SEQ ID NO: 1) is capable of inducing HPV16-specific cellular immune response in animals, which can exert a therapeutic effect on cells expressing HPV16 E6 and/or E7. Therapeutic immunization, i.e. immunization after tumor growth has started, can be used to demonstrate efficacy of a therapeutic HPV vaccine candidate. The therapeutic effect of Ad26 and Ad35 vectors was tested in mice that were injected with TC-1 cells (mouse cells expressing HPV16 E6 and E7) (Lin et al., 1996, *Cancer Res* 56: 21-6). TC-1 cells will form solid tumor within a few days to weeks after sub-cutaneous injection in mice. Without vaccine the tumors grew rapidly and reach a pre-determined size of 1000 mm$^3$ within 30 days (panels D and E). Upon reaching this size the mice are sacrificed for ethical reasons.

Figure 12:
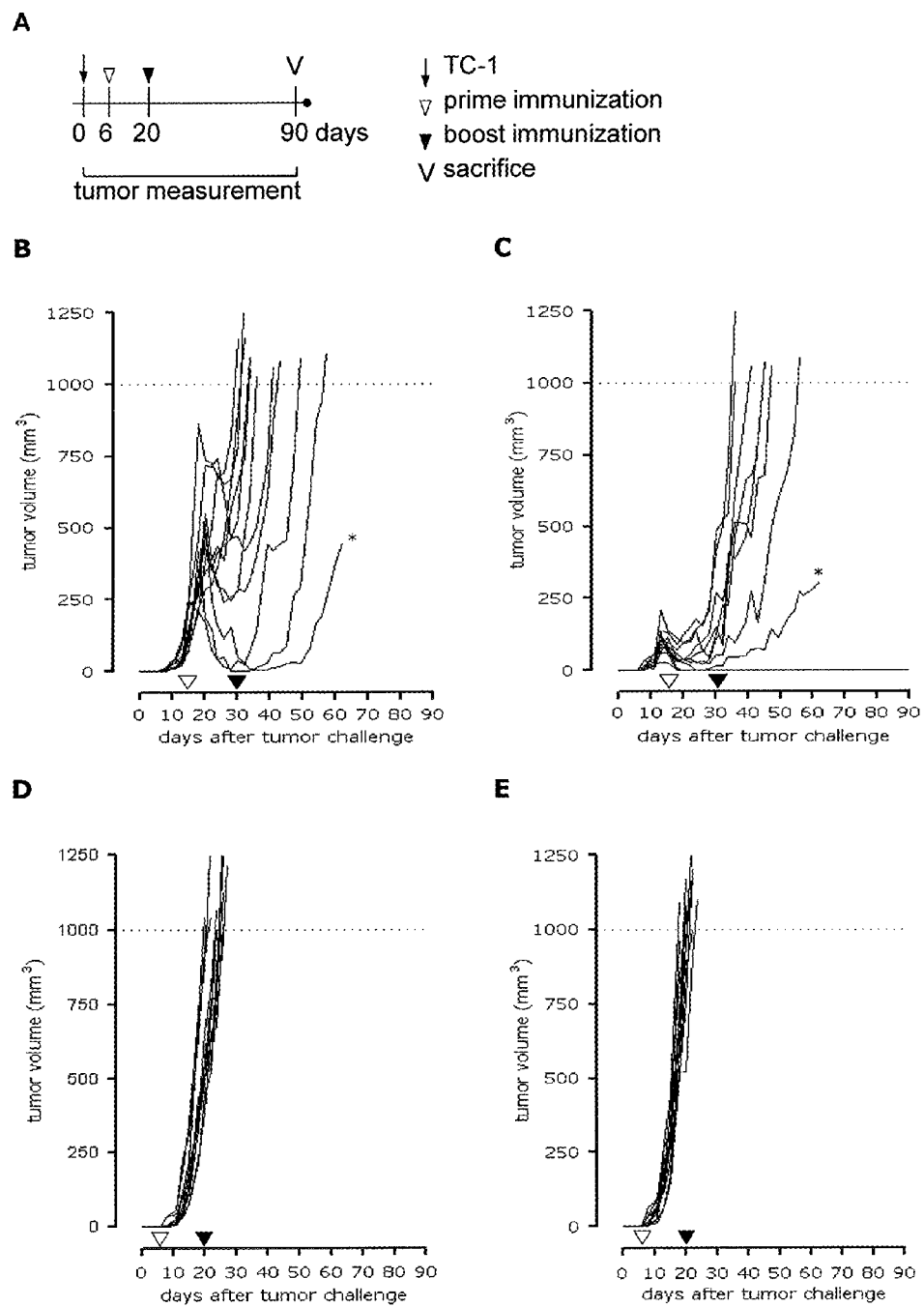
FIG. 12. Therapeutic effect of Adenovectors expressing HPV16-E2E6E7SH. (A) TC-1 injection and immunization scheme. CB6F1 mice were injected sub-cutaneously with $1*10^5$ TC-1 cells at day 0. After six days, when tumors were palpable, mice were immunized with two SLPs covering HPV16 E6 and E7 immunodominant epitopes (i.e., HPV16 E6, aa41-65 (KQQLLRREVYDFAFRDLCIVYRDGN; SEQ ID NO: 18) and HPV16 E7 aa 43-77 (GQAEPDRAHYNIVTFCCKCDSTLRLCVQSTHVDIR; SEQ ID NO: 19)) at 150 μg in a final volume of 200 μl 0.9% saline supplemented with 5 nmol ODN1826-CpG (B) or Ad26.HPV16-E2E6E7SH (C). Control mice received either CpG alone (D) or Ad26.Empty (E). All mice received a boost immunization at day 20. Mice that received Ad26 vectors in the prime immunization were subsequently immunized with the corresponding Ad35 vectors. The other mice received, SLP adjuvanted with CpG or CpG alone as in the prime immunizations. (B-E) Tumor measurement in TC-1 injected mice. Tumor volume was calculated as (width$^2$*length)/2. Mice were sacrificed when tumor volumes surpassed 1000 mm$^3$. Two mice had to be sacrificed due to weight loss of more than 20% (indicated with asterisks). (F-G) Close up of panels B and C for first 35 days. (H) Survival after TC-1 injection. The survival of mice treated with Ad.HPV16-E2E6E7SH was significantly increased compared with mice immunized with SLP and CpG (Log-rank test p<0.05). Three mice immunized with the Ad.HPV16-E2E6E7SH were tumor free at the end of the experiment (at day 92).

With a prime-boost immunization scheme with SLPs (used as a positive control; Kenter et al., 2009, *N Engl J Med* 361:1838-47; Zwaveling et al., 2002, *J Immunol* 169:350-8) or adenoviral vectors expressing HPV16-E2E6E7SH, a marked decrease of the growth of TC-1 induced tumors was observed (FIG. 12, panels B and C). Closer inspection of the first 30 days after the prime immunizations (Panels F and G) shows that the immunization with the adenovectors expressing E2E6E7SH have a substantially larger impact on tumor growth than immunization with the SLPs. The initial growth rate is much lower and in most cases the tumors shrunk. In 3 out of 11 mice immunized with the adenoviral vectors, the tumors were completely eradicated, which is reflected in the survival plot (panel H).

In conclusion, immunization with adenoviral vectors expressing an HPV16 designer polypeptide of the disclosure significantly reduced tumor growth or completely eradicated established tumors in a well-established challenge model for HPV16-induced cancer.

Example 6: Employment of Repressor Systems to Improve the Productivity and Genetic Stability of Adenoviral Vectors Expressing HPV-Derived Antigens It has previously been reported that transgenes inserted into adenovirus vectors under the control of powerful constitutively active promoters can, depending on the properties of the transgene product, negatively impact vector production (Yoshida & Yamada, 1997, *Biochem Biophys Res Commun* 230:426-30; Rubinchik et al., 2000, *Gene Ther* 7:875-85; Matthews et al., 1999, *J Gen Virol* 80:345-53; Edholm et al., 2001, *J Virol* 75:9579-84; Gall et al., 2007, *Mol Biotechnol* 35:263-73). Examples of transgene-dependent vector productivity issues include inefficient vector rescue and growth, low final vector yields, and, in severe cases, rapid outgrowth of viral mutants with defective transgene cassettes. To solve these issues, multiple studies explored the possibility to silence vector transgene expression during vector replication in producer cells (Matthews et al., 1999, *J Gen Virol* 80:345-53; Edholm et al., 2001, *J Virol* 75:9579-84; Gall et al., 2007, *Mol Biotechnol* 35:263-73; Cottingham et al., 2012, *Biotechnol Bioeng* 109:719-28; Gilbert et al., 2014, *J Virol Methods* 208:177-88). In this regard, different repression systems have previously been implemented in the context of Ad vectors and have indeed shown to improve vector productivity and genetic stability for vectors encoding different types of (inhibitory) transgenes.

It was observed that some of the adenovirus vectors described herein, as well as some other adenoviral vectors encoding certain HPV antigen variants, displayed some of the transgene-dependent vector productivity issues described above, and therefore could possibly be further improved in that respect. We therefore sought to investigate whether usage of systems to repress vector transgene expression can improve production characteristics of Ad vectors expressing HPV-derived antigens as those described herein. For this purpose, we implemented two existing repressor-operator systems, i.e. TetR/TetO (Yao & Eriksson, 1999, *Hum Gene Ther* 10:419-22, EP0990041B1) and CymR/CuO (Mullick et al., 2006, *BMC Biotechnol* 6:43), into our adenovirus vector platform. Both the TetR/TetO and the CymR/CuO system have previously been used by others to improve adenovirus vector productivity through vector transgene silencing during vector replication (Gall et al., 2007, *Mol Biotechnol* 35:263-73; Cottingham et al., 2012, *Biotechnol Bioeng* 109:719-28; Gilbert et al., 2014, *J Virol Methods* 208:177-88). Implementation of these two systems involved the generation of adenoviral vectors expressing genes of interest under the control of either a TetO or a CuO sequence-containing CMV promoter. Furthermore, the implementation entailed the generation of cell lines stably expressing the respective cognate repressors proteins (i.e. TetR or CymR).

Several E1-deleted, Ad26- and Ad35-based vectors were generated in which sequences encoding heterologous polypeptides were operably linked to a CMV promoter containing either TetO or CuO operator sequences. First, certain TetO- or CuO-containing sequences (SEQ ID NO: 11 and SEQ ID NO: 12, respectively) were inserted near the transcription start site (TSS) of the CMV promoter (SEQ ID NO: 13) of pAdapt26 and pAdapt35.Bsu plasmids (Abbink et al., 2007, *J Virol* 81:4654-63; Havenga et al., 2006, *J Gen Virol* 87:2135-43). The operator-containing sequences were inserted at precisely the same positions of the CMV promoter as previously described for the two systems (Yao & Eriksson, 1999, *Human Gene Ther* 10:419-22; EP0990041B1; Mullick et al., 2006, *BMC Biotechnol* 6:43; EP1385946 B1). Specifically, relative to the TSS (as originally assigned; Stenberg et al. 1984, *J Virol* 49:190-9), the TetO- and CuO-containing sequences were inserted directly downstream of positions −20 and +7, respectively. In SEQ ID NO: 13, these two positions correspond to positions 716 and 742, respectively. The resulting operator-containing CMV promoters are termed, respectively, CMVTetO and CMVCuO. Next, different transgenes were inserted downstream of the (modified) CMV promoters of the resulting constructs using HindIII and XbaI restriction sites. These transgenes included genes encoding a fusion protein of green fluorescent protein and luciferase (GFP-Luc), HPV16 LSE2E6E7SH as described above in example 1, and another polypeptide with some similarity to HPV16 LSE2E6E7SH (a construct referred to in this example as 'HPVAg'). HPVAg comprises the same leader sequence as present in LSE2E6E7SH, as well as E2, E6, and E7 sequences of HPV16. Using methods as described herein, the resulting modified pAdapt26 and pAdapt35.Bsu plasmids were used for the generation of adenoviral vectors expressing the above mentioned reporter and HPV transgenes under the control of either the CMVTetO or the CMVCuO promoter.

Cell lines expressing either TetR or CymR were generated by stable transfection of PER.C60 cells using, respectively, plasmid pcDNA™6/TR (LifeTechnologies, V1025-20) and a derivative of pcDNA™6/TR in which the TetR-coding sequence (SEQ ID NO: 14, which encodes polypeptide SEQ ID NO: 15) is replaced by a codon-optimized CymR-coding sequence (SEQ ID NO: 16, which encodes polypeptide SEQ ID NO: 17). Stable cell line generation was performed largely as described by the supplier of pcDNA™6/TR using a transient transfection-based assay to screen for cell clones capable of repressing expression of CMVTetO- or CMVCuO-driven genes. The resulting PER.C6/TetR and PER.C6/CymR cell lines were analyzed for their ability to repress transgene expression during vector replication in these cells. Experiments conducted with vectors expressing GFP-Luc under the control of operator-containing CMV-promoters showed at least a 10-fold reduction of luciferase gene expression throughout the complete virus replication cycle in the cell lines expressing the repressor corresponding to the respective operator sequences (data not shown). This confirmed that the PER.C6/TetR and PER.C6/CymR cell lines were capable of repressing vector transgene expression in the context of replicating adenovirus vectors.

Figure 13:
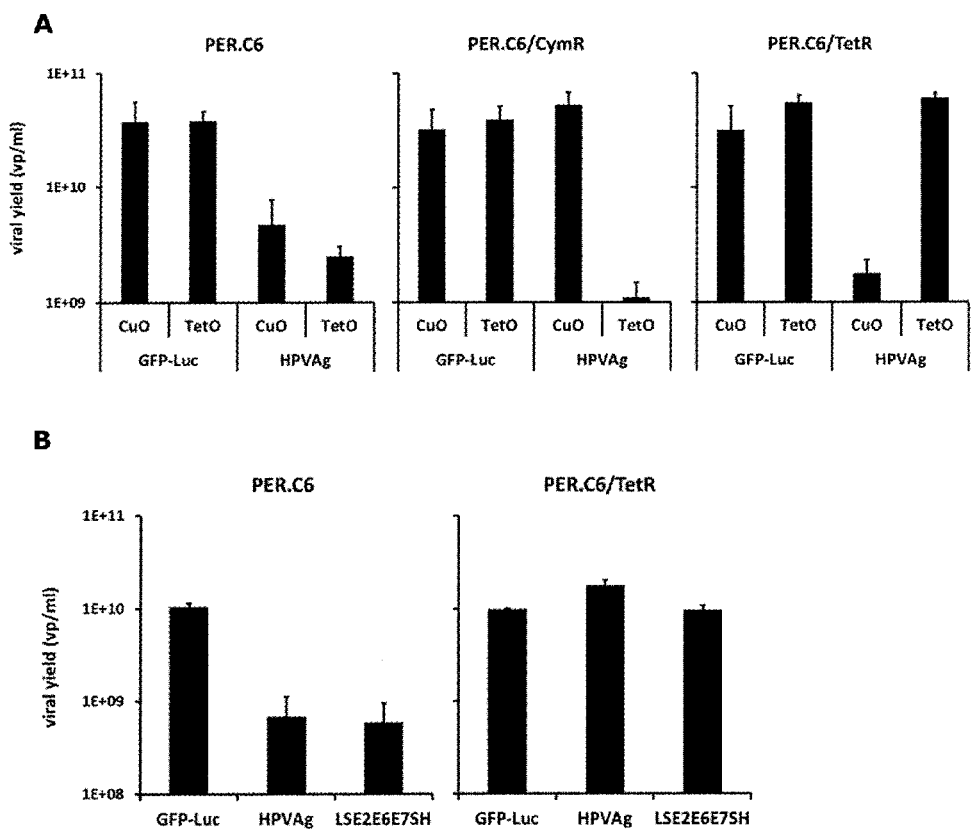
FIG. 13. Adenoviral vectors carrying transgenes encoding either HPVAg or LSE2E6E7SH show increased viral yields on cells capable of repressing transgene expression. A) Viral yield assay for Ad35 vectors. PER.C6, PER.C6/CymR, and PER.C6/TetR cells were infected by Ad35 vectors carrying GFP-Luc- or HPVAg-encoding transgenes. These transgenes were driven by either CuO- or TetO-containing CMV promoters. Viral yields were determined four days after infection by an Ad35 hexon-specific qPCR-based method. B) Viral yield assay for Ad26 vectors. PER.C6 and PER.C6/TetR cells were infected by Ad26 vectors carrying GFP-Luc, HPVAg, or LSE2E6E7SH-encoding transgenes, which were all driven by a TetO-containing CMV promoter. Viral yields were determined three days after infection by an Ad26 hexon-specific qPCR-based method. For details see Example 6.

The effect of TetR- and CymR-mediated repression of adenovector transgene expression on vector yields was investigated for Ad35-based vectors expressing HPVAg (FIG. 13A). To this end, PER.C6, PER.C6/TetR, and PER.C6/CymR cell lines, seeded at $3*10^5$ cells per well in 24-well plate wells, were subjected to quadruplicate infections—at 1000 virus particles per cell and for a duration of three hours—by vectors expressing HPVAg from either CMVTetO or CMVCuO promoters. As controls, parallel infections were performed with corresponding vectors expressing GFP-Luc instead of HPVAg. Four days after infection, crude viral lysates were prepared by subjecting the contents of the wells (i.e. infected cells and medium) to two freeze-thaw cycles. Adenovector titers were subsequently determined by an Ad35 hexon sequence-specific quantitative PCR-based protocol that uses a purified Ad35 vector with known virus particle titer as a standard. The results show that both the TetO- and the CuO-containing HPVAg-encoding Ad35 vectors, compared to the control vectors expressing GFP-Luc, display decreased vector yields on normal PER.C6 cells. By contrast, when produced on cells expressing their cognate repressors (i.e. TetR and CymR, respectively), these same vectors gave yields as high as those obtained with the control vectors. These data indicate that repression of transgene expression during vector production in producer cells can be beneficial for the productivity of Ad35 vectors carrying HPVAg as a transgene.

The effect that repression of adenovector transgene expression may have on vector yields was also investigated for vectors derived from adenovirus serotype 26 (Ad26) (FIG. 13B). In an assay performed essentially as described above for the Ad35 vectors, Ad26 vectors carrying CMVTetO promoter-controlled transgenes encoding either GFP-Luc, HPVAg, or LSE2E6E7SH were used to infect PER.C6 and PER.C6/TetR cells at 1500 virus particles per cell. Three days later the infections were harvested and virus particle titers determined by an Ad26 hexon sequence-specific quantitative PCR-based method. The results show that on PER.C6 cells the yields for the vectors encoding HPVAg and LSE2E6E7SH are lower than obtained with the control vector encoding GFP-Luc. In contrast, on PER.C6/TetR cells, both these vectors showed titers that are as high as that obtained for the control vector. Together with the results above (for Ad35 vectors), these data indicate that repression of transgene expression during adenovector production increases the yields of vectors expressing HPVAg and LSE2E6E7SH.

We have observed major issues regarding the genetic stability of an adenovirus vector that carried a CMV promoter-driven transgene for HPVAg. For example, it was observed that after several passaging rounds of this vector on PER.C6 the majority of the vector population consisted of a mutant vector that carried a large deletion in the HPVAg coding sequence (data not shown).

Figure 14:
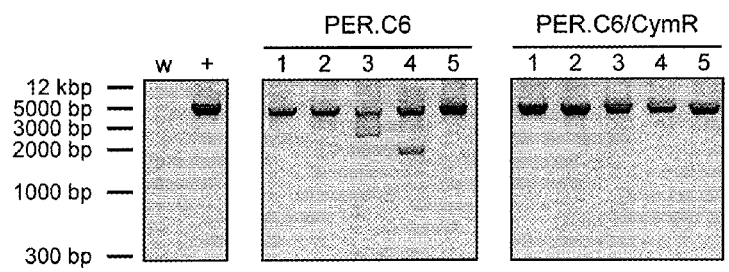
FIG. 14. Employment of a repressor system to repress transgene expression during vector production prevents transgene cassette instability in an adenoviral vector carrying an HPVAg-encoding transgene. An Ad35 vector expressing HPVAg under the control of CMVCuO was rescued by DNA transfection on either PER.C6 or PER.C6/CymR cell lines. Resultant viral plaques were picked—five per cell line—and used for consecutive infection rounds on the respective cell lines. A) Analysis of the integrity of the vector transgene cassette region by PCR after 10 viral passages. PCR products obtained from viral isolates passaged on PER.C6 and PER.C6/CymR are shown in the middle and right panels, respectively. The full-length-appearing PCR products obtained for PER.C6-passaged viral isolates 1, 2, 4, and 5, and those seen for PER.C6/CymR-passaged isolates 1 to 5 were analyzed by Sanger DNA sequencing. Analysis of the chromatogram traces (not shown) revealed that all isolates grown on PER.C6, but not those grown on PER.C6/CymR, contained either frameshifting small deletions or premature stop mutations within the coding sequence for HPVAg. B) Analysis of the ability of the vectors to express HPVAg after seven viral passages. A549 cells were transduced by the PER.C6- and PER.C6/CymR-grown viral isolates and HPVAg expression was analyzed by Western Blot using an HPV16 E7-specific antibody. The predicted size for HPVAg is 83 kDa. For details see Example 6.
Figure 14:
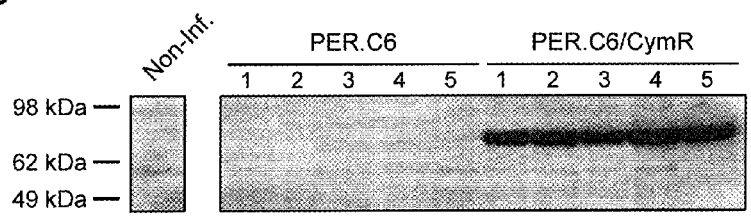

We reasoned that employment of a transgene expression repression system, such as one of the two described above, could prevent genetic stability issues associated with transgenes, such as HPVAg that are inhibitory to vector growth. To test this, an Ad35-based vector with CMVCuO promoter-driven HPVAg expression was assessed for transgene cassette stability upon growth of the vector on either PER.C6 or PER.C6/CymR cells (FIG. 14). In brief, vector DNA was transfected into the two different cell lines and resultant viral plaques were allowed to grow under an agarose layer. From each of the two transfections, five viral plaques were isolated and separately passaged further on the same cell line (i.e. as used for the transfection), for ten consecutive viral passages. Transgene integrity was assessed by PCR amplification of the transgene cassette at viral passage number ten (VPN10), and the subsequent analysis of resultant PCR products by gel electrophoresis and Sanger sequencing. In addition, at VPN7, the passaged viral clones were assessed for their ability to express HPVAg. This was done by using the passaged viral isolates to infect A549 cells at 1000 virus particles per cell, lysing the cells at 48 hours post infection, and subsequently analyzing the expression of HPVAg by western blotting using a monoclonal antibody directed against HPV16 E7 (Santa-Cruz Biotechnology). The results of the gel electrophoresis and sequencing analyses showed that all five viral isolates that had been passaged on PER.C6 each carried either small frameshifting deletions or premature stop mutations within the transgene cassette. By contrast, such deletions or mutations could not be detected in any of the vector isolates that had been passaged on the cell line expressing CymR (PER.C6/CymR). In agreement with these data, all PER.C6/CymR-propagated vector isolates were able to express HPVAg, while all PER.C6-grown vectors completely lost this ability, suggesting defective transgene cassettes for these vectors. In conclusion, our data demonstrate that employment of a repressor system, as for instance the CymR/CuO system, to repress vector transgene expression during vector propagation is an effective means to prevent severe transgene cassette instability, such as that seen for vectors carrying a transgene expressing HPVAg.

Example 7: Construction of a Designer Polypeptide Comprising Essentially all HPV18 E6 and E7 CTL Epitopes Similar to our design for HPV16 E6 and E7, we designed a novel, non-tumorigenic polypeptide (and nucleic acid encoding such) that contains essentially all CTL epitopes of HPV18 E6 and E7 proteins, and has a minimum number of anticipated/predicted strong neo-epitopes (neo-epitopes meaning epitopes not present in the wild type HPV18 E6 and E7 proteins). The polypeptide of the disclosure for HPV18 (also sometimes referred to as HPV18 'E6E7SH' herein) comprises the amino acid sequence as provided in SEQ ID NO: 20. A codon-optimized nucleic acid encoding this polypeptide is provided in SEQ ID NO: 21.

The molecules of the disclosure for HPV18 have the same advantages as described under example 1 for HPV16. They are single molecules, which provides manufacturing advantages over strategies where multiple molecules are used. In addition, the polypeptide of the disclosure comprises essentially all putative CTL epitopes that are present in wild-type E6 and E7 of HPV18, and at the same time have a minimum number of anticipated/predicted strong neo-epitopes that could potentially be immunodominant and thus divert the immune response from relevant wild-type CTL epitopes. Thus the constructs of the disclosure are immunologically more favourable than molecules described by others that either lack possible CTL epitopes and/or that contain more or stronger neo-epitopes.

For instance, the HPV18 designer construct of SEQ ID NO: 20 contains only five neo-epitopes with a length of nine amino acids with a predicted binding affinity <50 nM for the 20 most common HLA-A, 20 most common HLA-B and 20 most common HLA-C alleles, as described in example 1 for the HPV16 designer construct (having SEQ ID NO: 1).

Nucleic acid encoding our thus designed HPV18 E6E7SH molecule (i.e. a polypeptide having amino acid sequence as provided in SEQ ID NO:20) was synthesized, the nucleic acid sequence comprising SEQ ID NO: 21, and flanked by a HindIII site and a Kozak sequence on the 5'end and an XbaI site on the 3'site (custom synthesis and standard molecular cloning at Invitrogen Life technologies, Germany).

The synthesised fragments were cloned using HindIII and XbaI into a standard expression vector, pCDNA2004.Neo, harbouring both a bacterial resistance marker (Ampicillin) and a mammalian resistance marker (Neomycin), to obtain plasmid vectors encoding an HPV18 designer molecule of the invention, e.g. for (transient) transfection based experiments.

These molecules could be used as such, but also as the basis for further molecules that contain additional features. As non-limiting examples, some further variants were prepared as described below.

The HPV18 E6E7SH fusion protein sequence can be combined with sequences of other HPV18 early proteins to target individuals with persistent infection and to broaden the immune repertoire in an immunized individual. As a non-limiting example of such embodiments, we prepared a sequence coding for a fusion protein of E6E7SH with E2 at its N-terminus. We mutated Glycine at position 294, Lysine at position 300 and Cysteine at position 301 of the wt HPV18 E2 protein (Genbank: AAP20597.1) into respectively Valine, Methionine and Arginine to abrogate DNA binding activity. Each of these mutations on its own already completely abrogates the binding of E2 to DNA sequences that harbour E2 binding domains (Prakash et al., 1992, *Genes Dev* 6: 105-16).

The resulting polypeptide is referred to as HPV18 E2E6E7SH and comprises SEQ ID NO: 22. A codon-optimized sequence encoding this polypeptide was prepared and is provided in SEQ ID NO: 23.

The sequences that encode the HPV18 E6E7SH polypeptides of the invention, with or without E2, can for instance be expressed from DNA constructs, from RNA or from viral vectors. FIG. 15 demonstrates expression in HEK-293T cells upon transient transfection with DNA vectors expressing transgenes as described above. After transfection, cells were harvested and cell extracts were analyzed by SDS-PAGE and western blotting with an antibody that recognizes E6 of HPV18. This experiment demonstrates expression of the expected fusion proteins of appropriate size upon transfection of the expression vectors.

Adenoviral vectors can be used to express the E6E7, either with or without E2, and with or without additional sequences to augment the immunogenicity of the encoded fusion protein.

The genes, coding for HPV18 designer sequences described above were gene optimized for human expression and synthesized, at Geneart. A Kozak sequence (5' GCCACC 3') was included directly in front of the ATG start codon, and two stop codons (5' TGA TAA 3') were added at the end of the respective coding sequence. The genes were inserted in the pAdApt35BSU plasmid and in the pAdApt26 plasmid (Havenga et al., 2006, *J Gen Virol* 87, 2135-43) via HindIII and XbaI sites.

Ad35.HPV18-E6E7SH is a recombinant adenovirus serotype 35 (Ad35) vector comprising the codon-optimized nucleotide sequences for the expression of the HPV18 designer fusion protein variant as described above (HPV18 E6E7SH, having the amino acid sequence provided in SEQ ID NO: 20). The combined E6 and E7 sequences were placed under the control of a CMV promoter in the E1 region of the E1, E3 deleted adenovirus genome. Ad26.HPV18-E6E7SH is the equivalent vector based on recombinant adenovirus serotype 26.

Similarly, Ad26 and Ad35-based recombinant adenoviral vectors were produced that encode the HPV18 E2E6E7SH (SEQ ID NO: 22) variant.

All adenoviruses were generated, prepared, purified and stored as described in example 1 above.

Example 8. Lack of Transforming Activity of the HPV18 Designer Constructs

The E6 and E7 proteins of HPV18 have tumorigenic potential, which is apparent as transforming activity in certain assays, such as colony formation in a soft-agar assay (Massimi and Banks, 2005, *Methods Mol Med* 119: 381-395). The E6E7SH polypeptide as described in example 7 comprises the fragments of the E6 and E7 proteins in a re-ordered fashion. This is expected to remove the tumorigenic potential, as can be measured for instance by lack of transforming activity as compared to either of wt E6 and E7 proteins in such assays.

Others reported that gene-shuffled variants of HPV16 E6 and E7 have indeed lost their oncogenic potential (Öhlschläger et al., 2006, *Vaccine* 24: 2880-93; Henken et al., 2012, *Vaccine* 30: 4259-66), demonstrating that gene shuffling destroys the wild-type functions of HPV16 E6 and E7 proteins. In example 2, we have shown that our designer construct for HPV16 has lost its E6 and E7 activities.

To assess the loss of tumorigenic properties, we assessed the ability of our HPV18 E6E7SH construct to confer the ability to grow in soft agar upon NIH 3T3 cells (as described by e.g. Massimi and Banks, 2005, *Methods Mol Med* 119: 381-395). Transfection of NIH3T3 cells with a plasmid expressing the wild type HPV18 E7 resulted consistently in colony formation. Similar to the results obtained with HPV16 E6, expression of wild type HPV18 E6 alone did not cause colony formation above background. Transfection with our HPV18 E6E7SH construct did not lead to growth of colonies of cells in soft agar (FIG. 16) in four independent experiments, demonstrating that nucleic acids encoding a polypeptide of the disclosure, HPV18 E6E7SH, have lost the transforming capacity that is associated with E7.

The tumorigenic potential of E6 and E7 is associated with their ability to reduce the levels of the cellular proteins p53 and pRb respectively. p53 and pRb degradation assays were performed to demonstrate that nucleic acid encoding a polypeptide of the disclosure, HPV18 E6E7SH, does not have the biological activity associated with the wild-type E6 and E7 at the molecular level. In short, HPV18 E6 wt and our HPV18 E6E7SH construct were expressed in NCI-H1299 cells that lack endogenous p53 for the p53 degradation assay. For the pRb degradation assay HPV18 E7 wt and the HPV18 E6E7SH construct were expressed in pRb null Saos-2 cells. As can be seen in FIG. 17, co-expression of p53 with HPV18 E6 wt, but not with HPV18 E6E7SH, leads to reduced p53 levels (panels A and B). Likewise, panels 17C,D show that co-expression of pRb with HPV18 E7 wt, but not with HPV18 E6E7SH, leads to reduced pRB levels. These data demonstrate that nucleic acid encoding an HPV18 designer polypeptide of the disclosure has no ability to form colonies in soft agar and does not contain main biological activities of the wild-type HPV18 E6 and E7 polypeptides, namely the inactivation of p53 and pRb respectively.

To further demonstrate the safety of nucleic acid constructs encoding polypeptide of the disclosure, we made use of primary human genital keratinocytes derived from neonatal foreskin (HEKn cells) that closely resemble the natural target cells for HPV mediated transformation. Immortalization of primary human keratinocytes requires the action of both E6 and E7 wild-type (Munger et al., 1989, *J Virol* 63: 4417-21). This assay is probably the physiologically most relevant in vitro assay to demonstrate the safety of our constructs (Massimi and Banks, 2005, *Methods Mol Med* 119: 381-395). Cells transduced with lentiviruses expressing wild type E6 and E7 from HPV18 (E6E7 wt) induce immortalization in primary keratinocytes as indicated by the extension of their lifespan as compared to non-transduced control cells (FIG. 18) and activation of hTERT, the catalytic subunit of telomerase (data not shown). Expression of the HPV18 designer polypeptide of the disclosure (HPV18 E6E7SH) is not able to extend the lifespan compared to GFP-transduced or non-transduced keratinocytes. A similar result was obtained in two additional independent donors (data not shown). Taken together these data demonstrate that our constructs have lost the ability to induce immortalization in primary human keratinocytes, that are considered a highly physiological model.

All together the experiments in this example provide strong evidence of the lack of transforming activity of nucleic acids encoding polypeptides of the disclosure, and thus a strongly improved safety over HPV18 E6 and E7 wt constructs.

Comparative Example 8A. The Constructs of the Invention have Unique Properties

A further HPV18 designer construct had been prepared (referred to herein as 'HPV18DC2'; the amino acid sequence of this construct is provided as SEQ ID NO: 24). HPV18DC2 has the following features in common with the HPV18 E6E7SH (SEQ ID NO: 20) construct of the invention: (a) it also contains virtually the complete E6 and E7 amino acid sequences of HPV18, (b) in the form of the same number of re-ordered fragments, (c) which fragments are partly overlapping such that essentially all T-cell epitopes of HPV18 E6 and E7 are present, and (d) it was designed to minimize the introduction of undesired strong neo-epitopes. The designer construct of the invention and HPV18DC2 therefore structurally only differ in the exact amino acid sequence.

However, this does translate into at least one biologic difference, which demonstrates that such molecules cannot be considered mere alternatives that could be substituted for each other.

In particular, the molecule of the invention was entirely devoid of measurable functional activity in extending lifespan of primary foreskin keratinocytes, as shown above (example 8). In contrast, HPV18DC2 did induce an extended life span in primary keratinocytes. For example, according to the experiment described in example 8, cells of a donor expressing the HPV18 E6E7SH construct of the invention had a life span of 81 days in which they had 7 passage doublings, whereas in comparison cells with HPV18DC2 had a longer life span of 120 days in which they had 67 passage doublings. Similar differences were found in independent assays in keratinocytes from different donors (in an average from 3 donors, cells with the construct of the invention had a lifespan of 62 days with 9 passage doublings, whereas cells with HPV18DC2 had a much longer lifespan of 156 days with 62 passage doublings), showing the differences resulted from the difference between the constructs. In line with this observation that life span was extended by HPV18DC2, cells transduced with HPV18DC2 displayed some residual E7 activity (i.e. pRb degradation/ p16 upregulation), in contrast to cells transduced with the HPV18 E6E7SH molecule of the invention that lacked detectable activity in these assays (example 8).

Similar observations were made with an alternative HPV16 designer construct when compared to the HPV16 designer construct of the invention (as referred to in example 2).

The observed differences between seemingly highly similar molecules in a biologic model system demonstrate that such molecules cannot be considered mere alternatives that could be substituted for each other. This underscores the uniqueness of the designer molecules of the disclosure, and the unpredictability in this field.

Importantly, it can be concluded from the experiments in examples 2 and 8 that the designer molecules of the disclosure have lost the oncogenic activities of wild-type HPV16/ 18 E6 and E7 proteins in the used model systems.

Example 9. Immune Responses to the HPV18 E6E7SH Designer Constructs

We have prepared DNA vectors and adenoviral vectors, as described in example 7. To evaluate the vaccine induced immunogenicity, CB6F1 mice were immunized with adenovectors (Ad35) expressing HPV18 E6E7SH or E2E6E7SH, or with adenovectors not encoding a transgene (Empty) as controls. Two weeks after the prime immunization the mice were sacrificed and isolated splenocytes were stimulated overnight with an HPV18 E6 15mer peptide pool. E6-specific immune responses were analyzed by intracellular cytokine staining. In a separate experiment, CB6F1 mice were immunized with adenovectors (Ad35 or Ad26) expressing HPV18 E2E6E7SH or with adenovectors not encoding a transgene (Empty) as control.

Figure 15:
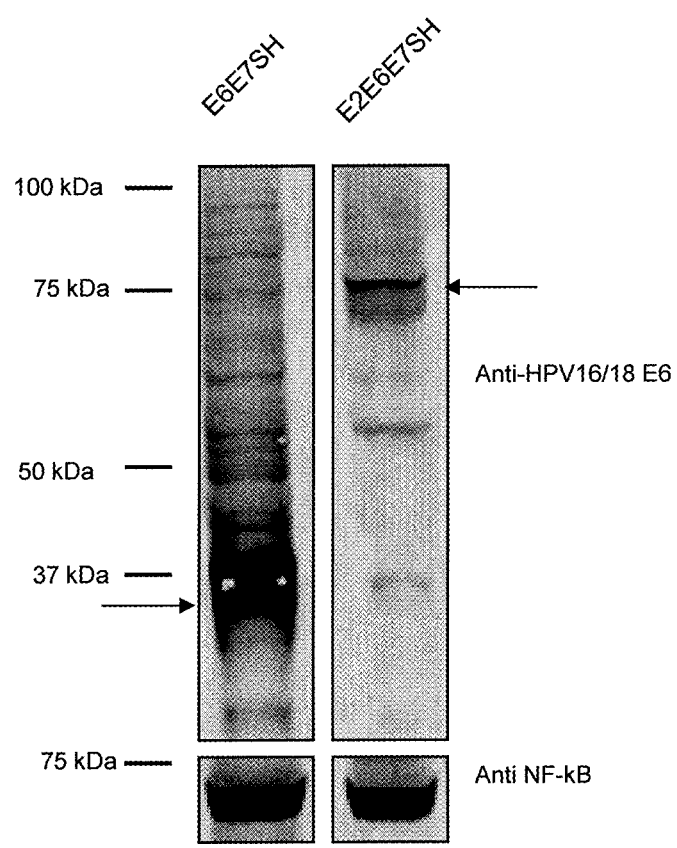
FIG. 15. Expression of fusion proteins of HPV18 E6 and E7. HEK-293T cells were transiently transfected with DNA vectors expressing the transgenes indicated above the figure. 24 hr after transfection the cells were harvested and cell extracts were analyzed by SDS-PAGE and western blotting with an antibody against HPV18 E6 (upper panel). A loading control showing NF-kB (lower panel) confirms similar loading of cell lysates in both lanes. A molecular weight marker is indicated on the left and arrows indicate the fusion proteins. Expected sizes: E6E7SH approx. 38 kDa; E2E6E7SH approx. 75 kDa.
Figure 16:
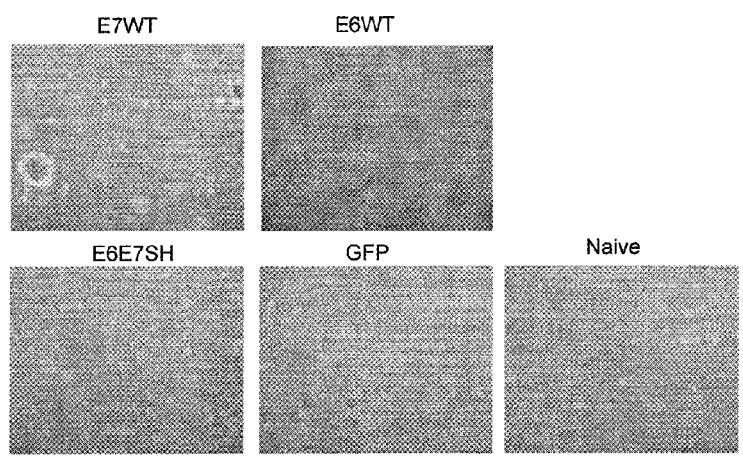
FIG. 16. No colony formation in soft agar by the HPV18 E6E7SH designer construct. A) Representative microscopic images at 40× magnification of the cells in agar six weeks post seeding. Large colonies are observed in the E7 wt transfected cells. B) Colony quantification six weeks post seeding in agar using the Gelcount™ and associated software. *: $p<0.05$ (Poisson regression model); **: non-inferior (generalized linear model with non-inferiority margin of 5%).
Figure 16:
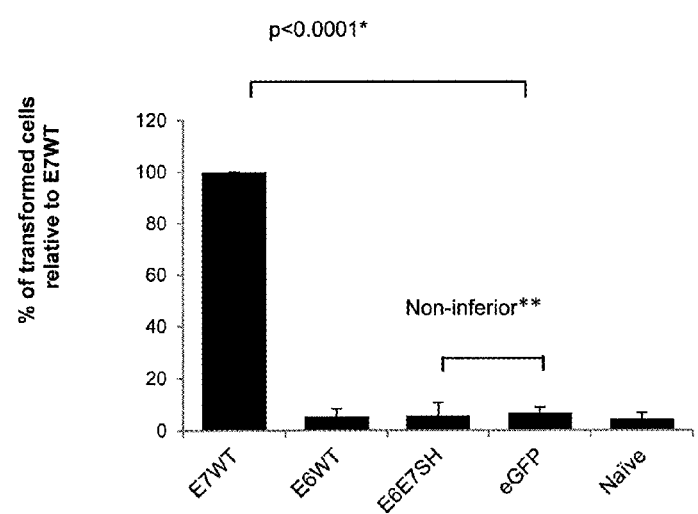
Figure 17:
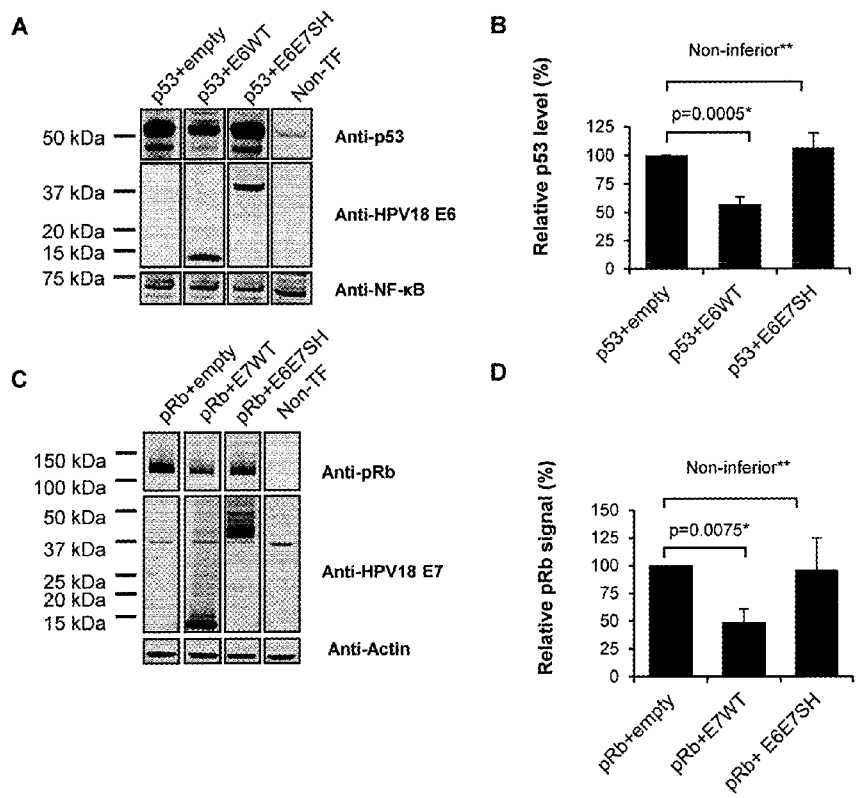
FIG. 17. HPV18 E6E7SH has lost the ability to degrade p53 and pRb. A) Representative western blot demonstrating absence of p53 degradation by HPV18 E6E7SH. Human p53 null NCI-H1299 cells were co-transfected with a plasmid expressing p53 in combination with a plasmid expressing HPV18 E6 wild-type, E6E7SH or the empty vector. Non-TF indicates non-transfected cells. 24 hours after transfection cell lysates were prepared and 30 μg of total protein was loaded on gel. Upper panel—p53 staining, middle panel—E6 staining, lower panel—NF-kB staining (loading control). (B) Quantification of p53 levels in four independent assays. The p53 signal was normalized to the NF-κB signal. C) Western blot demonstrating lack of pRb degradation by HPV18 E6E7SH. pRb null Saos-2 cells were transfected with a plasmid expressing pRb in combination with a plasmid expressing HPV18 E7 wild-type, E6E7SH or the empty vector. Non-TF indicates non-transfected cells. 24 hours after transfection cell lysates were prepared and 10 μg of total protein was loaded on gel. Upper panel—pRb staining, middle panel—E7 staining, lower panel—NF-κB staining (loading control). D) Quantification of pRb levels in four independent assays. The pRb signal was normalized to the NF-κB signal. *: $p<0.05$ (ANOVA models); **: non-inferior (testing was based on 95% CI's derived from ANOVA models. Non-inferiority margin was set at 75%).
Figure 18:
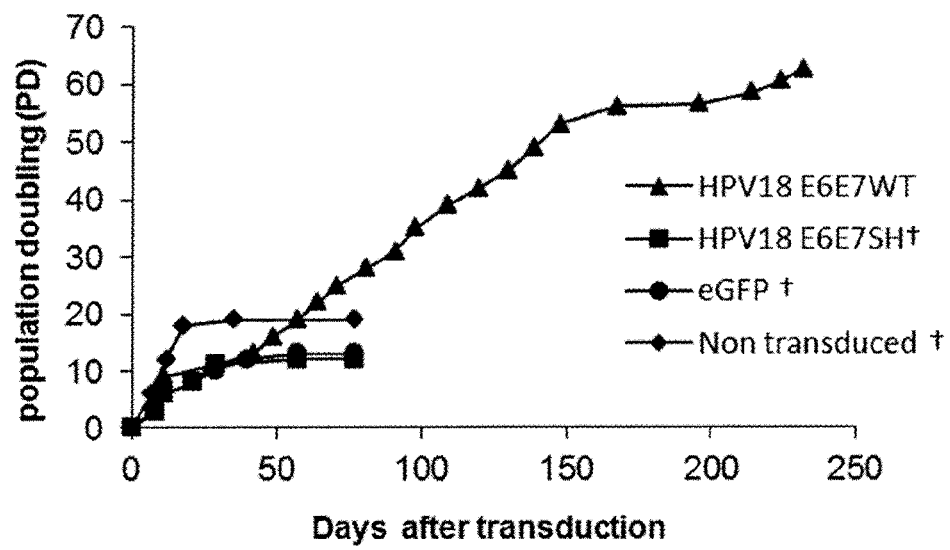
FIG. 18. HPV18 E6E7SH does not immortalize primary human genital keratinocytes. Primary human genital keratinocytes were transduced with lentiviruses encoding either the wild-type E6- and E7-encoding open reading frame of HPV18 (E6E7 wt), the E6E7SH sequence or eGFP. Non-transduced donor cells were used as a control. Only expression of HPV18 E6E7 wt induces immortalization of primary keratinocytes as indicated by the extended lifespan (and hTERT activation around day 200, data not shown). The cross symbol indicates that the cells died in senescence and could not be further cultured. For details see example 8. Similar results were obtained in two additional donors (data not shown).
Figure 19:
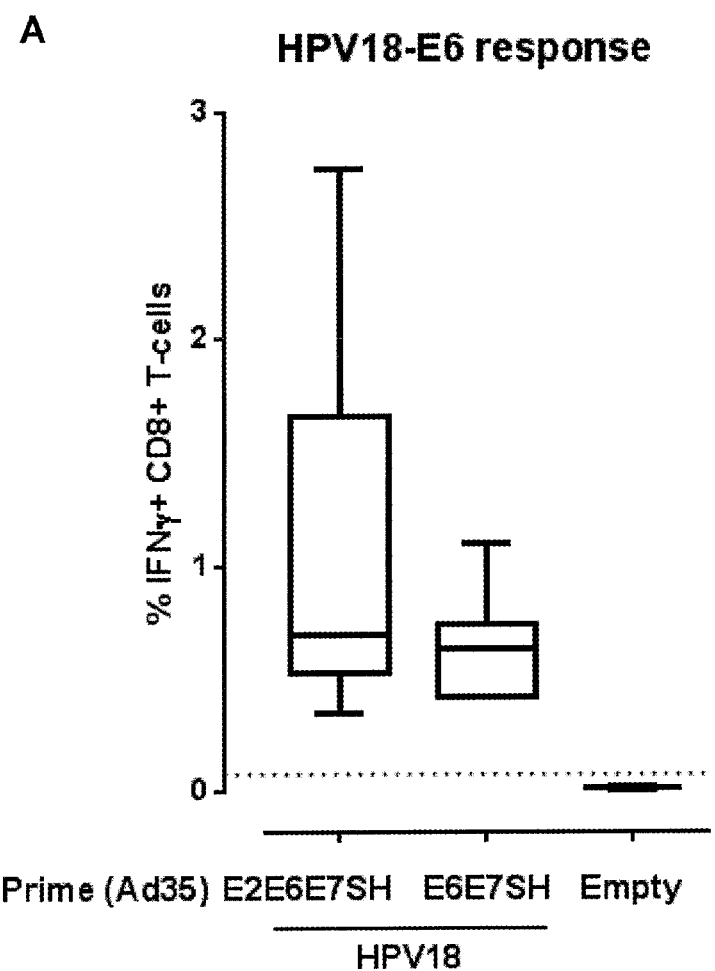
FIG. 19. Immunogenicity of HPV18 E6E7SH variants—Intracellular Cytokine staining. CB6F1 mice were immunized with adenovectors expressing the transgenes indicated below the panels. Two weeks after immunization the mice were sacrificed and isolated splenocytes were stimulated overnight with 15mer peptide pools corresponding to HPV18 E6. Responses are given as percentage of IFNγ-positive CD8+ T-cells.

FIG. 19A shows that immunization of mice with Ad35.HPV18-E6E7SH induces E6-specific immune responses as measured by ICS analysis. In addition, the results in FIG. 19A demonstrate that fusion of E2 to the N-terminus of the designer construct does not decrease the immunogenicity, despite the lower expression of this E2E6E7 variant that was observed upon transfection (FIG. 15). FIG. 19B shows that immunization of mice with Ad35.HPV18-E6E7SH or Ad26.HPV18-E2E6E7SH induces comparable percentage of IFNγ-producing HPV18-E6 specific CD8 T-cells.

The cellular immune response against the peptide of the invention can be induced with different types of adenoviral vectors. In the experiment presented in FIG. 19B, mice were immunized with either Ad26 or Ad35 adenoviral vectors expressing HPV18 E2E6E7SH. The data show that these adenoviral vectors induced HPV18 E6-specific T-cells to similar levels.

Figure 20:
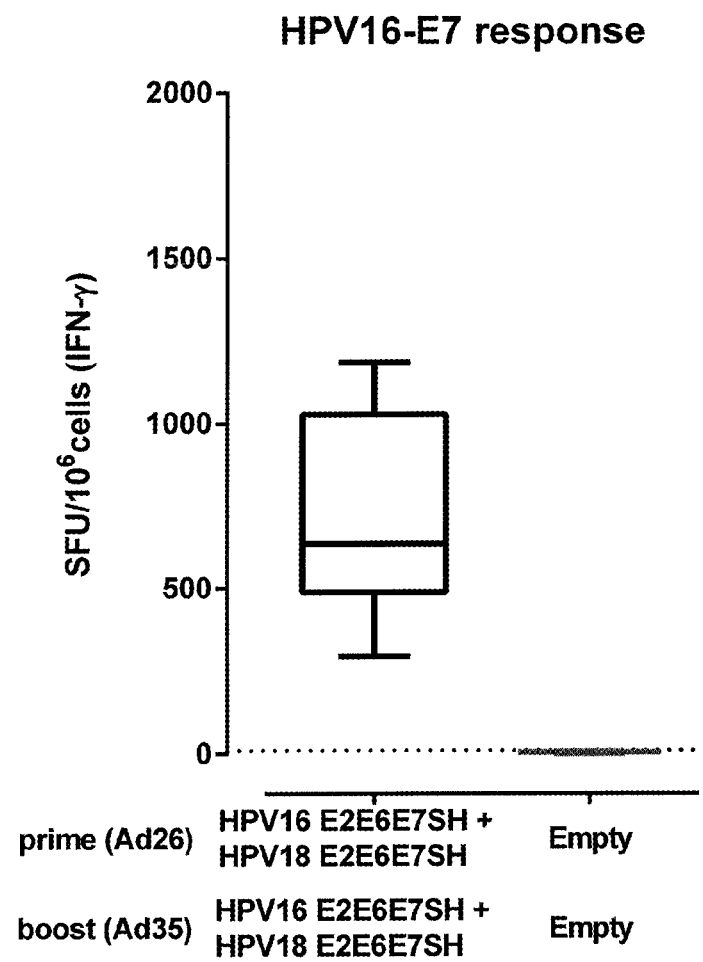
FIG. 20. Immunogenicity of combined HPV16 and HPV18 vectors—IFNγ ELISPOT analysis. CB6F1 mice were immunized with adenovectors (type 26) expressing the E2E6E7SH transgenes from both HPV16 (encoding SEQ ID NO: 3) and HPV18 (encoding SEQ ID NO: 22). Four weeks after prime immunization the mice received an heterologous boost immunization with adenoviral vectors of type 35 with the same E2E6E7SH transgenes. Two weeks after the boost immunization the mice were sacrificed and isolated splenocytes were stimulated overnight with 15mer peptide pools corresponding to HPV16 E7 (A) or HPV18 E6 (B). Responses are given as SFU per $10^6$ splenocytes.

Example 10. Combining Adenoviral Vectors Expressing HPV16 and HPV18 Designer Constructs Combining designer constructs for different HPV types offers the possibility to make a treatment vaccine for different HPV types. To evaluate the ability of the adenoviral vectors expressing different designer sequences to induce immune responses, mice were immunized by intramuscular injection with the adenovectors (Ad26) expressing HPV16 E2E6E7SH (encoding protein comprising amino acid sequence set forth in SEQ ID NO: 3) and with Ad26 expressing HPV18 E2E6E7SH (encoding protein comprising amino acid sequence set forth in SEQ ID NO: 22) with a dose of $1*10^{10}$ vp for each vector or adenovectors not encoding a transgene (Empty). Four weeks after the immunization the immune responses were boosted by immunization with Ad35 vectors expressing the same antigens. Immune responses were measured two weeks after the boost immunization. Cells were stimulated overnight with peptide pools corresponding to E6 of HPV18 or E7 of HPV16 and responses were measured by IFNγ ELISPOT. The data are presented in FIG. 20.

The data show that immunization of mice with Ad26/35 vectors expressing HPV16 E2E6E7SH and HPV18 E2E6E7SH resulted in cellular immune responses against both (i.e. HPV16 and HPV18) designer proteins.

In an independent experiment with a similar immunization schedule (Ad26 prime and Ad35 boost) we compared the immune response induced by Ad expressing HPV16 E2E6E7SH and Ad expressing HPV18 E2E6E7SH together to that induced in mice immunized with Ad expressing HPV16 E2E6E7SH alone or Ad expressing HPV18 E2E6E7SH alone. Immune responses were measured two weeks after boost immunization, and cells were stimulated overnight with peptide pools corresponding to E2, E6 or E7 of HPV16 and HPV18 and the responses were measured by IFNγ ELISPOT as well as intracellular cytokine staining. Although co-administration in a single composition of Ad expressing HPV16 E2E6E7SH and Ad expressing HPV18 E2E6E7SH did result in an overall lower magnitude of CD4 and CD8 responses as compared to animals that were only immunized with the individual vaccine components, the co-administration induced a similar breadth of the immune responses (data not shown).

Co-administration of HPV16 E2E6E7SH and HPV18 E2E6E7SH expressing constructs of the disclosure is thus possible to induce cellular immune responses to both HPV16 and HPV18.

Example 11. Immunogenicity of Combined Designer Constructs in Rhesus Macaques

Figure 21:
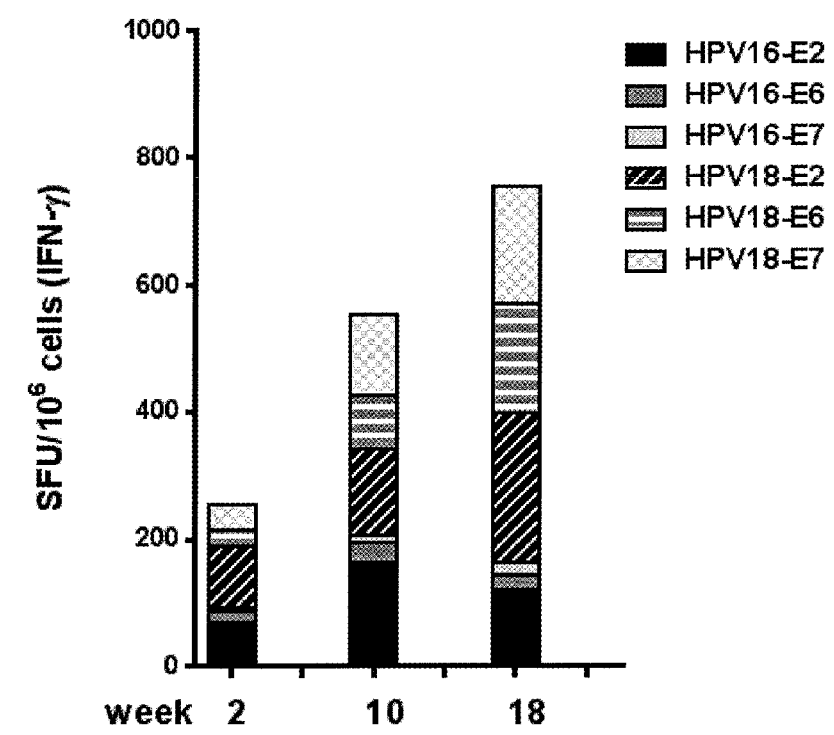
FIG. 21. Cellular immunogenicity of combined HPV16 and HPV18 vaccine in Rhesus macaques. Rhesus macaques were immunized according to the scheme as presented in FIG. 11, with a combination of HPV16 and HPV18 designer constructs. At day 0: Eight animals received a mixture of Ad26.HPV16-E2E6E7SH and Ad26.HPV18-E2E6E7SH by intramuscular immunization (i.m). A boost immunization with the same vectors was given at 8 weeks. At 16 weeks, animals received a second boost immunization with a mixture of two Ad35 vectors expressing the same HPV16 and HPV18 E2E6E7SH fusion proteins. The dose of adenovectors was $1*10^{11}$ vp per vector per immunization. Blood drawings were performed at several time points. Cellular immune responses in PBMCs were measured by IFNγ ELISPOT. PBMCs were stimulated with peptide pools corresponding to E2, E6 or E7 of HPV16 and HPV18 and the number of spot-forming units (SFU) in $1*10^6$ PBMCs were determined. The figure shows cumulative responses for all six tested peptide pools at 2 weeks after each immunization. For details see example 11.

To evaluate the ability of the adenoviral vectors expressing the designer sequences of the invention to induce immune responses in non-human primates, rhesus macaques were immunized by intramuscular injection with the mix of two separate adenovectors as in the previous example, i.e. Ad26 vectors together expressing HPV16 and HPV18 E2E6E7SH, at a dose of $1*10^{10}$ vp for each vector, or adenovectors not encoding a transgene (Empty). Eight weeks after the immunization, animals received a boost immunization with Ad26 vectors expressing the same antigens. At week 16 the animals received one more injection with the Ad35 vectors expressing the same antigens. Blood samples were taken at several time points and isolated white blood cells were stimulated overnight with peptide pools corresponding to E2, E6 or E7 for both HPV16 and HPV18. Specific responses were measured by IFNγ ELISPOT. The data are presented in FIG. 21. In addition at week 10 and week 18 post prime immunization, the cellular immune response specific to peptides spanning the novel junctions in the HPV18 designer molecules of the disclosure was evaluated. The induction of IFNγ response against these junctional peptides was in all animals below the limit of detection of <50 SFU per $1*10^6$ PBMC (data not shown).

The data show that immunization of non-human primates with a combination of Ad26 vectors together expressing HPV16 E2E6E7SH and HPV18 E2E6E7SH resulted in cellular immune responses against several of the HPV proteins that are present in the encoded transgenes. Responses could be boosted by the additional immunization with Ad26 vectors. The additional boost immunization at week 16 with the corresponding Ad35 vector further increased the immune responses.

Example 12. Therapeutic Efficacy of Combined Constructs in a Mouse Tumor Model

The polypeptide of the disclosure corresponding to HPV16 E6 and E7 is capable of inducing cellular immune responses in mice that will lead to a therapeutic effect in the TC-1 model (as shown in example 5). The therapeutic effect of a combination of adenoviral vectors together expressing both HPV16 and HPV18 designer proteins was tested in this same model. Without vaccine the tumors grew rapidly and reach a pre-determined size of 1000 mm³ within 30 days at which point the mice were sacrificed for ethical reasons.

Figure 22:
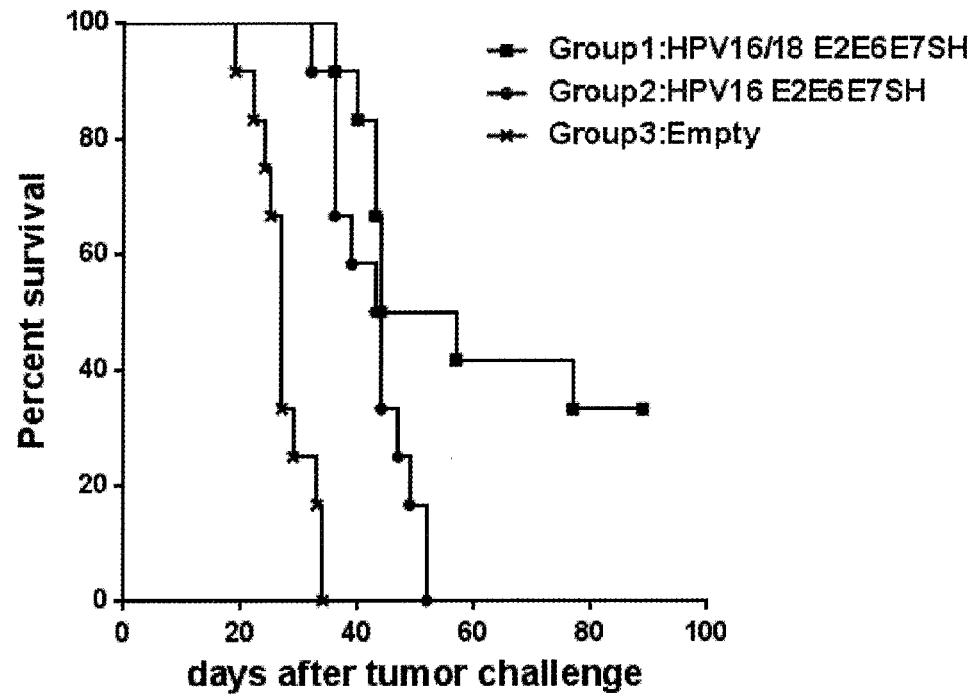
FIG. 22. Therapeutic effect of combined adenovectors expressing HPV16 and HPV18 E2E6E7SH. C57BL/6 mice were injected sub-cutaneously with $5*10^4$ TC-1 cells at day 0. After six days, when tumors were palpable, mice were immunized with Ad26.HPV16-E2E6E7SH or a mixture of Ad26.HPV16-E2E6E7SH and Ad26.HPV18-E2E6E7SH. Control mice received Ad26.Empty. All mice received a boost immunization at day 20 with the corresponding Ad35 vectors. Tumor volume was calculated as (width$^2$*length)/2. Mice were sacrificed when tumor volumes surpassed 1000 mm$^3$. The graphs show survival after TC-1 injection. Three mice immunized with the combined HPV16+HPV18 vaccine were tumor free at the end of the experiment. The median survival time of mice treated with Ad.HPV16-E2E6E7SH was not significantly different compared with mice immunized with Ad.HPV16/18-E2E6E7SH.

In this experiment, prime-boost immunizations with adenoviral vectors expressing HPV16 E2E6E7SH prolonged the survival of the mice significantly (FIG. 22). With a combination of adenoviral vectors together expressing both HPV16 E2E6E7SH and HPV18 E2E6E7SH, a similar mean survival time was observed. In the group of mice that received the combination vaccine, three animals were tumor free at the end of the monitoring period of 90 days. In conclusion, immunization with a combination of adenoviral vectors together expressing HPV16- and HPV18-specific designer polypeptides of the invention significantly reduced tumor growth or completely eradicated established tumors in a well-established challenge model for HPV16-induced cancer.

REFERENCES

Abbink P, Lemckert A A, Ewald B A, Lynch D M, Denholtz M, Smits S, Holterman L, Damen I, Vogels R, Thorner A R, O'Brien K L, Carville A, Mansfield K G, Goudsmit J, Havenga M J, Barouch D H (2007) Comparative seroprevalence and immunogenicity of six rare serotype recombinant adenovirus vaccine vectors from subgroups B and D. J Virol 81:4654-4663

Ausubel F M (1995) Short protocols in molecular biology: a compendium of methods from Current protocols in molecular biology. Wiley, [Chichester]

Brokaw J L, Blanco M, McBride A A (1996) Amino Acids Critical for the Functions of the Bovine Papillomavirus Type 1 E2 Transactivator. J Virol 70: 23-29

Cottingham M G, Carroll F, Morris S J, Turner A V, Vaughan A M, Kapulu M C, Colloca S, Siani L, Gilbert S C, Hill A V (2012) Preventing spontaneous genetic rearrangements in the transgene cassettes of adenovirus vectors. Biotechnol Bioeng 109:719-728

Daayana S, Elkord E, Winters U, Pawlita M, Roden R, Stern P L, Kitchener H C (2010) Phase II trial of imiquimod and HPV therapeutic vaccination in patients with vulval intraepithelial neoplasia. Br J Cancer 102:1129-1136 de Jong A, van der Burg S H, Kwappenberg K M, van der Hulst J M, Franken K L, Geluk A, van Meijgaarden K E, Drijfhout J W, Kenter G, Vermeij P, Melief C J, Offringa R (2002) Frequent detection of human papillomavirus 16 E2-specific T-helper immunity in healthy subjects. Cancer Res 62:472-479

Edholm D, Molin M, Bajak E, Akusjarvi G (2001) Adenovirus vector designed for expression of toxic proteins. J Virol 75:9579-9584

Evans R K, Nawrocki D K, Isopi L A, Williams D M, Casimiro D R, Chin S, Chen M, Zhu D M, Shiver J W, Volkin D B (2004) Development of stable liquid formulations for adenovirus-based vaccines. J Pharm Sci 93:2458-2475

Fallaux F J, Bout A, van der Velde I, van den Wollenberg D J, Hehir K M, Keegan J, Auger C, Cramer S J, van Ormondt H, van der Eb A J, Valerio D, Hoeben R C (1998) New helper cells and matched early region 1-deleted adenovirus vectors prevent generation of replication-competent adenoviruses. Hum Gene Ther 9:1909-1917

Frøkjær S, Hovgaard L (2000) Pharmaceutical formulation development of peptides and proteins. Taylor & Francis, London Gall J G, Lizonova A, EttyReddy D, McVey D, Zuber M, Kovesdi I, Aughtman B, King C R, Brough D E (2007)

Rescue and production of vaccine and therapeutic adenovirus vectors expressing inhibitory transgenes. Mol Biotechnol 35:263-273

Gao G P, Engdahl R K, Wilson J M (2000) A cell line for high-yield production of E1-deleted adenovirus vectors without the emergence of replication-competent virus. Hum Gene Ther 11:213-219

Gennaro A R (1990) Remington's pharmaceutical sciences. Mack

Gilbert R, Guilbault C, Gagnon D, Bernier A, Bourget L, Elahi S M, Kamen A, Massie B (2014) Establishment and validation of new complementing cells for production of E1-deleted adenovirus vectors in serum-free suspension culture. J Virol Methods 208:177-188

Hamid O, Carvajal R D (2013) Anti-programmed death-1 and anti-programmed death-ligand 1 antibodies in cancer therapy. Expert Opin Biol Ther 13:847-861

Harlow E, Lane D (1988) Antibodies: a laboratory manual. Cold Spring Harbor Laboratory, New York Havenga M, Vogels R, Zuijdgeest D, Radosevic K, Mueller S, Sieuwerts M, Weichold F, Damen I, Kaspers J, Lemckert A, van Meerendonk M, van der Vlugt R, Holterman L, Hone D, Skeiky Y, Mintardjo R, Gillissen G, Barouch D, Sadoff J, Goudsmit J (2006) Novel replication-incompetent adenoviral B-group vectors: high vector stability and yield in PER.C6 cells. J Gen Virol 87:2135-2143

Henken F E, Oosterhuis K, Ohlschlager P, Bosch L, Hooijberg E, Haanen J B, Steenbergen R D (2012) Preclinical safety evaluation of DNA vaccines encoding modified HPV16 E6 and E7. Vaccine 30:4259-4266

Hildesheim A, Herrero R, Wacholder S, Rodriguez A C, Solomon D, Bratti M C, Schiller J T, Gonzalez P, Dubin G, Porras C, Jimenez S E, Lowy D R (2007) Effect of human papillomavirus 16/18 L1 viruslike particle vaccine among young women with preexisting infection: a randomized trial. JAMA 298:743-753

Hoganson D K, Ma J C, Asato L, Ong M, Printz M A, Huyghe B G, Sosnowshi B A, D'Andrea M J (2002) Development of a stable adenoviral vector formulation. Bioprocess J 1:43-48

Hoof I, Peters B, Sidney J, Pedersen L E, Sette A, Lund O, Buus S, Nielsen M (2009) NetMHCpan, a method for MHC class I binding prediction beyond humans. Immunogenetics 61:1-13

Horwitz M S (1996) Adenoviruses. In: Fields B N, Knipe D M, Baines J D (eds) Virology. Raven Press Ltd, New York Kenter G G, Welters M J, Valentijn A R, Lowik M J, Berends-van der Meer D M, Vloon A P, Essahsah F, Fathers L M, Offringa R, Drijfhout J W, Wafelman A R, Oostendorp J, Fleuren G J, van der Burg S H, Melief C J (2009) Vaccination against HPV-16 oncoproteins for vulvar intraepithelial neoplasia. N Engl J Med 361:1838-1847

Kibbe A H (2000) Handbook of pharmaceutical excipients. Pharmaceutical Press, London Kim T J, Jin H T, Hur S Y, Yang H G, Seo Y B, Hong S R, Lee C W, Kim S, Woo J W, Park K S, Hwang Y Y, Park J, Lee I H, Lim K T, Lee K H, Jeong M S, Surh C D, Suh Y S, Park J S, Sung Y C (2014) Clearance of persistent HPV infection and cervical lesion by therapeutic DNA vaccine in CIN3 patients. Nat Commun 5:5317 (doi: 10.1038/ncomms6317)

Kovesdi I, Hedley S J (2010) Adenoviral producer cells. Viruses 2:1681-1703

Lin K Y, Guarnieri F G, Staveley-O'Carroll K F, Levitsky H I, August J T, Pardoll D M, Wu T C (1996) Treatment of established tumors with a novel vaccine that enhances major histocompatibility class II presentation of tumor antigen. Cancer Res 56:21-26

Lundegaard C, Lamberth K, Harndahl M, Buus S, Lund O, Nielsen M (2008) NetMHC-3.0: accurate web accessible predictions of human, mouse and monkey MHC class I affinities for peptides of length 8-11. Nucleic Acids Res 36:W509-512

Massimi P, Banks L (2005) Transformation Assays for HPV Oncoproteins. In: Davy C, Doorbar J (eds) Human Papillomaviruses: Methods and Protocols. Vol 119: Methods in Molecular Medicine Springer, Berlin, pp 381-395

Matthews D A, Cummings D, Evelegh C, Graham F L, Prevec L (1999) Development and use of a 293 cell line expressing lac repressor for the rescue of recombinant adenoviruses expressing high levels of rabies virus glycoprotein. J Gen Virol 80 (Pt 2):345-353

McPherson M J, Hames B D, Taylor G R (1995) PCR 2: a practical approach. IRL Press at Oxford University Press, OxfordMellman I, Coukos G, Dranoff G (2011) Cancer immunotherapy comes of age. Nature 480:480-489

Mishra S, Lavelle B J, Desrosiers J, Ardito M T, Terry F, Martin W D, De Groot A S, Gregory S H (2014) Dendritic cell-mediated, DNA-based vaccination against Hepatitis C induces the multi-epitope-specific response of humanized, HLA transgenic mice. Plos One 9 (8): e104606. DOT: 10.1371/journal.pone.0104606

Moise L, Buller R M, Schriewer J, Lee J, Frey S E, Weiner D B, Martin W, De Groot A S (2011) VennVax, a DNA-prime, peptide-boost multi-T-cell epitope poxvirus vaccine, induces protective immunity against vaccinia infection by T cell response alone. Vaccine 29: 501-511

Moss S F, Moise L, Lee D S, Kim W, Zhang S, Lee J, Rogers A B, Martin W, De Groot A S (2011). HelicoVax: epitope-based therapeutic *Helicobacter pylori* vaccination in a mouse model. Vaccine 29: 2085-2091

Mullick A, Xu Y, Warren R, Koutroumanis M, Guilbault C, Broussau S, Malenfant F, Bourget L, Lamoureux L, Lo R, Caron A W, Pilotte A, Massie B (2006) The cumate gene-switch: a system for regulated expression in mammalian cells. BMC Biotechnol 6:43

Munger K, Phelps W C, Bubb V, Howley P M, Schlegel R (1989) The E6 and E7 genes of the human papillomavirus type 16 together are necessary and sufficient for transformation of primary human keratinocytes. J Virol 63:4417-4421

Ogun S A, Dumon-Seignovert L, Marchand J B, Holder A A, Hill F (2008) The oligomerization domain of C4-binding protein (C4 bp) acts as an adjuvant, and the fusion protein comprised of the 19-kilodalton merozoite surface protein 1 fused with the murine C4 bp domain protects mice against malaria. Infect Immun 76:3817-3823

Oosterhuis K, Aleyd E, Vrijland K, Schumacher T N, Haanen J B (2012a) Rational Design of DNA Vaccines for the Induction of Human Papillomavirus Type 16 E6- and E7-Specific Cytotoxic T-Cell Responses. Hum Gene Ther 23:1301-1312

Oosterhuis K, Ohlschlager P, van den Berg J H, Toebes M, Gomez R, Schumacher T N, Haanen J B (2011) Preclinical development of highly effective and safe DNA vaccines directed against HPV 16 E6 and E7. Int J Cancer 129:397-406

Oosterhuis K, van den Berg J H, Schumacher T N, Haanen J B (2012b) DNA vaccines and intradermal vaccination by DNA tattooing. Curr Top Microbiol Immunol 351:221-250 Peters B, Tong W, Sidney J, Sette A, Weng Z (2003) Examining the independent binding assumption for binding of peptide epitopes to MHC-I molecules. Bioinformatics 19:1765-1772

Prakash S S, Grossman S R, Pepinsky R B, Laimins L A, Androphy E J (1992) Amino acids necessary for DNA contact and dimerization imply novel motifs in the papillomavirus E2 trans-activator. Genes Dev 6:105-116

Rubinchik S, Ding R, Qiu A J, Zhang F, Dong J (2000) Adenoviral vector which delivers FasL-GFP fusion protein regulated by the tet-inducible expression system. Gene Ther 7:875-885 Sambrook JFEFMT (1989) Molecular cloning: a laboratory manual Cold Spring Harbor Laboratory, Cold Spring Harbor, N.Y.

Sakai H, Yasugi T, Benson J D, Dowhanick J J, Howley P M (1996) Targeted Mutagenesis of the Human Papillomavirus Type 16 E2 Transactivation Domain Reveals Separable Transcriptional Activation and DNA Replication Functions. J Virol 70: 1602-1611

Sedman S A, Barbosa M S, Vass W C, Hubbert N L, Haas J A, Lowy D R, Schiller J T (1991) The full-length E6 protein of human papillomavirus type 16 has transforming and trans-activating activities and cooperates with E7 to immortalize keratinocytes in culture. J Virol 65:4860-4866

Shenk T (1996) Adenoviridae and their Replication. In: Fields B N, Knipe D M, Baines J D (eds) Virology. Raven Press Ltd, New York Smahel M, Sima P, Ludvikova V, Vonka V (2001) Modified HPV16 E7 Genes as DNA Vaccine against E7-Containing Oncogenic Cells. Virology 281:231-238 van der Burg S H, Melief C J (2011) Therapeutic vaccination against human papilloma virus induced malignancies. Curr Opin Immunol 23:252-257

Watson J D (1992) Recombinant DNA. Scientific American Books, New York

Wicking B G, Vermeer D W, Spanos W C, Lee K M, Vermeer P, Lee W T, Xu Y, Gabitzsch E S, Balcaitis S, Balint J P, Jr., Jones F R, Lee J H (2012) A non-oncogenic HPV 16 E6/E7 vaccine enhances treatment of HPV expressing tumors. Cancer Gene Ther 19:667-674

Yan J, Reichenbach D K, Corbitt N, Hokey D A, Ramanathan M P, McKinney K A, Weiner D B, Sewell D (2009) Induction of antitumor immunity in vivo following delivery of a novel HPV-16 DNA vaccine encoding an E6/E7 fusion antigen. Vaccine 27:431-440

Yao F, Eriksson E (1999) A novel tetracycline-inducible viral replication switch. Hum Gene Ther 10:419-427

Yoshida Y, Hamada H (1997) Adenovirus-mediated inducible gene expression through tetracycline-controllable transactivator with nuclear localization signal. Biochem Biophys Res Commun 230:426-430

Yugawa T, Kiyono T (2009) Molecular mechanisms of cervical carcinogenesis by high-risk human papillomaviruses: novel functions of E6 and E7 oncoproteins. Rev Med Virol 19:97-113

Zwaveling S, Ferreira Mota S C, Nouta J, Johnson M, Lipford G B, Offringa R, van der Burg S H, Melief C J (2002) Established human papillomavirus type 16-expressing tumors are effectively eradicated following vaccination with long peptides. J Immunol 169:350-358

TABLE I sequences

```
SEQ ID NO: 1 (HPV16-E6E7SH, amino acid sequence of HPV16 E6/E7 designer
polypeptide)
MHQKRTAMFQ DPQERPRKLP QLCTELQTTI HDIILECVYC KQQLEDEIDG PAGQAEPDRA
HYNIVTFCCK CDSTLRLCVQ STHVDIRTLE DLLMGTLGIV CPICSQKPGT TLEQQYNKPL
CDLLIRCINC QKPLCPEEKQ RHLDKKQRFH NIRGRWTGRC MSCCRSSRTR RETQMHGDTP
TLHEYMLDLQ PETTDLYCYE QLNDSSEEED EIDGPAGQAE PDRAHYNIVT FCCQLCTELQ
TTIHDIILEC VYCKQQLLRR EVYDFAFRDL CIVYRDGNPY AVCDKCLKFY SKISEYRHYC
YSLYGTTLEQ QYNKPLCDLL IRCINCQK SEQ ID NO: 2 (HPV16-E6E7SH, nucleotide sequence encoding amino acid
sequence of HPV16 E6/E7 designer polypeptide)
ATGCACCAGA AACGGACCGC CATGTTCCAG GACCCCCAGG AACGGCCCAG AAAGCTGCCC
CAGCTGTGCA CCGAGCTGCA GACCACCATC CACGACATCA TCCTGGAATG CGTGTACTGC
AAGCAGCAGC TGGAAGATGA GATCGACGGC CCTGCTGGCC AGGCCGAACC CGACAGAGCC
CACTACAATA TCGTGACCTT CTGCTGCAAG TGCGACAGCA CCCTGCGGCT GTGCGTGCAG
AGCACCCACG TGGACATCCG GACCCTGGAA GATCTGCTGA TGGGCACCCT GGGCATCGTG
TGCCCCATCT GCAGCCAGAA GCCCGGCACC ACCCTGGAAC AGCAGTACAA CAAGCCCCTG
TGCGACCTGC TGATCCGGTG CATCAACTGC CAGAAACCCC TGTGCCCCGA GGAAAAGCAG
CGGCACCTGG ACAAGAAGCA GCGGTTCCAC AACATCCGGG GCAGATGGAC AGGCAGATGC
ATGAGCTGCT GCAGAAGCAG CCGGACCAGA CGGGAAACCC AGATGCACGG CGACACCCCC
ACCCTGCACG AGTACATGCT GGACCTGCAG CCCGAGACAA CCGACCTGTA CTGCTACGAG
CAGCTGAACG ACAGCAGCGA GGAAGAGGAC GAGATTGACG GACCCGCTGG ACAGGCCGAG
CCTGACCGGG CTCACTATAA CATCGTGACA TTTTGCTGTC AGCTCTGTAC TGAACTCCAG
ACAACAATTC ACGATATTAT TCTCGAATGT GTGTATTGTA AACAGCAGCT CCTGCGGAGA
GAGGTGTACG ACTTCGCCTT CCGGGACCTC TGCATCGTGT ATCGGGACGG CAACCCCTAC
GCCGTGTGCG ACAAGTGCCT GAAGTTCTAC AGCAAGATCA GCGAGTACCG GCACTACTGC
TACAGCCTGT ACGGAACAAC ACTCGAACAG CAGTATAACA AACCACTCTG TGATCTGCTG
ATTCGCTGTA TCAATTGTCA GAAGTGATAA SEQ ID NO: 3 (HPV16 E2E6E7SH, amino acid sequence of HPV16 E2/E6/E7
designer polypeptide)
METLCQRLNVCQDKILTHYENDSTDLRDHIDYWKHMRLECAIYYKAREMGFKHINHQVVPTLAVSKNKALQ
AIELQLTLETIYNSQYSNEKWTLQDVSLEVYLTAPTGCIKKHGYTVEVQFDGDICNTMHYTNWTHIYICEE
ASVTVVEGQVDYYGLYYVHEGIRTYFVQFKDDAEKYSKNKVWEVHAGGQVILCPTSVFSSNEVSSPEIIRQ
HLANHPAATHTKAVALGTEETQTTIQRPRSEPDTGNPCHTTKLLHRDSVDSAPILTAFNSSHKGRINCNSN
TTPIVHLKVDANTLMRLRYRFKKHCTLYTAVSSTWHWTGHNVKHKSAIVTLTYDSEWQRDQFLSQVKIPKT
ITVSTGFMSIMHQKRTAMFQDPQERPRKLPQLCTELQTTIHDIILECVYCKQQLEDEIDGPAGQAEPDRAH
YNIVTFCCKCDSTLRLCVQSTHVDIRTLEDLLMGTLGIVCPICSQKPGTTLEQQYNKPLCDLLIRCINCQK
PLCPEEKQRHLDKKQRFHNIRGRWTGRCMSCCRSSRTRRETQMHGDTPTLHEYMLDLQPETTDLYCYEQLN
```

TABLE I-continued sequences

DSSEEEDEIDGPAGQAEPDRAHYNIVTFCCQLCTELQTTIHDIILECVYCKQQLLRREVYDFAFRDLCIVY
RDGNPYAVCDKCLKFYSKISEYRHYCYSLYGTTLEQQYNKPLCDLLIRCINCQK

SEQ ID NO: 4 (HPV16 E2E6E7SH, nucleotide sequence encoding HPV16
E2/E6/E7 designer polypeptide
ATGGAAACCCTGTGCCAGCGGCTGAACGTGTGCCAGGACAAGATCCTGACCCACTACGAGAACGACAGCAC
CGACCTGCGGGACCACATCGACTACTGGAAGCACATGCGGCTGGAATGCGCCATCTACTACAAGGCCAGAG
AGATGGGCTTCAAGCACATCAACCACCAGGTGGTGCCCACCCTGGCCGTGTCCAAGAACAAGGCCCTGCAG
GCCATCGAGCTGCAGCTGACCCTGGAAACCATCTACAACAGCCAGTACAGCAACGAGAAGTGGACCCTGCA
GGACGTGTCCCTGGAAGTGTACCTGACCGCTCCCACCGGCTGCATCAAGAAACACGGCTACACCGTGGAAG
TGCAGTTCGACGGCGACATCTGCAACACCATGCACTACACCAACTGGACCCACATCTACATCTGCGAAGAG
GCCAGCGTGACCGTGGTGGAAGGCCAGGTGGACTACTACGGCCTGTACTACGTGCACGAGGGCATCCGGAC
CTACTTCGTGCAGTTCAAGGACGACGCCGAGAAGTACAGCAAGAACAAAGTGTGGGAGGTGCACGCTGGCG
GCCAGGTCATCCTGTGCCCCACCAGCGTGTTCAGCAGCAACGAGGTGTCCAGCCCCGAGATCATCCGGCAG
CACCTGGCCAATCACCCTGCCGCCACCCACACAAAGGCCGTGGCCCTGGGCACCGAGGAAACCCAGACCAC
CATCCAGCGGCCCAGAAGCGAGCCCGACACCGGCAATCCCTGCCACACCACCAAGCTGCTGCACCGGGACA
GCGTGGACAGCGCCCCTATCCTGACCGCCTTCAACAGCAGCCACAAGGGCCGGATCAACTGCAACAGCAAC
ACCACCCCCATCGTGCACCTGAAGGTGGACGCCAACACCCTGATGCGGCTGCGGTACAGATTCAAGAAGCA
CTGCACCCTGTACACCGCCGTGTCCTCCACCTGGCACTGGACCGGCCACAACGTGAAGCACAAGAGCGCCA
TCGTGACCCTGACCTACGACAGCGAGTGGCAGCGGGACCAGTTCCTGAGCCAGGTCAAAATCCCCAAGACC
ATCACCGTGTCCACCGGCTTCATGAGCATCATGCACCAGAAACGGACCGCCATGTTCCAGGACCCCCAGGA
ACGGCCCAGAAAGCTGCCCCAGCTGTGCACCGAGCTGCAGACCACCATCCACGACATCATCCTGGAATGCG
TGTACTGCAAGCAGCAGCTGGAAGATGAGATCGACGGCCCTGCTGGCCAGGCCGAACCCGACAGAGCCCAC
TACAATATCGTGACCTTCTGCTGCAAGTGCGACAGCACCCTGCGGCTGTGCGTGCAGAGCACCCACGTGGA
CATCCGGACCCTGGAAGATCTGCTGATGGGCACCCTGGGCATCGTGTGCCCCATCTGCAGCCAGAAGCCCG
GCACCACCCTGGAACAGCAGTACAACAAGCCCCTGTGCGACCTGCTGATCCGGTGCATCAACTGCCAGAAA
CCCCTGTGCCCCGAGGAAAAGCAGCGGCACCTGGACAAGAAGCAGCGGTTCCACAACATCCGGGGCAGATG
GACAGGCAGATGCATGAGCTGCTGCAGAAGCAGCCGGACCAGACGGGAAACCAGATGCACGGCGACACCC
CCACCCTGCACGAGTACATGCTGGACCTGCAGCCCGAGACAACCGACCTGTACTGCTACGAGCAGCTGAAC
GACAGCAGCGAGGAAGAGGACGAGATTGACGGACCCCGCTGGACAGGCCGAGCCTGACCGGGCTCACTATAA
CATCGTGACATTTTGCTGTCAGCTCTGTACTGAACTCCAGACAACAATTCACGATATTATTCTCGAATGTG
TGTATTGTAAACAGCAGCTCCTGCGGAGAGAGGTGTACGACTTCGCCTTCCGGGACCTCTGCATCGTGTAT
CGGGACGGCAACCCCTACGCCGTGTGCGACAAGTGCCTGAAGTTCTACAGCAAGATCAGCGAGTACCGGCA
CTACTGCTACAGCCTGTACGGAACAACACTCGAACAGCAGTATAACAAACCACTCTGTGATCTGCTGATTC
GCTGTATCAATTGTCAGAAGTGATAA SEQ ID NO: 5 (HPV16 E6E7E2SH, amino acid sequence encoding HPV16
E6/E7/E2 designer polypeptide
MHQKRTAMFQDPQERPRKLPQLCTELQTTIHDIILECVYCKQQLEDEIDGPAGQAEPDRAHYNIVTFCCKC
DSTLRLCVQSTHVDIRTLEDLLMGTLGIVCPICSQKPGTTLEQQYNKPLCDLLIRCINCQKPLCPEEKQRH
LDKKQRFHNIRGRWTGRCMSCCRSSRTRRETQMHGDTPTLHEYMLDLQPETTDLYCYEQLNDSSEEEDEID
GPAGQAEPDRAHYNIVTFCCQLCTELQTTIHDIILECVYCKQQLLRREVYDFAFRDLCIVYRDGNPYAVCD
KCLKFYSKISEYRHYCYSLYGTTLEQQYNKPLCDLLIRCINCQKMETLCQRLNVCQDKILTHYENDSTDLR
DHIDYWKHMRLECAIYYKAREMGFKHINHQVVPTLAVSKNKALQAIELQLTLETIYNSQYSNEKWILQDVS
LEVYLTAPTGCIKKHGYTVEVQFDGDICNTMHYTNWTHIYICEEASVTVVEGQVDYYGLYYVHEGIRTYFV
QFKDDAEKYSKNKVWEVHAGGQVILCPTSVFSSNEVSSPEIIRQHLANHPAATHTKAVALGTEETQTTIQR
PRSEPDTGNPCHTTKLLHRDSVDSAPILTAFNSSHKGRINCNSNTTPIVHLKVDANTLMRLRYRFKKHCTL
YTAVSSTWHWTGHNVKHKSAIVTLTYDSEWQRDQFLSQVKIPKTITVSTGFMSI SEQ ID NO: 6 (HPV16 E6E7E2SH, nucleotide sequence encoding HPV16
E6/E7/E2 designer polypeptide
ATGCACCAGAAACGGACCGCCATGTTCCAGGACCCCCAGGAACGGCCCAGAAAGCTGCCCCAGCTGTGCAC
CGAGCTGCAGACCACCATCCACGACATCATCCTGGAATGCGTGTACTGCAAGCAGCAGCTGGAAGATGAGA
TCGACGGCCCTGCTGGCCAGGCCGAACCCGACAGAGCCCACTACAATATCGTGACCTTCTGCTGCAAGTGC
GACAGCACCCTGCGGCTGTGCGTGCAGAGCACCCACGTGGACATCCGGACCCTGGAAGATCTGCTGATGGG
CACCCTGGGCATCGTGTGCCCCATCTGCAGCCAGAAGCCCGGCACCACCCTGGAACAGCAGTACAACAAGC
CCCTGTGCGACCTGCTGATCCGGTGCATCAACTGCCAGAAACCCCTGTGCCCCGAGGAAAAGCAGCGGCAC
CTGGACAAGAAGCAGCGGTTCCACAACATCCGGGGCAGATGGACAGGCAGATGCATGAGCTGCTGCAGAAG
CAGCCGGACCAGACGGGAAACCCAGATGCACGGCGACACCCCCACCCTGCACGAGTACATGCTGGACCTGC
AGCCCGAGACAACCGACCTGTACTGCTACGAGCAGCTGAACGACAGCAGCGAGGAAGAGGACGAGATTGAC
GGACCCGCTGGACAGGCCGAGCCTGACCGGGCTCACTATAACATCGTGACATTTTGCTGTCAGCTCTGTAC
TGAACTCCAGACAACAATTCACGATATTATTCTCGAATGTGTGTATTGTAAACAGCAGCTCCTGCGGAGAG
AGGTGTACGACTTCGCCTTCCGGGACCTCTGCATCGTGTATCGGGACGGCAACCCCTACGCCGTGTGCGAC
AAGTGCCTGAAGTTCTACAGCAAGATCAGCGAGTACCGGCACTACTGCTACAGCCTGTACGGAACAACACT
CGAACAGCAGTATAACAAACCACTCTGTGATCTGCTGATTCGCTGTATCAATTGTCAGAAGATGGAAACCC
TGTGCCAGCGGCTGAACGTGTGCCAGGACAAGATCCTGACCCACTACGAGAACGACAGCACCGACCTGCGG
GACCACATCGACTACTGGAAGCACATGCGGCTGGAATGCGCCATCTACTACAAGGCCAGAGAGATGGGCTT
CAAGCACATCAACCACCAGGTGGTGCCCACCCTGGCCGTGTCCAAGAACAAGGCCCTGCAGGCCATCGAGC
TGCAGCTGACCCTGGAAACCATCTACAACAGCCAGTACAGCAACGAGAAGTGGACCCTGCAGGACGTGTCC
CTGGAAGTGTACCTGACCGCTCCCACCGGCTGCATCAAGAAACACGGCTACACCGTGGAAGTGCAGTTCGA
CGGCGACATCTGCAACACCATGCACTACACCAACTGGACCCACATCTACATCTGCGAAGAGGCCAGCGTGA
CCGTGGTGGAAGGCCAGGTGGACTACTACGGCCTGTACTACGTGCACGAGGGCATCCGGACCTACTTCGTG
CAGTTCAAGGACGACGCCGAGAAGTACAGCAAGAACAAAGTGTGGGAGGTGCACGCTGGCGGCCAGGTCAT
CCTGTGCCCCACCAGCGTGTTCAGCAGCAACGAGGTGTCCAGCCCCGAGATCATCCGGCAGCACCTGGCCA
ATCACCCTGCCGCCACCCACACAAAGGCCGTGGCCCTGGGCACCGAGGAAACCCAGACCACCATCCAGCGG
CCCAGAAGCGAGCCCGACACCGGCAATCCCTGCCACACCACCAAGCTGCTGCACCGGGACAGCGTGGACAG
CGCCCCTATCCTGACCGCCTTCAACAGCAGCCACAAGGGCCGGATCAACTGCAACAGCAACACCACCCCCA
TCGTGCACCTGAAGGTGGACGCCAACACCCTGATGCGGCTGCGGTACAGATTCAAGAAGCACTGCACCCTG TABLE I-continued sequences TACACCGCCGTGTCCTCCACCTGGCACTGGACCGGCCACAACGTGAAGCACAAGAGCGCCATCGTGACCCT
GACCTACGACAGCGAGTGGCAGCGGGACCAGTTCCTGAGCCAGGTCAAAATCCCCAAGACCATCACCGTGT
CCACCGGCTTCATGAGCATCTGATAA SEQ ID NO: 7 (IgE leader peptide amino acid sequence)
MDWTWILFLVAAATRVHS SEQ ID NO: 8 (nucleotide sequence encoding IgE leader peptide)
ATGGACTGGACCTGGATCCTGTTCCTGGTGGCTGCCGCAACCCGGGTGCACAGC SEQ ID NO: 9 (aa HAVT20 leader peptide amino acid sequence)
MACPGFLWALVISTCLEFSMA SEQ ID NO: 10 (nucleotide sequence encoding HAVT20 leader peptide)
ATGGCCTGCCCCGGCTTTCTGTGGGCCCTGGTCATCAGCACCTGTCTGGAATTCAGCATGGCC SEQ ID NO: 11 (2xTetO-containing sequence)
GAGCTCTCCCTATCAGTGATAGAGATCTCCCTATCAGTGATAGAGATCGTCGAC SEQ ID NO: 12 (CuO-containing sequence)
AACAAACAGACAATCTGGTCTGTTTGTA SEQ ID NO: 13 (CMV promoter present in pAdApt26 and pAdApt35 plasmids)
TCAATATTGGCCATTAGCCATATTATTCATTGGTTATATAGCATAAATCAATATTGGCTATTGGCCATTGC
ATACGTTGTATCCATATCATAATATGTACATTTATATTGGCTCATGTCCAACATTACCGCCATGTTGACAT
TGATTATTGACTAGTTATTAATAGTAATCAATTACGGGGTCATTAGTTCATAGCCCATATATGGAGTTCCG
CGTTACATAACTTACGGTAAATGGCCCGCCTGGCTGACCGCCCAACGACCCCCGCCCATTGACGTCAATAA
TGACGTATGTTCCCATAGTAACGCCAATAGGGACTTTCCATTGACGTCAATGGGTGGAGTATTTACGGTAA
ACTGCCCACTTGGCAGTACATCAAGTGTATCATATGCCAAGTACGCCCCCTATTGACGTCAATGACGGTAA
ATGGCCCGCCTGGCATTATGCCCAGTACATGACCTTATGGGACTTTCCTACTTGGCAGTACATCTACGTAT
TAGTCATCGCTATTACCATGGTGATGCGGTTTTGGCAGTACATCAATGGGCGTGGATAGCGGTTTGACTCA
CGGGGATTTCCAAGTCTCCACCCCATTGACGTCAATGGGAGTTTGTTTTGGCACCAAAATCAACGGGACTT
TCCAAAATGTCGTAACAACTCCGCCCCATTGACGCAAATGGGCGGTAGGCGTGTACGGTGGGAGGTCTATA
TAAGCAGAGCTCGTTTAGTGAACCGTCAGATCGCCTGGAGACGCCATCCACGCTGTTTTGACCTCCATAGA
AGACACCGGGACCGATCCAGCCTCCGCGGCCGGGAACGGTGCATTGGA SEQ ID NO: 14 (TetR, nucleotide sequence encoding amino acid sequence
of TetR polypeptide expressed by pcDNA™6/TR)
ATGTCTAGATTAGATAAAAGTAAAGTGATTAACAGCGCATTAGAGCTGCTTAATGAGGTCGGAATCGAAGG
TTTAACAACCCGTAAACTCGCCCAGAAGCTAGGTGTAGAGCAGCCTACATTGTATTGGCATGTAAAAAATA
AGCGGGCTTTGCTCGACGCCTTAGCCATTGAGATGTTAGATAGGCACCATACTCACTTTTGCCCTTTAGAA
GGGGAAAGCTGGCAAGATTTTTTACGTAATAACGCTAAAAGTTTTAGATGTGCTTTACTAAGTCATCGCGA
TGGAGCAAAAGTACATTTAGGTACACGGCCTACAGAAAAACAGTATGAAACTCTCGAAAATCAATTAGCCT
TTTTATGCCAACAAGGTTTTTCACTAGAGAATGCATTATATGCACTCAGCGCTGTGGGGCATTTTACTTTA
GGTTGCGTATTGGAAGATCAAGAGCATCAAGTCGCTAAAGAAGAAAGGGAAACACCTACTACTGATAGTAT
GCCGCCATTATTACGACAAGCTATCGAATTATTTGATCACCAAGGTGCAGAGCCAGCCTTCTTATTCGGCC
TTGAATTGATCATATGCGGATTAGAAAAACAACTTAAATGTGAAAGTGGGTCCGCGTACAGCGGATCCCGG
GAATTCAGATCTTATTAA SEQ ID NO: 15 (TetR, amino acid sequence of TetR polypeptide expressed
by pcDNA™6/TR)
MSRLDKSKVINSALELLNEVGIEGLTTRKLAQKLGVEQPTLYWHVKNKRALLDALAIEMLDRHHTHFCPLE
GESWQDFLRNNAKSFRCALLSHRDGAKVHLGTRPTEKQYETLENQLAFLCQQGFSLENALYALSAVGHFTL
GCVLEDQEHQVAKEERETPTTDSMPPLLRQAIELFDHQGAEPAFLFGLELIICGLEKQLKCESGSAYSGSR
EFRSY SEQ ID NO: 16 (CymR, nucleotide sequence encoding amino acid sequence
of CymR polypeptide)
ATGTCTCCCAAACGACGGACTCAAGCGGAAAGGGCAATGGAAACTCAGGGTAAGCTGATTGCCGCGGCTCT
GGGAGTGCTGCGAGAGAAAGGGTATGCCGGGTTTCGCATAGCCGACGTTCCTGGAGCTGCAGGCGTAAGCA
GAGGAGCCCAATCTCATCACTTTCCGACCAAGCTGGAGCTTTTGCTGGCTACCTTCGAATGGCTGTACGAG
CAGATCACGGAAAGGAGTCGTGCTAGGCTGGCCAAGCTGAAACCCGAGGATGATGTCATTCAGCAGATGCT
GGACGATGCAGCCGAGTTCTTCCTGGACGACGACTTCAGCATCAGTCTGGACCTCATCGTAGCCGCAGATC
GCGATCCAGCTTTGCGCGAGGGCATACAGAGAACAGTCGAGCGGAATCGGTTTGTGGTGGAGGACATGTGG
CTTGGTGTTCTGGTGAGCAGAGGCCTCTCACGGGATGATGCCGAGGACATCCTGTGGCTGATCTTTAACTC
CGTCAGAGGGTTGGCAGTGAGGTCCCTTTGGCAGAAGGACAAAGAACGGTTTGAACGTGTGCGAAACTCAA
CACTCGAGATTGCTAGGGAACGCTACGCCAAGTTCAAGAGATGA SEQ ID NO: 17 (CymR, amino acid sequence of CymR polypeptide)
MSPKRRTQAERAMETQGKLIAAALGVLREKGYAGFRIADVPGAAGVSRGAQSHHFPTKLELLLATFEWLYE
QITERSRARLAKLKPEDDVIQQMLDDAAEFFLDDDFSISLDLIVAADRDPALREGIQRTVERNRFVVEDMW
LGVLVSRGLSRDDAEDILWLIFNSVRGLAVRSLWQKDKERFERVRNSTLEIARERYAKFKR SEQ ID NO: 18 (HPV16 E6, aa41-65)
KQQLLRREVYDFAFRDLCIVYRDGN SEQ ID NO: 19 (HPV16 E7 aa 43-77)
GQAEPDRAHYNIVTFCCKCDSTLRLCVQSTHVDIR TABLE I-continued sequences SEQ ID NO: 20 (amino acid sequences of HPV18-E6E7SH designer sequence)
MARFEDPTRRPYKLPDLCTELNTSLQDIEITCVYCKTVLDLLCHEQLSDSEEENDEIDGVNHQHLPARRAE
PQRHTMLCMCCKCEARIELVVESSADDLRAFQQLFLNTLSFVCPWCASQHYSDSVYGDTLEKLTNTGLYNL
LIRCLRCQKPLNPAEKLRHLNEKRRFHNIAGHYRGQCHSCCNRARQERLQRRRETMHGPKATLQDIVLHLE
PQNEIPVDLLCHEQLSDSEEENDEIDGVNPDLCTELNTSLQDIEITCVYCKTVLELTEVFEFAFKDLFVVY
RDSIPHAACHKCIDFYSRIRELRHYSDSVYGDTLEKLTNTGLYNLLI SEQ ID NO: 21 (nucleotide sequences of HPV18-E6E7SH designer sequence)
ATGGCCAGATTCGAGGACCCCACCAGACGGCCCTACAAGCTGCCCGACCTGTGCACCGAGCTGAACACAT
TCTGCAGGACATCGAGATCACATGCGTGTACTGCAAGACCGTGCTGGACCTGCTGTGCCACGAGCAGCTGT
CCGACTCCGAGGAAGAAAACGACGAGATCGACGGCGTGAACCATCAGCATCTGCCCGCCAGACGGGCCGAG
CCCCAGAGACACACCATGCTGTGTCATGTGCTGCAAGTGCGAGGCCCGGATTGAGCTGGTGGTGGAAAGCAG
CGCCGACGACCTGCGGGCCTTCCAGCAGCTCTTTCTGAATACCCTGAGCTTCGTGTGCCCTTGGTGCGCCA
GCCAGCACTACAGCGACTCCGTGTACGGCGATACCCTGGAAAAGCTGACCAATACCGGCCTGTATAACCTG
CTGATCCGGTGCCTGCGGTGCCAGAAGCCCCTGAATCCCGCCGAGAAACTGAGACACCTGAACGAGAAGCG
GCGGTTCCACAATATCGCCGGCCACTACAGAGGCCAGTGCCACAGCTGCTGCAACCGGGCCAGACAGGAAC
GGCTGCAGCGGAGGCGGGAAACCATGCACGGACCCAAGGCCACCCTCCAGGACATTGTCCTGCACCTGGAA
CCCCAGAACGAGATCCCCGTCGATCTGCTGTGTCATGAACAGCTCAGCGACAGCGAAGAGGAAAATGACGA
AATTGACGGGGTCAACCCTGACCTCTGTACCGAACTCAATACCAGTCTCCAGGATATCGAAATTACCTGTG
TCTACTGTAAAACCGTCCTCGAGCTGACCGAGGTGTTCGAGTTCGCCTTCAAGGACCTGTTTGTGGTGTAC
AGAGACAGCATCCCCCACGCCGCCTGCCACAAGTGCATCGACTTCTACAGCCGGATCAGAGAGCTGCGGCA
CTACTCCGATTCTGTGTATGGCGACACACTCGAGAAGCTCACAAACACAGGACTGTACAATCTGCTCATCT
GATAA SEQ ID NO: 22 (amino acid sequences of HPV18-E2E6E7SH designer
sequence)
MQTPKETLSERLSALQDKIIDHYENDSKDIDSQIQYWQLIRWENAIFFAAREHGIQTLNHQVVPAYNISKS
KAHKAIELQMALQGLAQSAYKTEDWILQDTCEELWNTEPTHCFKKGGQTVQVYFDGNKDNCMTYVAWDSVY
YMTDAGTWDKTATCVSHRGLYYVKEGYNTFYIEFKSECEKYGNTGTWEVHFGNNVIDCNDSMCSTSDDTVS
ATQLVKQLQHTPSPYSSTVSVGTAKTYGQTSAATRPGHCGLAEKQHCGPVNPLLGAATPTGNNKRRKLCSG
NTTPIIHLKVDRNSLMRLRYRLRKHSDHYRDISSTWHWTGAGNEKTGILTVTYHSETQRTKFLNTVAIPDS
VQILVGYMTMMARFEDPTRRPYKLPDLCTELNTSLQDIEITCVYCKTVLDLLCHEQLSDSEEENDEIDGVN
HQHLPARRAEPQRHTMLCMCCKCEARIELVVESSADDLRAFQQLFLNTLSFVCPWCASQHYSDSVYGDTLE
KLTNTGLYNLLIRCLRCQKPLNPAEKLRHLNEKRRFHNIAGHYRGQCHSCCNRARQERLQRRRETMHGPKA
TLQDIVLHLEPQNEIPVDLLCHEQLSDSEEENDEIDGVNPDLCTELNTSLQDIEITCVYCKTVLELTEVFE
FAFKDLFVVYRDSIPHAACHKCIDFYSRIRELRHYSDSVYGDTLEKLTNTGLYNLLI*

SEQ ID NO: 23 (nucleotide sequences of HPV18-E2E6E7SH designer
sequence)
ATGCAGACCCCCAAAGAGACACTGAGCGAGCGGCTGAGCGCCCTGCAGGACAAGATCATCGACCACTACGA
GAACGACAGCAAGGACATCGACAGCCAGATCCAGTACTGGCAGCTGATCAGATGGGAGAACGCCATCTTCT
TCGCCGCCAGAGAGCACGGCATCCAGACCCTGAACCACCAGGTGGTGCCCGCCTACAACATCAGCAAGAGC
AAGGCCCACAAGGCTATCGAGCTGCAGATGGCCCTGCAGGGCCTGGCCCAGAGCGCCTACAAGACCGAGGA
CTGGACCCTGCAGGATACCTGCGAGGAACTGTGGAACACCGAGCCCACCCACTGCTTCAAGAAAGGCGGCC
AGACCGTGCAGGTGTACTTCGACGGCAACAAGGACAACTGCATGACCTACGTGGCCTGGGACAGCGTGTAC
TACATGACCGACGCCGGCACCTGGGACAAGACCGCCACCTGTGTGTCCCACCGGGGCCTGTACTACGTGAA
AGAGGGCTACAACACCTTCTACATCGAGTTCAAGAGCGAGTGCGAGAAGTACGGCAACACATGGG
AGGTGCACTTCGGCAACAACGTGATCGACTGCAACGACAGCATGTGCAGCACCAGCGACGACACCGTGTCC
GCCACCCAGCTGGTGAAACAGCTGCAGCACACCCCCAGCCCCTACAGCAGCACCGTGTCTGTGGGCACCGC
CAAGACCTACGGCCAGACCAGCGCCGCCACCAGACCTGGACACTGTGGCCTGGCCGAGAAGCAGCACTGCG
GCCCTGTGAACCCTCTGCTGGGAGCCGCCACCCCCACCGGCAACAACAGCGGAGAAAGCTGTGCAGCGGC
AACACCACCCCCATCATCCACCTGAAGGTGGACCGGAACAGCCTGATGCGGCTGCGGTACAGACTGCGGAA
GCACAGCGACCACTACCGGGACATCAGCAGCACCTGGCACTGGACCGGCGCTGGCAACGAGAAAACCGGCA
TCCTGACCGTGACCTACCACAGCGAAACCCAGCGGACCAAGTTCCTGAACACCGTGGCCATCCCCGACAGC
GTGCAGATCCTGGTGGGATATATGACCATGATGGCCAGATTCGAGGACCCCACCAGACGGCCCTACAAGCT
GCCCGACCTGTGCACCGAGCTGAACACATCTCTGCAGGACATCGAGATCACATGCGTGTACTGCAAGACCG
TGCTGGACCTGCTGTGCCACGAGCAGCTGTCCGACTCCGAGGAAGAAAACGACGAGATCGACGGCGTGAAC
CATCAGCATCTGCCCGCCAGACGGGCCGAGCCCCAGAGACACACCATGCTGTGCATGTGCTGCAAGTGCGA
GGCCCGGATTGAGCTGGTGGTGGAAAGCAGCGCCGACGACCTGCGGGCCTTCCAGCAGCTCTTTCTGAATA
CCCTGAGCTTCGTGTGCCCTTGGTGCGCCAGCCAGCACTACAGCGACTCCGTGTACGGCGATACCCTGGAA
AAGCTGACCAATACCGGCCTGTATAACCTGCTGATCCGGTGCCTGCGGTGCCAGAAGCCCCTGAATCCCGC
CGAGAAACTGAGACACCTGAACGAGAAGCGGCGGTTCCACAATATCGCCGGCCACTACAGAGGCCAGTGCC
ACAGCTGCTGCAACCGGGCCAGACAGGAACGGCTGCAGCGGAGGCGGGAAACCATGCACGGACCCAAGGCC
ACCCTCCAGGACATTGTCCTGCACCTGGAACCCCAGAACGAGATCCCCGTCGATCTGCTGTGTCATGAACA
GCTCAGCGACAGCGAAGAGGAAAATGACGAAATTGACGGGGTCAACCCTGACCTCTGTACCGAACTCAATA
CCAGTCTCCAGGATATCGAAATTACCTGTGTCTACTGTAAAACCGTCCTCGAGCTGACCGAGGTGTTCGAG
TTCGCCTTCAAGGACCTGTTTGTGGTGTACAGAGACAGCATCCCCCACGCCGCCTGCCACAAGTGCATCGA
CTTCTACAGCCGGATCAGAGAGCTGCGGCACTACTCCGATTCTGTGTATGGCGACACACTCGAGAAGCTCA
CAAACACAGGACTGTACAATCTGCTCATCTGATAA SEQ ID NO: 24 (amino acid sequence of 'HPV18DC2')
MHGPKATLQDIVLHLEPQNEIPVDLLCHEQLSDSEEENDEIDGVNHQHLPARRAEPQRHTSLQDIEITCVY
CKTVLELTEVFEFAFKDLFVVYRDSIPHAACHKCIDFYSRIRELRHYSDSVYGDTLEKLTNTGLYNLLIRC
LQRFEDPTRRPYKLPDLCTELNTSLQDIEITCVYCKTVLELTEVFEFADSEEENDEIDGVNHQHLPARRAE
PQRHTMLCMCCKCEARIELVVESSADDLRAFQQLFLNTLSFVCPWCASQSDSVYGDTLEKLTNTGLYNLLI
RCLRCQKPLNPAEKLRHLNEKRRFHNIAGHYRGQCHSCCNRARQERLQRRRETQ

What is claimed is:

1. A nucleic acid molecule encoding a first polypeptide comprising SEQ ID NO: 20.

2. The nucleic acid molecule of claim 1, wherein the first polypeptide further comprises at least one epitope of a human papillomavirus (HPV) E2 protein.

3. The nucleic acid molecule of claim 2, wherein the first polypeptide comprises HPV18 E2 protein having a deletion or mutation in its DNA binding domain and/or a mutation in its transactivation domain.

4. The nucleic acid molecule of claim 3, wherein the first polypeptide comprises SEQ ID NO: 22.

5. The nucleic acid molecule of claim 1, comprising SEQ ID NO: 21.

6. The nucleic acid molecule of claim 1, comprising SEQ ID NO: 23.

7. A vector comprising the nucleic acid molecule of claim 1, wherein nucleic acid encoding the first polypeptide is operably linked to a promoter.

8. The vector of claim 7, wherein the vector is a recombinant adenovirus.

9. The vector of claim 7, wherein the promoter is operably coupled to a repressor operator sequence, to which a repressor protein can bind in order to repress expression of the promoter in the presence of the repressor protein.

10. The vector of claim 7, further comprising:
nucleic acid encoding a second polypeptide operably linked to a promoter, wherein the second polypeptide comprises SEQ ID NO: 1.

11. The vector of claim 10, wherein the second polypeptide comprises SEQ ID NO: 3 or SEQ ID NO: 5.

12. The vector of claim 11,
wherein the first polypeptide comprises SEQ ID NO: 22, and
wherein the second polypeptide comprises SEQ ID NO: 3.

13. A vaccine composition comprising:
the vector of claim 7, and
a pharmaceutically acceptable excipient.

14. A vaccine composition comprising:
the vector of claim 7;
a second vector comprising a nucleic acid molecule encoding a second polypeptide operably linked to a promoter, wherein the second polypeptide comprises SEQ ID NO:1; and
a pharmaceutically acceptable excipient.

15. The vaccine composition of claim 14, wherein the second polypeptide comprises SEQ ID NO: 3 or SEQ ID NO: 5.

16. The vaccine composition of claim 15,
wherein the first vector encodes a polypeptide comprising SEQ ID NO: 22, and
wherein the second vector encodes a polypeptide comprising SEQ ID NO: 3.

17. A method of inducing an immune response against HPV in a subject, the method comprising:
administering to the subject the vaccine composition of claim 13.

18. A method of inducing an immune response against HPV in a subject, the method comprising administering to the subject:
a first vaccine composition comprising:
the vector of claim 7, and
a pharmaceutically acceptable excipient; and
a second vaccine composition comprising:
a vector comprising a nucleic acid molecule encoding a second polypeptide operably linked to a promoter, wherein the second polypeptide comprises SEQ ID NO: 1.

19. The method according to claim 18, wherein the second polypeptide comprises SEQ ID NO: 3 or SEQ ID NO: 5.

20. The method according to claim 19,
wherein the polypeptide encoded by the first vaccine composition comprises SEQ ID NO: 22, and
wherein the second polypeptide comprises SEQ ID NO: 3.

21. The method according to claim 17, the method further comprising:
administering the vaccine composition to the subject more than once.

22. The method according to claim 18, the method further comprising:
administering the first vaccine composition and/or the second vaccine composition to the subject more than once.

23. A method for treating a subject for persistent HPV infection, vulvar intraepithelial neoplasia (VIN), cervical intraepithelial neoplasia (CIN), vaginal intraepithelial neoplasia (VaIN), anal intraepithelial neoplasia (AIN), cervical cancer (such as cervical squamous cell carcinoma (SCC), oropharyngeal cancer, penile cancer, vaginal cancer and/or anal cancer, the method comprising:
administering to the subject the vaccine composition of claim 13.

24. A kit of parts comprising:
a first vaccine composition comprising:
the vector of claim 7, and
a pharmaceutically acceptable excipient; and
a second vaccine composition comprising:
a vector comprising a nucleic acid molecule encoding a second polypeptide operably linked to a promoter, wherein the second polypeptide comprises SEQ ID NO: 1.

25. The kit of parts of claim 24, wherein the second polypeptide comprises SEQ ID NO: 3 or SEQ ID NO: 5.

26. The kit of parts of claim 25,
wherein the polypeptide encoded by the first vaccine composition comprises SEQ ID NO: 22, and
wherein the second polypeptide comprises SEQ ID NO: 3.

27. A polypeptide comprising SEQ ID NO: 20.

28. The polypeptide of claim 27, wherein the polypeptide comprises SEQ ID NO: 22.

* * * * *

SEQUENCE LISTING

<160> NUMBER OF SEQ ID NOS: 24

<210> SEQ ID NO 1
<211> LENGTH: 328
<212> TYPE: PRT
<213> ORGANISM: Artificial Sequence
<220> FEATURE:
<223> OTHER INFORMATION: HPV16-E6E7SH designer polypeptide

<400> SEQUENCE: 1

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Glu Asp Glu Ile
        35                  40                  45

Asp Gly Pro Ala Gly Gln Ala Glu Pro Asp Arg Ala His Tyr Asn Ile
    50                  55                  60

Val Thr Phe Cys Cys Lys Cys Asp Ser Thr Leu Arg Leu Cys Val Gln
65                  70                  75                  80

Ser Thr His Val Asp Ile Arg Thr Leu Glu Asp Leu Leu Met Gly Thr
                85                  90                  95

Leu Gly Ile Val Cys Pro Ile Cys Ser Gln Lys Pro Gly Thr Thr Leu
            100                 105                 110

Glu Gln Gln Tyr Asn Lys Pro Leu Cys Asp Leu Leu Ile Arg Cys Ile
        115                 120                 125

Asn Cys Gln Lys Pro Leu Cys Pro Glu Glu Lys Gln Arg His Leu Asp
    130                 135                 140

Lys Lys Gln Arg Phe His Asn Ile Arg Gly Arg Trp Thr Gly Arg Cys
145                 150                 155                 160

Met Ser Cys Cys Arg Ser Ser Arg Thr Arg Arg Glu Thr Gln Met His
                165                 170                 175

Gly Asp Thr Pro Thr Leu His Glu Tyr Met Leu Asp Leu Gln Pro Glu
            180                 185                 190

Thr Thr Asp Leu Tyr Cys Tyr Glu Gln Leu Asn Asp Ser Ser Glu Glu
        195                 200                 205

Glu Asp Glu Ile Asp Gly Pro Ala Gly Gln Ala Glu Pro Asp Arg Ala
    210                 215                 220

His Tyr Asn Ile Val Thr Phe Cys Cys Gln Leu Cys Thr Glu Leu Gln
225                 230                 235                 240

Thr Thr Ile His Asp Ile Ile Leu Glu Cys Val Tyr Cys Lys Gln Gln
                245                 250                 255

Leu Leu Arg Arg Glu Val Tyr Asp Phe Ala Phe Arg Asp Leu Cys Ile
            260                 265                 270

Val Tyr Arg Asp Gly Asn Pro Tyr Ala Val Cys Asp Lys Cys Leu Lys
        275                 280                 285

Phe Tyr Ser Lys Ile Ser Glu Tyr Arg His Tyr Cys Tyr Ser Leu Tyr
    290                 295                 300

Gly Thr Thr Leu Glu Gln Gln Tyr Asn Lys Pro Leu Cys Asp Leu Leu
305                 310                 315                 320

Ile Arg Cys Ile Asn Cys Gln Lys
                325

<210> SEQ ID NO 2
<211> LENGTH: 990
<212> TYPE: DNA

<213> ORGANISM: Artificial Sequence
<220> FEATURE:
<223> OTHER INFORMATION: nt sequence encoding HPV16-E6E7SH designer polypeptide

<400> SEQUENCE: 2

```
atgcaccaga acggaccgc catgttccag accccccagg aacggcccag aaagctgccc      60
cagctgtgca ccgagctgca gaccaccatc cacgacatca tcctggaatg cgtgtactgc    120
aagcagcagc tggaagatga gatcgacggc cctgctggcc aggccgaacc cgacagagcc    180
cactacaata tcgtgacctt ctgctgcaag tgcgacagca ccctgcggct gtgcgtgcag    240
agcacccacg tggacatccg gaccctggaa gatctgctga tgggcaccct gggcatcgtg    300
tgccccatct gcagccagaa gcccggcacc accctggaac agcagtacaa caagcccctg    360
tgcgacctgc tgatccggtg catcaactgc agaaaccccc tgtgccccga ggaaaagcag    420
cggcacctgg acaagaagca gcggttccac aacatccggg gcagatggac aggcagatgc    480
atgagctgct gcagaagcag ccggaccaga cgggaaaccc agatgcacgg cgacaccccc    540
accctgcacg agtacatgct ggacctgcag cccgagacaa ccgacctgta ctgctacgag    600
cagctgaacg acagcagcga ggaagaggac gagattgacg acccgctgg acaggccgag    660
cctgaccggg ctcactataa catcgtgaca ttttgctgtc agctctgtac tgaactccag    720
acaacaattc acgatattat tctcgaatgt gtgtattgta acagcagct cctgcgcgaga    780
gaggtgtacg acttcgcctt ccgggacctc tgcatcgtgt atcgggacgg caacccctac    840
gccgtgtgcg acaagtgcct gaagttctac agcaagatca gcgagtaccg gcactactgc    900
tacagcctgt acggaacaac actcgaacag cagtataaca accactctg tgatctgctg    960
attcgctgta tcaattgtca gaagtgataa                                     990
```

<210> SEQ ID NO 3
<211> LENGTH: 693
<212> TYPE: PRT
<213> ORGANISM: Artificial Sequence
<220> FEATURE:
<223> OTHER INFORMATION: HPV16 E2E6E7SH designer polypeptide

<400> SEQUENCE: 3

```
Met Glu Thr Leu Cys Gln Arg Leu Asn Val Cys Gln Asp Lys Ile Leu
1               5                  10                  15

Thr His Tyr Glu Asn Asp Ser Thr Asp Leu Arg Asp His Ile Asp Tyr
            20                  25                  30

Trp Lys His Met Arg Leu Glu Cys Ala Ile Tyr Tyr Lys Ala Arg Glu
        35                  40                  45

Met Gly Phe Lys His Ile Asn His Gln Val Val Pro Thr Leu Ala Val
    50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
            100                 105                 110

His Gly Tyr Thr Val Glu Val Gln Phe Asp Gly Asp Ile Cys Asn Thr
        115                 120                 125

Met His Tyr Thr Asn Trp Thr His Ile Tyr Ile Cys Glu Glu Ala Ser
    130                 135                 140

Val Thr Val Val Glu Gly Gln Val Asp Tyr Tyr Gly Leu Tyr Tyr Val
```

```
                145                 150                 155                 160
            His Glu Gly Ile Arg Thr Tyr Phe Val Gln Phe Lys Asp Asp Ala Glu
                            165                 170                 175

Lys Tyr Ser Lys Asn Lys Val Trp Glu Val His Ala Gly Gly Gln Val
                            180                 185                 190

Ile Leu Cys Pro Thr Ser Val Phe Ser Ser Asn Glu Val Ser Ser Pro
                            195                 200                 205

Glu Ile Ile Arg Gln His Leu Ala Asn His Pro Ala Ala Thr His Thr
                            210                 215                 220

Lys Ala Val Ala Leu Gly Thr Glu Thr Gln Thr Thr Ile Gln Arg
            225                 230                 235                 240

Pro Arg Ser Glu Pro Asp Thr Gly Asn Pro Cys His Thr Thr Lys Leu
                            245                 250                 255

Leu His Arg Asp Ser Val Asp Ser Ala Pro Ile Leu Thr Ala Phe Asn
                            260                 265                 270

Ser Ser His Lys Gly Arg Ile Asn Cys Asn Ser Asn Thr Thr Pro Ile
                            275                 280                 285

Val His Leu Lys Val Asp Ala Asn Thr Leu Met Arg Leu Arg Tyr Arg
                            290                 295                 300

Phe Lys Lys His Cys Thr Leu Tyr Thr Ala Val Ser Ser Thr Trp His
            305                 310                 315                 320

Trp Thr Gly His Asn Val Lys His Lys Ser Ala Ile Val Thr Leu Thr
                            325                 330                 335

Tyr Asp Ser Glu Trp Gln Arg Asp Gln Phe Leu Ser Gln Val Lys Ile
                            340                 345                 350

Pro Lys Thr Ile Thr Val Ser Thr Gly Phe Met Ser Ile Met His Gln
                            355                 360                 365

Lys Arg Thr Ala Met Phe Gln Asp Pro Gln Glu Arg Pro Arg Lys Leu
                            370                 375                 380

Pro Gln Leu Cys Thr Glu Leu Gln Thr Thr Ile His Asp Ile Ile Leu
            385                 390                 395                 400

Glu Cys Val Tyr Cys Lys Gln Gln Leu Glu Asp Glu Ile Asp Gly Pro
                            405                 410                 415

Ala Gly Gln Ala Glu Pro Asp Arg Ala His Tyr Asn Ile Val Thr Phe
                            420                 425                 430

Cys Cys Lys Cys Asp Ser Thr Leu Arg Leu Cys Val Gln Ser Thr His
                            435                 440                 445

Val Asp Ile Arg Thr Leu Glu Asp Leu Leu Met Gly Thr Leu Gly Ile
            450                 455                 460

Val Cys Pro Ile Cys Ser Gln Lys Pro Gly Thr Thr Leu Glu Gln Gln
            465                 470                 475                 480

Tyr Asn Lys Pro Leu Cys Asp Leu Leu Ile Arg Cys Ile Asn Cys Gln
                            485                 490                 495

Lys Pro Leu Cys Pro Glu Glu Lys Gln Arg His Leu Asp Lys Lys Gln
                            500                 505                 510

Arg Phe His Asn Ile Arg Gly Arg Trp Thr Gly Arg Cys Met Ser Cys
                            515                 520                 525

Cys Arg Ser Ser Arg Thr Arg Arg Glu Thr Gln Met His Gly Asp Thr
                            530                 535                 540

Pro Thr Leu His Glu Tyr Met Leu Asp Leu Gln Pro Glu Thr Thr Asp
            545                 550                 555                 560

Leu Tyr Cys Tyr Glu Gln Leu Asn Asp Ser Ser Glu Glu Glu Asp Glu
                            565                 570                 575
```

```
Ile Asp Gly Pro Ala Gly Gln Ala Glu Pro Asp Arg Ala His Tyr Asn
            580                 585                 590

Ile Val Thr Phe Cys Cys Gln Leu Cys Thr Glu Leu Gln Thr Thr Ile
        595                 600                 605

His Asp Ile Ile Leu Glu Cys Val Tyr Cys Lys Gln Gln Leu Leu Arg
    610                 615                 620

Arg Glu Val Tyr Asp Phe Ala Phe Arg Asp Leu Cys Ile Val Tyr Arg
625                 630                 635                 640

Asp Gly Asn Pro Tyr Ala Val Cys Asp Lys Cys Leu Lys Phe Tyr Ser
                645                 650                 655

Lys Ile Ser Glu Tyr Arg His Tyr Cys Tyr Ser Leu Tyr Gly Thr Thr
            660                 665                 670

Leu Glu Gln Gln Tyr Asn Lys Pro Leu Cys Asp Leu Leu Ile Arg Cys
        675                 680                 685

Ile Asn Cys Gln Lys
    690

<210> SEQ ID NO 4
<211> LENGTH: 2085
<212> TYPE: DNA
<213> ORGANISM: Artificial Sequence
<220> FEATURE:
<223> OTHER INFORMATION: nt sequence encoding HPV16 E2E6E7SH designer
      polypeptide

<400> SEQUENCE: 4
atggaaaccc tgtgccagcg gctgaacgtg tgccaggaca gatcctgac  ccactacgag      60 aacgacagca ccgacctgcg ggaccacatc gactactgga agcacatgcg gctggaatgc     120
gccatctact acaaggccag agagatgggc ttcaagcaca tcaaccacca ggtggtgccc     180
accctggccg tgtccaagaa caaggccctg caggccatcg agctgcagct gaccctggaa     240
accatctaca cagccagta cagcaacgag aagtggaccc tgcaggacgt gtccctggaa      300
gtgtacctga ccgctcccac cggctgcatc aagaaacacg gctacaccgt ggaagtgcag     360
ttcgacggcg acatctgcaa caccatgcac tacaccaact ggacccacat ctacatctgc     420
gaagaggcca gcgtgaccgt ggtggaaggc caggtggact actacggcct gtactacgtg     480
cacgagggca tccggaccta cttcgtgcag ttcaaggacg acgccgagaa gtacagcaag     540
aacaaagtgt gggaggtgca cgctggcggc caggtcatcc tgtgccccac cagcgtgttc     600
agcagcaacg aggtgtccag ccccgagatc atccggcagc acctggccaa tcaccctgcc     660
gccacccaca caaaggccgt ggccctgggc accgagaaa cccagaccac catccagcgg     720
cccgaaagcg agcccgacac cggcaatccc tgccacacca ccaagctgct gcaccgggac     780
agcgtggaca gcgcccctat cctgaccgcc ttcaacagca gccacaaggg ccggatcaac     840
tgcaacagca caccaccc catcgtgcac ctgaaggtgg acgccaacac cctgatgcgg     900
ctgcggtaca gattcaagaa gcactgcacc ctgtacaccg ccgtgtcctc cacctggcac     960
tggaccggcc acaacgtgaa gcacaagagc gccatcgtga ccctgaccta cgacagcgag    1020
tggcagcggg accagttcct gagccaggtc aaaatcccca gaccatcac cgtgtccacc     1080 ggcttcatga gcatcatgca ccagaaacgg accgccatgt ccaggaccc ccaggaacgg    1140 cccgagaaagc tgcccagct gtgcaccgag ctgcagacca ccatccacga catcatcctg    1200
gaatgcgtgt actgcaagca gcagctgaa gatgagatcg acggccctgc tggccaggcc    1260
gaacccgaca gagcccacta caatatcgtg accttctgct gcaagtgcga cagcaccctg    1320
```

-continued

```
cggctgtgcg tgcagagcac ccacgtggac atccggaccc tggaagatct gctgatgggc    1380
accctgggca tcgtgtgccc catctgcagc cagaagcccg gcaccaccct ggaacagcag    1440
tacaacaagc ccctgtgcga cctgctgatc cggtgcatca actgccagaa acccctgtgc    1500
cccgaggaaa agcagcggca cctggacaag aagcagcggt ccacaacat ccggggcaga    1560 tggacaggca gatgcatgag ctgctgcaga agcagccgga ccagacggga aacccagatg    1620
cacggcgaca cccccaccct gcacgagtac atgctggacc tgcagcccga dacaaccgac    1680
ctgtactgct acgagcagct gaacgacagc agcgaggaag aggacgagat tgacggaccc    1740
gctggacagg ccgagcctga ccgggctcac tataacatcg tgacattttg ctgtcagctc    1800
tgtactgaac tccagacaac aattcacgat attattctcg aatgtgtgta ttgtaaacag    1860
cagctcctgc ggagagaggt gtacgacttc gccttccggg acctctgcat cgtgtatcgg    1920
gacggcaacc cctacgccgt gtgcgacaag tgcctgaagt tctacagcaa gatcagcgag    1980
taccggcact actgctacag cctgtacgga acaacactcg aacagcagta taacaaacca    2040
ctctgtgatc tgctgattcg ctgtatcaat tgtcagaagt gataa                   2085
```

<210> SEQ ID NO 5
<211> LENGTH: 693
<212> TYPE: PRT
<213> ORGANISM: Artificial Sequence
<220> FEATURE:
<223> OTHER INFORMATION: HPV16 E6E7E2SH designer polypeptide

<400> SEQUENCE: 5

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Glu Asp Glu Ile
        35                  40                  45

Asp Gly Pro Ala Gly Gln Ala Glu Pro Asp Arg Ala His Tyr Asn Ile
    50                  55                  60

Val Thr Phe Cys Cys Lys Cys Asp Ser Thr Leu Arg Leu Cys Val Gln
65                  70                  75                  80

Ser Thr His Val Asp Ile Arg Thr Leu Glu Asp Leu Leu Met Gly Thr
                85                  90                  95

Leu Gly Ile Val Cys Pro Ile Cys Ser Gln Lys Pro Gly Thr Thr Leu
            100                 105                 110

Glu Gln Gln Tyr Asn Lys Pro Leu Cys Asp Leu Leu Ile Arg Cys Ile
        115                 120                 125

Asn Cys Gln Lys Pro Leu Cys Pro Glu Glu Lys Gln Arg His Leu Asp
    130                 135                 140

Lys Lys Gln Arg Phe His Asn Ile Arg Gly Arg Trp Thr Gly Arg Cys
145                 150                 155                 160

Met Ser Cys Cys Arg Ser Ser Arg Thr Arg Arg Glu Thr Gln Met His
                165                 170                 175

Gly Asp Thr Pro Thr Leu His Glu Tyr Met Leu Asp Leu Gln Pro Glu
            180                 185                 190

Thr Thr Asp Leu Tyr Cys Tyr Glu Gln Leu Asn Asp Ser Ser Glu Glu
        195                 200                 205

Glu Asp Glu Ile Asp Gly Pro Ala Gly Gln Ala Glu Pro Asp Arg Ala
    210                 215                 220
```

-continued

His Tyr Asn Ile Val Thr Phe Cys Cys Gln Leu Cys Thr Glu Leu Gln
225                 230                 235                 240

Thr Thr Ile His Asp Ile Ile Leu Glu Cys Val Tyr Cys Lys Gln Gln
            245                 250                 255

Leu Leu Arg Arg Glu Val Tyr Asp Phe Ala Phe Arg Asp Leu Cys Ile
        260                 265                 270

Val Tyr Arg Asp Gly Asn Pro Tyr Ala Val Cys Asp Lys Cys Leu Lys
    275                 280                 285

Phe Tyr Ser Lys Ile Ser Glu Tyr Arg His Tyr Cys Tyr Ser Leu Tyr
290                 295                 300

Gly Thr Thr Leu Glu Gln Gln Tyr Asn Lys Pro Leu Cys Asp Leu Leu
305                 310                 315                 320

Ile Arg Cys Ile Asn Cys Gln Lys Met Glu Thr Leu Cys Gln Arg Leu
            325                 330                 335

Asn Val Cys Gln Asp Lys Ile Leu Thr His Tyr Glu Asn Asp Ser Thr
        340                 345                 350

Asp Leu Arg Asp His Ile Asp Tyr Trp Lys His Met Arg Leu Glu Cys
    355                 360                 365

Ala Ile Tyr Tyr Lys Ala Arg Glu Met Gly Phe Lys His Ile Asn His
370                 375                 380

Gln Val Val Pro Thr Leu Ala Val Ser Lys Asn Lys Ala Leu Gln Ala
385                 390                 395                 400

Ile Glu Leu Gln Leu Thr Leu Glu Thr Ile Tyr Asn Ser Gln Tyr Ser
            405                 410                 415

Asn Glu Lys Trp Thr Leu Gln Asp Val Ser Leu Glu Val Tyr Leu Thr
        420                 425                 430

Ala Pro Thr Gly Cys Ile Lys Lys His Gly Tyr Thr Val Glu Val Gln
    435                 440                 445

Phe Asp Gly Asp Ile Cys Asn Thr Met His Tyr Thr Asn Trp Thr His
450                 455                 460

Ile Tyr Ile Cys Glu Glu Ala Ser Val Thr Val Val Glu Gly Gln Val
465                 470                 475                 480

Asp Tyr Tyr Gly Leu Tyr Tyr Val His Glu Gly Ile Arg Thr Tyr Phe
            485                 490                 495

Val Gln Phe Lys Asp Asp Ala Glu Lys Tyr Ser Lys Asn Lys Val Trp
        500                 505                 510

Glu Val His Ala Gly Gly Gln Val Ile Leu Cys Pro Thr Ser Val Phe
    515                 520                 525

Ser Ser Asn Glu Val Ser Ser Pro Glu Ile Ile Arg Gln His Leu Ala
530                 535                 540

Asn His Pro Ala Ala Thr His Thr Lys Ala Val Ala Leu Gly Thr Glu
545                 550                 555                 560

Glu Thr Gln Thr Thr Ile Gln Arg Pro Arg Ser Glu Pro Asp Thr Gly
            565                 570                 575

Asn Pro Cys His Thr Thr Lys Leu Leu His Arg Asp Ser Val Asp Ser
        580                 585                 590

Ala Pro Ile Leu Thr Ala Phe Asn Ser Ser His Lys Gly Arg Ile Asn
    595                 600                 605

Cys Asn Ser Asn Thr Thr Pro Ile Val His Leu Lys Val Asp Ala Asn
            610                 615                 620

Thr Leu Met Arg Leu Arg Tyr Arg Phe Lys Lys His Cys Thr Leu Tyr
625                 630                 635                 640

Thr Ala Val Ser Ser Thr Trp His Trp Thr Gly His Asn Val Lys His

```
              645                 650                 655
Lys Ser Ala Ile Val Thr Leu Thr Tyr Asp Ser Glu Trp Gln Arg Asp
            660                 665                 670

Gln Phe Leu Ser Gln Val Lys Ile Pro Lys Thr Ile Thr Val Ser Thr
            675                 680                 685

Gly Phe Met Ser Ile
        690

<210> SEQ ID NO 6
<211> LENGTH: 2085
<212> TYPE: DNA
<213> ORGANISM: Artificial Sequence
<220> FEATURE:
<223> OTHER INFORMATION: nt sequence encoding HPV16 E6E7E2SH designer
      polypeptide

<400> SEQUENCE: 6
atgcaccaga acggaccgc  catgttccag accccagg   aacggccag  aaagctgccc      60 cagctgtgca ccgagctgca gaccaccatc acgacatca tcctggaatg cgtgtactgc     120
aagcagcagc tggaagatga gatcgacggc cctgctggcc aggccgaacc cgacagagcc     180
cactacaata tcgtgaccct tctgctgcaag tgcgacagcc cctgcggct  gtgcgtgcag    240 agcacccacg tggacatccg accctggaa gatctgctga tgggcaccct gggcatcgtg     300
tgccccatct gcagccagaa acccggcacc accctggaac agcagtacaa caagcccctg     360
tgcgacctgc tgatccggtg catcaactgc agaaacccc  tgtgcccga  ggaaaagcag    420 cggcacctgg acaagaagca gcggttccac aacatccggg gcagatggac aggcagatgc     480
atgagctgct gcagaagcag ccggaccaga cgggaaaccc agatgcacgg cgacacccc     540 accctgcacg agtacatgct ggacctgcag cccgagacaa ccgacctgta ctgctacgag     600
cagctgaacg acagcagcga ggaagaggac gagattgacg acccgctgg acaggccgag     660 cctgaccggc tcactataa catcgtgaca ttttgctgtc agctctgtac tgaactccag     720
acaacaattc acgatattat tctcgaatgt gtgtattgta acagcagct  cctgcggaga    780 gaggtgtacg acttcgcctt ccgggacctc tgcatcgtgt atcgggacgg caaccctac     840 gccgtgtgcg acaagtgcct gaagttctac agcaagatca gcgagtaccg cactactgc     900 tacagcctgt acgaacaac  actcgaacag cagtataaca accactctg  tgatctgctg    960 attcgctgta tcaattgtca agaatggaa  accctgtgcc agcggctgaa cgtgtgccag    1020
gacaagatcc tgacccacta cgagaacgac agcaccgacc tgcgggacca catcgactac    1080
tggaagcaca tgcggctgga atgcgccatc tactacaagg ccagagagat gggcttcaag    1140
cacatcaacc accaggtggt gcccaccctg gccgtgtcca gaacaaggc  cctgcaggcc    1200 atcgagctgc agctgacct  ggaaaccatc tacaacagcc agtacagcaa cgagaagtgg    1260
accctgcagg acgtgtccct ggaagtgtac ctgaccgctc ccaccggctg catcaagaaa    1320
cacggctaca ccgtggaagt gcagttcgac ggcgacatct gcaacaccat gcactacacc    1380
aactggaccc acatctacat ctgcgaagag ccagcgtga  ccgtggtgga aggccaggtg    1440
gactactacg gcctgtacta cgtgcacgag ggcatccgga cctacttcgt gcagttcaag    1500
gacgacgccg agaagtacag caagaacaaa gtgtgggagg tgcacgctgg cggccaggtc    1560
atcctgtgcc ccaccagcgt gttcagcagc aacgaggtgt ccagcccga  gatcatccgg    1620 cagcacctgg ccaatcaccc tgccgccacc cacacaaagg ccgtgccct  gggcaccgag    1680 gaaacccaga ccaccatcca gcggcccaga agcgagcccg acaccggcaa tcctgccac    1740
```

-continued

```
accaccaagc tgctgcaccg ggacagcgtg gacagcgccc ctatcctgac cgccttcaac    1800
agcagccaca agggccggat caactgcaac agcaacacca cccccatcgt gcacctgaag    1860
gtggacgcca acaccctgat gcggctgcgg tacagattca agaagcactg caccctgtac    1920
accgccgtgt cctccacctg gcactggacc ggccacaacg tgaagcacaa gagcgccatc    1980
gtgaccctga cctacgacag cgagtggcag cgggaccagt tcctgagcca ggtcaaaatc    2040
cccaagacca tcaccgtgtc caccggcttc atgagcatct gataa                   2085
```

<210> SEQ ID NO 7
<211> LENGTH: 18
<212> TYPE: PRT
<213> ORGANISM: Artificial Sequence
<220> FEATURE:
<223> OTHER INFORMATION: IgE leader peptide

<400> SEQUENCE: 7

```
Met Asp Trp Thr Trp Ile Leu Phe Leu Val Ala Ala Ala Thr Arg Val
1               5                   10                  15

His Ser
```

<210> SEQ ID NO 8
<211> LENGTH: 54
<212> TYPE: DNA
<213> ORGANISM: Artificial Sequence
<220> FEATURE:
<223> OTHER INFORMATION: nt sequence encoding IgE leader peptide

<400> SEQUENCE: 8

```
atggactgga cctggatcct gttcctggtg gctgccgcaa cccgggtgca cagc          54
```

<210> SEQ ID NO 9
<211> LENGTH: 21
<212> TYPE: PRT
<213> ORGANISM: Artificial Sequence
<220> FEATURE:
<223> OTHER INFORMATION: HAVT20 leader peptide

<400> SEQUENCE: 9

```
Met Ala Cys Pro Gly Phe Leu Trp Ala Leu Val Ile Ser Thr Cys Leu
1               5                   10                  15

Glu Phe Ser Met Ala
            20
```

<210> SEQ ID NO 10
<211> LENGTH: 63
<212> TYPE: DNA
<213> ORGANISM: Artificial Sequence
<220> FEATURE:
<223> OTHER INFORMATION: nt sequence encoding HAVT20 leader peptide

<400> SEQUENCE: 10

```
atggcctgcc ccggctttct gtgggccctg gtcatcagca cctgtctgga attcagcatg    60
gcc                                                                  63
```

<210> SEQ ID NO 11
<211> LENGTH: 54
<212> TYPE: DNA
<213> ORGANISM: Artificial Sequence
<220> FEATURE:
<223> OTHER INFORMATION: 2xTetO-containing sequence

<400> SEQUENCE: 11
gagctctccc tatcagtgat agagatctcc ctatcagtga tagagatcgt cgac      54

<210> SEQ ID NO 12
<211> LENGTH: 28
<212> TYPE: DNA
<213> ORGANISM: Artificial Sequence
<220> FEATURE:
<223> OTHER INFORMATION: 2xCuO-containing sequence

<400> SEQUENCE: 12
aacaaacaga caatctggtc tgtttgta      28

<210> SEQ ID NO 13
<211> LENGTH: 829
<212> TYPE: DNA
<213> ORGANISM: Artificial Sequence
<220> FEATURE:
<223> OTHER INFORMATION: CMV promoter

<400> SEQUENCE: 13
tcaatattgg ccattagcca tattattcat tggttatata gcataaatca atattggcta      60
ttggccattg catacgttgt atccatatca taatatgtac atttatattg gctcatgtcc     120
aacattaccg ccatgttgac attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtacg ccccctattg acgtcaatga     420
cggtaaatgg cccgcctggc attatgccca gtacatgacc ttatgggact ttcctacttg     480
gcagtacatc tacgtattag tcatcgctat taccatggtg atgcggtttt ggcagtacat     540
caatgggcgt ggatagcggt ttgactcacg gggatttcca agtctccacc ccattgacgt     600
caatgggagt ttgttttggc accaaaatca acgggacttt ccaaaatgtc gtaacaactc     660
cgccccattg acgcaaatgg gcggtaggcg tgtacggtgg gaggtctata taagcagagc     720
tcgtttagtg aaccgtcaga tcgcctggag acgccatcca cgctgttttg acctccatag     780
aagacaccgg gaccgatcca gcctccgcgg ccgggaacgg tgcattgga             829

<210> SEQ ID NO 14
<211> LENGTH: 657
<212> TYPE: DNA
<213> ORGANISM: Artificial Sequence
<220> FEATURE:
<223> OTHER INFORMATION: nt sequence encoding TetR polypeptide

<400> SEQUENCE: 14
atgtctagat tagataaaag taaagtgatt aacagcgcat tagagctgct taatgaggtc      60
ggaatcgaag gtttaacaac ccgtaaactc gcccagaagc taggtgtaga gcagcctaca     120
ttgtattggc atgtaaaaaa taagcgggct tgctcgacg ccttagccat tgagatgtta     180
gataggcacc atactcactt tgcccttta gaaggggaaa gctggcaaga tttttttacgt     240
aatacgcta aagttttag atgtgcttta ctaagtcatc gcgatggagc aaaagtacat     300
ttaggtacac ggcctacaga aaacagtat gaaactctcg aaaatcaatt agccttttta     360
tgccaacaag gtttttcact agagaatgca ttatatgcac tcagcgctgt ggggcatttt     420
actttaggtt gcgtattgga agatcaagag catcaagtcg ctaaagaaga aagggaaaca     480
cctactactg atagtatgcc gccattatta cgacaagcta tcgaattatt tgatcaccaa    540
ggtgcagagc cagccttctt attcggcctt gaattgatca tatgcggatt agaaaaacaa    600
cttaaatgtg aaagtgggtc cgcgtacagc ggatcccggg aattcagatc ttattaa      657

<210> SEQ ID NO 15
<211> LENGTH: 218
<212> TYPE: PRT
<213> ORGANISM: Artificial Sequence
<220> FEATURE:
<223> OTHER INFORMATION: TetR polypeptide

<400> SEQUENCE: 15

Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Gly Ser Arg Glu Phe Arg Ser Tyr
    210                 215

<210> SEQ ID NO 16
<211> LENGTH: 612
<212> TYPE: DNA
<213> ORGANISM: Artificial Sequence
<220> FEATURE:
<223> OTHER INFORMATION: nt sequence encoding CymR polypeptide

<400> SEQUENCE: 16
atgtctccca acgacggac tcaagcggaa agggcaatgg aaactcaggg taagctgatt     60
gccgcggctc tgggagtgct gcgagagaaa gggtatgccg ggtttcgcat agccgacgtt    120
cctggagctg caggcgtaag cagaggagcc caatctcatc actttccgac caagctggag    180
cttttgctgg ctaccttcga atggctgtac gagcagatca cggaaaggag tcgtgctagg    240
ctggccaagc tgaaacccga ggatgatgtc attcagcaga tgctggacga tgcagccgag    300
ttcttcctgg acgacgactt cagcatcagt ctcgacctca tcgtagccgc agatcgcgat    360

```
ccagctttgc gcgagggcat acagagaaca gtcgagcgga atcggtttgt ggtggaggac    420
atgtggcttg tgttctggt gagcagaggc ctctcacggg atgatgccga ggacatcctg     480
tggctgatct taactccgt cagagggttg gcagtgaggt ccctttggca aaggacaaa      540 gaacggtttg aacgtgtgcg aaactcaaca ctcgagattg ctagggaacg ctacgccaag    600
ttcaagagat ga                                                         612
```

```
<210> SEQ ID NO 17
<211> LENGTH: 203
<212> TYPE: PRT
<213> ORGANISM: Artificial Sequence
<220> FEATURE:
<223> OTHER INFORMATION: CymR polypeptide

<400> SEQUENCE: 17
```

Met Ser Pro Lys Arg Arg Thr Gln Ala Glu Arg Ala Met Glu Thr Gln
1               5                   10                  15

Gly Lys Leu Ile Ala Ala Ala Leu Gly Val Leu Arg Glu Lys Gly Tyr
            20                  25                  30

Ala Gly Phe Arg Ile Ala Asp Val Pro Gly Ala Ala Gly Val Ser Arg
        35                  40                  45

Gly Ala Gln Ser His His Phe Pro Thr Lys Leu Glu Leu Leu Leu Ala
    50                  55                  60

Thr Phe Glu Trp Leu Tyr Glu Gln Ile Thr Glu Arg Ser Arg Ala Arg
65                  70                  75                  80

Leu Ala Lys Leu Lys Pro Glu Asp Asp Val Ile Gln Gln Met Leu Asp
                85                  90                  95

Asp Ala Ala Glu Phe Phe Leu Asp Asp Phe Ser Ile Ser Leu Asp
            100                 105                 110

Leu Ile Val Ala Ala Asp Arg Asp Pro Ala Leu Arg Glu Gly Ile Gln
        115                 120                 125

Arg Thr Val Glu Arg Asn Arg Phe Val Val Glu Asp Met Trp Leu Gly
    130                 135                 140

Val Leu Val Ser Arg Gly Leu Ser Arg Asp Asp Ala Glu Asp Ile Leu
145                 150                 155                 160

Trp Leu Ile Phe Asn Ser Val Arg Gly Leu Ala Val Arg Ser Leu Trp
                165                 170                 175

Gln Lys Asp Lys Glu Arg Phe Glu Arg Val Arg Asn Ser Thr Leu Glu
            180                 185                 190

Ile Ala Arg Glu Arg Tyr Ala Lys Phe Lys Arg
        195                 200

```
<210> SEQ ID NO 18
<211> LENGTH: 25
<212> TYPE: PRT
<213> ORGANISM: Artificial Sequence
<220> FEATURE:
<223> OTHER INFORMATION: HPV16 E6 aa41-65

<400> SEQUENCE: 18
```

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

```
<210> SEQ ID NO 19
<211> LENGTH: 35
```

```
<212> TYPE: PRT
<213> ORGANISM: Artificial Sequence
<220> FEATURE:
<223> OTHER INFORMATION: HPV16 E7 aa43-77

<400> SEQUENCE: 19

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
                20                  25                  30

Asp Ile Arg
            35

<210> SEQ ID NO 20
<211> LENGTH: 331
<212> TYPE: PRT
<213> ORGANISM: Artificial Sequence
<220> FEATURE:
<223> OTHER INFORMATION: HPV18-E6E7SH designer polypeptide

<400> SEQUENCE: 20

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys
                20                  25                  30

Val Tyr Cys Lys Thr Val Leu Asp Leu Cys His Gln Gln Leu Ser
                35                  40                  45

Asp Ser Glu Glu Glu Asn Asp Glu Ile Asp Gly Val Asn His Gln His
        50                  55                  60

Leu Pro Ala Arg Arg Ala Glu Pro Gln Arg His Thr Met Leu Cys Met
65                  70                  75                  80

Cys Cys Lys Cys Glu Ala Arg Ile Glu Leu Val Val Glu Ser Ser Ala
                85                  90                  95

Asp Asp Leu Arg Ala Phe Gln Gln Leu Phe Leu Asn Thr Leu Ser Phe
            100                 105                 110

Val Cys Pro Trp Cys Ala Ser Gln His Tyr Ser Asp Ser Val Tyr Gly
        115                 120                 125

Asp Thr Leu Glu Lys Leu Thr Asn Thr Gly Leu Tyr Asn Leu Leu Ile
    130                 135                 140

Arg Cys Leu Arg Cys Gln Lys Pro Leu Asn Pro Ala Glu Lys Leu Arg
145                 150                 155                 160

His Leu Asn Glu Lys Arg Arg Phe His Asn Ile Ala Gly His Tyr Arg
                165                 170                 175

Gly Gln Cys His Ser Cys Cys Asn Arg Ala Arg Gln Glu Arg Leu Gln
            180                 185                 190

Arg Arg Arg Glu Thr Met His Gly Pro Lys Ala Thr Leu Gln Asp Ile
        195                 200                 205

Val Leu His Leu Glu Pro Gln Asn Glu Ile Pro Val Asp Leu Leu Cys
    210                 215                 220

His Glu Gln Leu Ser Asp Ser Glu Glu Glu Asn Asp Glu Ile Asp Gly
225                 230                 235                 240

Val Asn Pro Asp Leu Cys Thr Glu Leu Asn Thr Ser Leu Gln Asp Ile
                245                 250                 255

Glu Ile Thr Cys Val Tyr Cys Lys Thr Val Leu Glu Leu Thr Glu Val
            260                 265                 270

Phe Glu Phe Ala Phe Lys Asp Leu Phe Val Val Tyr Arg Asp Ser Ile
        275                 280                 285
```

Pro His Ala Ala Cys His Lys Cys Ile Asp Phe Tyr Ser Arg Ile Arg
    290                    295                  300

Glu Leu Arg His Tyr Ser Asp Ser Val Tyr Gly Asp Thr Leu Glu Lys
305                    310                    315                  320

Leu Thr Asn Thr Gly Leu Tyr Asn Leu Leu Ile
    325                    330

<210> SEQ ID NO 21
<211> LENGTH: 999
<212> TYPE: DNA
<213> ORGANISM: Artificial Sequence
<220> FEATURE:
<223> OTHER INFORMATION: nt sequence of HPV18-E6E7SH designer sequence

<400> SEQUENCE: 21

```
atggccagat tcgaggaccc caccagacgg ccctacaagc tgcccgacct gtgcaccgag      60
ctgaacacat ctctgcagga catcgagatc acatgcgtgt actgcaagac cgtgctggac     120
ctgctgtgcc acgagcagct gtccgactcc gaggaagaaa cgacgagat cgacggcgtg      180 aaccatcagc atctgcccgc cagacgggcc gagccccaga cacaccat gctgtgcatg      240 tgctgcaagt gcgaggcccg gattgagctg gtggtgaaa gcagcgccga cgacctgcgg     300
gccttccagc agctctttct gaatacccctg agcttcgtgt gcccttggtg cgccagccag     360
cactacagcg actccgtgta cggcgatacc ctggaaaagc tgaccaatac cggcctgtat     420
aacctgctga tccggtgcct gcggtgccag aagcccctga tcccgccga aaactgaga      480 cacctgaacg agaagcggcg gttccacaat atcgccggcc actacagagg ccagtgccac     540
agctgctgca accgggccag acaggaacgg ctgcagcgga ggcgggaaac catgcacgga     600
cccaaggcca ccctccagga cattgtcctg cacctggaac cccagaacga gatccccgtc     660
gatctgctgt gtcatgaaca gctcagcgac agcgaagagg aaaatgacga aattgacggg     720
gtcaaccctg acctctgtac cgaactcaat accagtctcc aggatatcga aattacctgt     780
gtctactgta aaaccgtcct cgagctgacc gaggtgttcg agttcgcctt caaggacctg     840
tttgtggtgt acagagacag catcccccac gccgcctgcc acaagtgcat cgacttctac     900
agccggatca gagagctgcg gcactactcc gattctgtgt atggcgacac actcgagaag     960
ctcacaaaca caggactgta caatctgctc atctgataa                           999
```

<210> SEQ ID NO 22
<211> LENGTH: 696
<212> TYPE: PRT
<213> ORGANISM: Artificial Sequence
<220> FEATURE:
<223> OTHER INFORMATION: HPV18-E2E6E7SH designer sequence

<400> SEQUENCE: 22

Met Gln Thr Pro Lys Glu Thr Leu Ser Glu Arg Leu Ser Ala Leu Gln
1               5                    10                  15

Asp Lys Ile Ile Asp His Tyr Glu Asn Asp Ser Lys Asp Ile Asp Ser
                20                    25                  30

Gln Ile Gln Tyr Trp Gln Leu Ile Arg Trp Glu Asn Ala Ile Phe Phe
            35                    40                  45

Ala Ala Arg Glu His Gly Ile Gln Thr Leu Asn His Gln Val Val Pro
    50                    55                    60

Ala Tyr Asn Ile Ser Lys Ser Lys Ala His Lys Ala Ile Glu Leu Gln
65                  70                    75                  80

```
Met Ala Leu Gln Gly Leu Ala Gln Ser Ala Tyr Lys Thr Glu Asp Trp
                    85                  90                  95
Thr Leu Gln Asp Thr Cys Glu Glu Leu Trp Asn Thr Glu Pro Thr His
                100                 105                 110
Cys Phe Lys Lys Gly Gly Gln Thr Val Gln Val Tyr Phe Asp Gly Asn
                115                 120                 125
Lys Asp Asn Cys Met Thr Tyr Val Ala Trp Asp Ser Val Tyr Tyr Met
130                 135                 140
Thr Asp Ala Gly Thr Trp Asp Lys Thr Ala Thr Cys Val Ser His Arg
145                 150                 155                 160
Gly Leu Tyr Tyr Val Lys Glu Gly Tyr Asn Thr Phe Tyr Ile Glu Phe
                    165                 170                 175
Lys Ser Glu Cys Glu Lys Tyr Gly Asn Thr Gly Thr Trp Glu Val His
                180                 185                 190
Phe Gly Asn Asn Val Ile Asp Cys Asn Asp Ser Met Cys Ser Thr Ser
                195                 200                 205
Asp Asp Thr Val Ser Ala Thr Gln Leu Val Lys Gln Leu Gln His Thr
    210                 215                 220
Pro Ser Pro Tyr Ser Ser Thr Val Ser Val Gly Thr Ala Lys Thr Tyr
225                 230                 235                 240
Gly Gln Thr Ser Ala Ala Thr Arg Pro Gly His Cys Gly Leu Ala Glu
                    245                 250                 255
Lys Gln His Cys Gly Pro Val Asn Pro Leu Leu Gly Ala Ala Thr Pro
                260                 265                 270
Thr Gly Asn Asn Lys Arg Arg Lys Leu Cys Ser Gly Asn Thr Thr Pro
                275                 280                 285
Ile Ile His Leu Lys Val Asp Arg Asn Ser Leu Met Arg Leu Arg Tyr
290                 295                 300
Arg Leu Arg Lys His Ser Asp His Tyr Arg Asp Ile Ser Ser Thr Trp
305                 310                 315                 320
His Trp Thr Gly Ala Gly Asn Glu Lys Thr Gly Ile Leu Thr Val Thr
                    325                 330                 335
Tyr His Ser Glu Thr Gln Arg Thr Lys Phe Leu Asn Thr Val Ala Ile
                340                 345                 350
Pro Asp Ser Val Gln Ile Leu Val Gly Tyr Met Thr Met Met Ala Arg
                355                 360                 365
Phe Glu Asp Pro Thr Arg Arg Pro Tyr Lys Leu Pro Asp Leu Cys Thr
                370                 375                 380
Glu Leu Asn Thr Ser Leu Gln Asp Ile Glu Ile Thr Cys Val Tyr Cys
385                 390                 395                 400
Lys Thr Val Leu Asp Leu Leu Cys His Glu Gln Leu Ser Asp Ser Glu
                    405                 410                 415
Glu Glu Asn Asp Glu Ile Asp Gly Val Asn His Gln His Leu Pro Ala
                420                 425                 430
Arg Arg Ala Glu Pro Gln Arg His Thr Met Leu Cys Met Cys Cys Lys
                435                 440                 445
Cys Glu Ala Arg Ile Glu Leu Val Val Glu Ser Ser Ala Asp Asp Leu
                450                 455                 460
Arg Ala Phe Gln Gln Leu Phe Leu Asn Thr Leu Ser Phe Val Cys Pro
465                 470                 475                 480
Trp Cys Ala Ser Gln His Tyr Ser Asp Ser Val Tyr Gly Asp Thr Leu
                    485                 490                 495
Glu Lys Leu Thr Asn Thr Gly Leu Tyr Asn Leu Leu Ile Arg Cys Leu
```

```
                500              505              510
Arg Cys Gln Lys Pro Leu Asn Pro Ala Glu Lys Leu Arg His Leu Asn
            515                  520                  525

Glu Lys Arg Arg Phe His Asn Ile Ala Gly His Tyr Arg Gly Gln Cys
        530                  535                  540

His Ser Cys Cys Asn Arg Ala Arg Gln Glu Arg Leu Gln Arg Arg Arg
545                  550                  555                  560

Glu Thr Met His Gly Pro Lys Ala Thr Leu Gln Asp Ile Val Leu His
                565                  570                  575

Leu Glu Pro Gln Asn Glu Ile Pro Val Asp Leu Leu Cys His Glu Gln
            580                  585                  590

Leu Ser Asp Ser Glu Glu Glu Asn Asp Glu Ile Asp Gly Val Asn Pro
        595                  600                  605

Asp Leu Cys Thr Glu Leu Asn Thr Ser Leu Gln Asp Ile Glu Ile Thr
    610                  615                  620

Cys Val Tyr Cys Lys Thr Val Leu Glu Leu Thr Glu Val Phe Glu Phe
625                  630                  635                  640

Ala Phe Lys Asp Leu Phe Val Val Tyr Arg Asp Ser Ile Pro His Ala
                645                  650                  655

Ala Cys His Lys Cys Ile Asp Phe Tyr Ser Arg Ile Arg Glu Leu Arg
            660                  665                  670

His Tyr Ser Asp Ser Val Tyr Gly Asp Thr Leu Glu Lys Leu Thr Asn
        675                  680                  685

Thr Gly Leu Tyr Asn Leu Leu Ile
    690                  695

<210> SEQ ID NO 23
<211> LENGTH: 2094
<212> TYPE: DNA
<213> ORGANISM: Artificial Sequence
<220> FEATURE:
<223> OTHER INFORMATION: nt sequence of HPV18-E2E6E7SH designer sequence

<400> SEQUENCE: 23
atgcagaccc ccaaagagac actgagcgag cggctgagcg ccctgcagga caagatcatc    60
gaccactacg agaacgacag caaggacatc gacagccaga tccagtactg gcagctgatc   120
agatgggaga cgccatcttc cttcgccgcc agagagcacg gcatccagac cctgaaccac   180
caggtggtgc ccgcctacaa catcagcaag agcaaggccc acaaggctat cgagctgcag   240
atggccctgc agggactggc ccagagcgcc tacaagaccg aggactggac cctgcaggat   300
acctgcgagg aactgtggaa caccgagccc acccactgct tcaagaaagg cggccagacc   360
gtgcaggtgt acttcgacgg caacaaggac aactgcatga cctacgtggc ctgggacagc   420
gtgtactaca tgaccgacgc cggcacctgg acaagaccg ccacctgtgt gtcccaccgg   480
ggcctgtact acgtgaaaga gggctacaac accttctaca tcgagttcaa gagcgagtgc   540
gagaagtacg gcaacaccgg acatgggag gtgcacttcg gcaacaacgt gatcgactgc   600
aacgacagca tgtgcagcac cagcgacgac accgtgtccg ccacccagct ggtgaaacag   660
ctgcagcaca cccccagccc ctacagcagc ccgtgtctg tgggcaccgc caagacctac   720
ggccagacca gcgccgccac cagacctgga cactgtggcc tggccgagaa gcagcactgc   780
ggccctgtga accctctgct gggagccgcc acccccaccg gcaacaacaa gcggagaaag   840
ctgtgcagcg gcaacaccac ccccatcatc cacctgaagg tggaccggaa cagcctgatg   900
cggctgcggt acagactgcg gaagcacagc gaccactacc gggacatcag cagcacctgg   960
```

```
cactggaccg gcgctggcaa cgagaaaacc ggcatcctga ccgtgaccta ccacagcgaa      1020
acccagcgga ccaagttcct gaacaccgtg gccatccccg acagcgtgca gatcctggtg      1080
ggatatatga ccatgatggc cagattcgag gaccccacca gacggcccta caagctgccc      1140
gacctgtgca ccgagctgaa cacatctctg caggacatcg agatcacatg cgtgtactgc      1200
aagaccgtgc tggacctgct gtgccacgag cagctgtccg actccgagga agaaaacgac      1260
gagatcgacg gcgtgaacca tcagcatctg cccgccagac gggccgagcc cagagacac      1320 accatgctgt gcatgtgctg caagtgcgag gcccggattg agctggtggt ggaaagcagc      1380
gccgacgacc tgcgggcctt ccagcagctc tttctgaata ccctgagctt cgtgtgccct      1440
tggtgcgcca gcagcacta cagcgactcc gtgtacggcg ataccctgga aaagctgacc      1500
aataccggcc tgtataacct gctgatccgg tgcctgcggt gccagaagcc cctgaatccc      1560
gccgagaaac tgagacacct gaacgagaag cggcggttcc acaatatcgc cggccactac      1620
agaggccagt gccacagctg ctgcaaccgg gccagacagg aacggctgca gcggaggcgg      1680
gaaaccatgc acggacccaa ggccaccctc caggacattg tcctgcacct ggaaccccag      1740
aacgagatcc ccgtcgatct gctgtgtcat gaacagctca gcgacagcga agaggaaaat      1800
gacgaaattg acggggtcaa ccctgacctc tgtaccgaac tcaataccag tctccaggat      1860
atcgaaatta cctgtgtcta ctgtaaaacc gtcctgagc tgaccgaggt gttcgagttc      1920
gccttcaagg acctgtttgt ggtgtacaga gacagcatcc cccacgccgc ctgccacaag      1980
tgcatcgact tctacagccg gatcagagag ctgcggcact actccgattc tgtgtatggc      2040
gacacactcg agaagctcac aaacacagga ctgtacaatc tgctcatctg ataa           2094
```

<210> SEQ ID NO 24
<211> LENGTH: 338
<212> TYPE: PRT
<213> ORGANISM: Artificial Sequence
<220> FEATURE:
<223> OTHER INFORMATION: HPV18DS2 amino acid sequence

<400> SEQUENCE: 24

```
Met His Gly Pro Lys Ala Thr Leu Gln Asp Ile Val Leu His Leu Glu
 1               5                  10                  15

Pro Gln Asn Glu Ile Pro Val Asp Leu Leu Cys His Glu Gln Leu Ser
            20                  25                  30

Asp Ser Glu Glu Glu Asn Asp Glu Ile Asp Gly Val Asn His Gln His
        35                  40                  45

Leu Pro Ala Arg Arg Ala Glu Pro Gln Arg His Thr Ser Leu Gln Asp
    50                  55                  60

Ile Glu Ile Thr Cys Val Tyr Cys Lys Thr Val Leu Glu Leu Thr Glu
65                  70                  75                  80

Val Phe Glu Phe Ala Phe Lys Asp Leu Phe Val Val Tyr Arg Asp Ser
                85                  90                  95

Ile Pro His Ala Ala Cys His Lys Cys Ile Asp Phe Tyr Ser Arg Ile
            100                 105                 110

Arg Glu Leu Arg His Tyr Ser Asp Ser Val Tyr Gly Asp Thr Leu Glu
        115                 120                 125

Lys Leu Thr Asn Thr Gly Leu Tyr Asn Leu Leu Ile Arg Cys Leu Gln
    130                 135                 140

Arg Phe Glu Asp Pro Thr Arg Arg Pro Tyr Lys Leu Pro Asp Leu Cys
145                 150                 155                 160
```

-continued

```
Thr Glu Leu Asn Thr Ser Leu Gln Asp Ile Glu Ile Thr Cys Val Tyr
                165                 170                 175
Cys Lys Thr Val Leu Glu Leu Thr Glu Val Phe Glu Phe Ala Asp Ser
            180                 185                 190
Glu Glu Glu Asn Asp Glu Ile Asp Gly Val Asn His Gln His Leu Pro
        195                 200                 205
Ala Arg Arg Ala Glu Pro Gln Arg His Thr Met Leu Cys Met Cys Cys
    210                 215                 220
Lys Cys Glu Ala Arg Ile Glu Leu Val Val Glu Ser Ser Ala Asp Asp
225                 230                 235                 240
Leu Arg Ala Phe Gln Gln Leu Phe Leu Asn Thr Leu Ser Phe Val Cys
                245                 250                 255
Pro Trp Cys Ala Ser Gln Ser Asp Ser Val Tyr Gly Asp Thr Leu Glu
            260                 265                 270
Lys Leu Thr Asn Thr Gly Leu Tyr Asn Leu Leu Ile Arg Cys Leu Arg
        275                 280                 285
Cys Gln Lys Pro Leu Asn Pro Ala Glu Lys Leu Arg His Leu Asn Glu
    290                 295                 300
Lys Arg Arg Phe His Asn Ile Ala Gly His Tyr Arg Gly Gln Cys His
305                 310                 315                 320
Ser Cys Cys Asn Arg Ala Arg Gln Glu Arg Leu Gln Arg Arg Arg Glu
                325                 330                 335
Thr Gln
```